United States Patent
Zonari et al.

(10) Patent No.: US 12,268,747 B2
(45) Date of Patent: Apr. 8, 2025

(54) POLYPEPTIDES HAVING ANTI-SENESCENT EFFECTS AND USES THEREOF

(71) Applicants: OneSkin, Inc., San Francisco, CA (US); UNIVERSIDADE CATÓLICA DE BRASÍLIA, ÁGUAS CLARAS—DF (BR); UNIÃO BRASILEIRA DE EDUCAçÃO CATÕLICA, BRASÍLIA, BRASÍLIA—DF (BR)

(72) Inventors: Alessandra Zonari, San Francisco, CA (US); Carolina Reis de Oliveira, San Francisco, CA (US); Edgar Andres Ochoa, San Francisco, CA (US); Juliana Lott de Carvalho, Brasilia (BR); Lear Brace, Oakland, CA (US); Mariana Boroni, Rio de Janeiro (BR); Mylieneth Guiang, San Francisco, CA (US); Octávio Franco, Campo Grande (BR); William Farias Porto, Ceilândia (BR); Thuany de Alencar e Silva, Brasilia (BR)

(73) Assignees: OneSkin, Inc., San Francisco, CA (US); Universidade Catolica de Brasilia, Aguas Claras (BR); Uniao Brasileira de Educacao Catolica, Brasilia, Brasilia (BR)

( * ) Notice: Subject to any disclaimer, the term of this patent is extended or adjusted under 35 U.S.C. 154(b) by 0 days.

(21) Appl. No.: 18/674,657

(22) Filed: May 24, 2024

(65) Prior Publication Data
US 2024/0342290 A1 Oct. 17, 2024

Related U.S. Application Data

(62) Division of application No. 16/936,177, filed on Jul. 22, 2020.

(60) Provisional application No. 62/877,164, filed on Jul. 22, 2019.

(51) Int. Cl.
| | |
|---|---|
| *A61K 47/42* | (2017.01) |
| *A61K 9/06* | (2006.01) |
| *A61K 38/07* | (2006.01) |
| *A61K 38/08* | (2019.01) |
| *A61K 38/16* | (2006.01) |
| *A61K 47/46* | (2006.01) |
| *A61K 47/55* | (2017.01) |
| *C07K 7/06* | (2006.01) |

(52) U.S. Cl.
CPC ........... *A61K 47/42* (2013.01); *A61K 9/06* (2013.01); *A61K 38/07* (2013.01); *A61K 38/08* (2013.01); *A61K 38/16* (2013.01); *A61K 47/46* (2013.01); *A61K 47/551* (2017.08); *C07K 7/06* (2013.01)

(58) Field of Classification Search
None
See application file for complete search history.

(56) References Cited

U.S. PATENT DOCUMENTS

| | | |
|---|---|---|
| 5,972,602 A | 10/1999 | Hyland et al. |
| 6,033,854 A | 3/2000 | Kurnit et al. |
| 6,180,349 B1 | 1/2001 | Ginzinger et al. |
| 6,287,778 B1 | 9/2001 | Huang et al. |
| 2003/0207280 A1 | 11/2003 | Hsiao et al. |
| 2005/0069879 A1 | 3/2005 | Berlin |
| 2006/0107345 A1 | 5/2006 | Alexandrov et al. |
| 2008/0234183 A1 | 9/2008 | Hallbrink et al. |
| 2010/0086501 A1 | 4/2010 | Chang et al. |
| 2011/0070296 A1 | 3/2011 | Lee et al. |
| 2011/0124111 A1 | 5/2011 | Hoshizaki et al. |
| 2011/0128545 A1 | 6/2011 | Cox et al. |
| 2011/0281788 A1 | 11/2011 | Coote et al. |
| 2013/0337087 A1 | 12/2013 | Finlay et al. |
| 2014/0228231 A1 | 8/2014 | Vilain et al. |
| 2016/0168632 A1 | 6/2016 | Edwards |
| 2016/0222448 A1 | 8/2016 | Horvath |
| 2017/0296640 A1 | 10/2017 | Schoor et al. |
| 2018/0015137 A1 | 1/2018 | De Keizer |
| 2019/0078162 A1 | 3/2019 | Reis De Oliveira et al. |
| 2021/0038729 A1 | 2/2021 | Zonari et al. |

FOREIGN PATENT DOCUMENTS

| | | |
|---|---|---|
| CN | 1569220 A | 1/2005 |
| JP | 2010115131 A | 5/2010 |
| JP | 2011514338 A | 5/2011 |
| JP | 2018508196 A | 3/2018 |
| KR | 20110011009 A | 2/2011 |
| WO | WO-0056753 A1 | 9/2000 |
| WO | WO-0070090 A1 | 11/2000 |
| WO | WO-0112851 A2 | 2/2001 |
| WO | WO-03060122 A1 | 7/2003 |
| WO | WO-2004108757 A2 | 12/2004 |

(Continued)

OTHER PUBLICATIONS

Danczak-Pazdrowska et al., Aging Cell 22:e13845 (2023) (Year: 2023).*
Ramble, T., "What Sunscreen Ingredients to Look for—and Which Banned Ones to Avoid," available online at https://www.healthline.com/health/beauty-skin-care/best-sunscreen-ingredients#TOC_TITLE_HDR_1, 15 pages (Jun. 14, 2019) (Year: 2019).*

(Continued)

*Primary Examiner* — Thea D' Ambrosio
(74) *Attorney, Agent, or Firm* — WILSON SONSINI GOODRICH & ROSATI

(57) ABSTRACT

Polypeptides which can provide a senotherapeutic effect are provided herein. The polypeptides can be formulated for topical application and can be applied topically to a subject to provide a senotherapeutic effect in the subject or in the cells of the subject.

14 Claims, 19 Drawing Sheets
Specification includes a Sequence Listing.

(56) References Cited

FOREIGN PATENT DOCUMENTS

| | | |
|---|---|---|
| WO | WO-2005007129 A2 | 1/2005 |
| WO | WO-2006084132 A2 | 8/2006 |
| WO | WO-2008143679 A2 | 11/2008 |
| WO | WO-2009133098 A2 | 11/2009 |
| WO | WO-2017070618 A1 | 4/2017 |
| WO | WO-2018199341 A1 | 11/2018 |
| WO | WO-2019074615 A2 | 4/2019 |
| WO | WO-2019074615 A3 | 5/2019 |
| WO | WO-2021016330 A2 | 1/2021 |
| WO | WO-2021016330 A3 | 3/2021 |

OTHER PUBLICATIONS

National Cancer Institute, "Senescence", Natl. Cancer Inst., available online at https://www.cancer.gov/publications/dictionaries/cancer-terms/def/senescence, 1 page (accessed on Nov. 2, 2024) (Year: 2024).*

Alencar-Silva, T. et al., Breaking the frontiers of cosmetology with antimicrobial peptides. Biotechnol. Adv. 36, 2019-2031 (2018).

Althubiti, M. et al., Characterization of novel markers of senescence and their prognostic potential in cancer. Cell Death Dis. 5, e1528 (2014).

Altschul, Stephen F et al., Basic Local Alignment Search Tool. Journal of Molecular Biology vol. 215,3: pp. 403-410 (1990).

Altschul, Stephen F et al., Gapped BLAST and PSI-BLAST: A New Generation Of Protein Database Search Programs. Nucleic Acids Research vol. 25, 17: pp. 3389-3402 (1997).

Anders, S. et al., HTSeq—a Python framework to work with high-throughput sequencing data. Bioinformatics 31, 166-169 (2015).

Aryee, M. J. et al., Minfi: a flexible and comprehensive Bioconductor package for the analysis of Infinium DNA methylation microarrays. Bioinformatics 30, 1363-1369 (2014).

Baar, M. P. et al., Targeted Apoptosis of Senescent Cells Restores Tissue Homeostasis in Response to Chemotoxicity and Aging. Cell vol. 169 132-147.e16 (2017).

Baker, D. J. et al., Naturally occurring p16Ink4a-positive cells shorten healthy lifespan. Nature vol. 530 184-189 (2016).

Banito, A. et al., Senescence impairs successful reprogramming to pluripotent stem cells. Genes Dev. 23, 2134-2139 (2009).

Basisty, N. et al., A proteomic atlas of senescence-associated secretomes for aging biomarker development. PLoS Biol. 18, e3000599 (2020).

Bekaert et al., Improved age determination of blood and teeth samples using a selected set of DNA methylation markers. Epigenetics 10(10):922-930 (2015).

Bell, et al., DNA methylation aging clocks: challenges and recommendations. Genome Biol 20:249 (1-24) (2019).

Binder et al., Faster ticking rate of the epigenetic clock is associated with faster pubertal development in girls. Epigenetics 13(1):85-94 (2017).

Bolger, A. M., Trimmomatic: a flexible trimmer for Illumina sequence data. Bioinformatics 30, 2114-2120 (2014).

Bormann et al., Reduced DNA methylation patterning and transcriptional connectivity define human skin aging. Aging Cell 15(3):563-571 (2016).

Bormann, Source for Dataset E-MTAB-4385 cited in Reduced DNA methylation patterning and transcriptional connectivity define human skin aging, Aging Cell by the Anatomical Society and John Willey & Sons Ltd, 15(3):563-571 (2016); downloaded from https://www.ebi.ac.uk/arrayexpress/experiments/E-MTAB-4385/ on Mar. 17, 2020.

Boroni, M. et al., Highly accurate skin-specific methylome analysis algorithm as a platform to screen and validate therapeutics for healthy aging. Clinical Epigenetics vol. 12 (2020).

Brace, A Novel Senotherapeutic Molecule For Skin Rejuvenation Therapies. OneSkin. Poster. Mar. 2019.

Buchholz et al., Year of birth determination using radiocarbon dating of dental enamel. Surface and Interface Analysis 42:398-401 (2009).

Bulterijs, S. et al., Phenotypic Screening in C. elegans as a Tool for the Discovery of New Geroprotective Drugs. Pharmaceuticals vol. 13 164 (2020).

CAS Database, Registry No. 56-81-5, 3 pages (2022).

Cell Signaling Technology: What is Senescence? 15 pages [retrieved online Aug. 16, 2022 at www.cellsignal.com/science-resources/overview-of-cellular-senescence ] (2022).

Cerda, E. et al., Geometry and physics of wrinkling. Phys. Rev. Lett. 90, 074302 (2003).

Cervoni, Olive Oil Nutrition Facts and Health Benefits. verywellfit.com. [Online] 2022. Available online at URL: www.verywellfit.com/olive-oil-nutrition-facts-calories-and-health-benefits-4120274? print. 8 pages.

Chainiaux, F. et al., UVB-induced premature senescence of human diploid skin fibroblasts. Int. J. Biochem. Cell Biol. 34, 1331-1339 (2002).

Chang et al., Clearance of senescent cells by ABT263 rejuvenates aged hematopoietic stem cells in mice. Nature Medicine. 22(1):78-83 (2016).

Chen et al., Discovery of cross-reactive probes and polymorphic CpGs in the Illumina Infinium HumanMethylation450 microarray. Epigenetics 8(2):203-209 (2013).

Chen et al., DNA methylation-based measures of biological age: meta-analysis predicting time to death. Aging 8(9):1844-1865 (2016).

Chen, W. et al., p53-related apoptosis resistance and tumor suppression activity in UVB-induced premature senescent human skin fibroblasts. Int. J. Mol. Med. 21, 645-653 (2008).

Chung, C. L. et al., Topical rapamycin reduces markers of senescence and aging in human skin: an exploratory, prospective, randomized trial. Geroscience 41, 861-869 (2019).

Cock et al., The Sanger FASTQ file format for sequences with quality scores, and the Solexa/Illumina FASTQ variants. Nucleic Acids Research 38(6):1767-1771 (2010).

Colman, R. J. et al., Caloric restriction reduces age-related and all-cause mortality in rhesus monkeys. Nat. Commun. 5, 3557 (2014).

Contet-Audonneau et al., A histological study of human wrinkle structures: comparison between sun-exposed areas of the face, with or without wrinkles, and sun-protected areas. British Journal of Dermatology vol. 140 1038-1047 (1999).

Coppé, J.-P. et al., Senescence-associated secretory phenotypes reveal cell-nonautonomous functions of oncogenic RAS and the p53 tumor suppressor. PLoS Biol. 6, 2853-2868 (2008).

Davis, T. et al., The role of cellular senescence in Werner syndrome: toward therapeutic intervention in human premature aging. Ann. N. Y. Acad. Sci. 1100, 455-469 (2007).

Debacq-Chainiaux, F. et al., Repeated exposure of human skin fibroblasts to UVB at subcytotoxic level triggers premature senescence through the TGF-beta1 signaling pathway. J. Cell Sci. 118, 743-758 (2005).

Debacq-Chainiaux, F. et al., UV, stress and aging. Dermatoendocrinol. 4, 236-240 (2012).

Del Marmol et al., Abundance and size of hyaluronan in naked mole-rat tissues and plasma. Sci Rep. 11(1):7951:1-21 doi:10.1038/s41598-021-86967-9 (2021).

Demaria, M., et al., Cell Autonomous and Non-Autonomous Effects of Senescent Cells in the Skin. J. Invest. Dermatol. 135, 1722-1726 (2015).

Demaria, M. et al., An essential role for senescent cells in optimal wound healing through secretion of PDGF-AA. Dev. Cell 31, 722-733 (2014).

Demidenko, Z. N. et al., Rapamycin decelerates cellular senescence. Cell Cycle 8, 1888-1895 (2009).

Dermaseptin 0.5%-20.65% Topical Ointment Dermatological Irritants-Counter-Irritant Formulations-Uses, Side Effects, and More. [Online] First available 2014. Available online at www.webmd.com/drugs/2/drug-155236/dermaseptin-topical/details#main-container. 3 pages.

Dimri, G. P. et al., A biomarker that identifies senescent human cells in culture and in aging skin in vivo. Proc. Natl. Acad. Sci. U. S. A. 92, 9363-9367 (1995).

Dobin et al., STAR: ultrafast universal RNA-seq aligner. Bioinformatics 29:15-21 (2013).

(56) References Cited

OTHER PUBLICATIONS

Doles, J. et al., Age-associated inflammation inhibits epidermal stem cell function. Genes Dev. 26, 2144-2153 (2012).
Ehrich et al., Quantitative high-throughput analysis of DNA methylation patterns by basic-specific cleavage and mass spectrometry. PNAS USA 102(44):15785-15790 (2005).
EP20844612.0 Extended European Search Report dated Aug. 29, 2023.
Farr, J. N. et al., Targeting cellular senescence prevents age-related bone loss in mice. Nat. Med. 23, 1072-1079 (2017).
Ferreira, R. et al., Advances and challenges in retinoid delivery systems in regenerative and therapeutic medicine. Nat. Commun. 11, 4265 (2020).
Fleischer, J. G. et al., Predicting age from the transcriptome of human dermal fibroblasts. Genome Biol. 19, 221 (2018).
Foyt et al., Identification of a novel senotherapeutic molecule: comparison with retinoic acid in human aged 2D and 3D skin models. Presentation. 6 pages. OneSkin. Jul. 2018.
Foyt et al., Novel senotherapeutic molecule discovery for skin rejuvenation using aging human 2-and 3-D skin equivalent models. OneSkin. Poster. Nov. 2018.
Fruman, D. A. et al., PI3K and cancer: lessons, challenges and opportunities. Nat. Rev. Drug Discov. 13, 140-156 (2014).
Fuhrmann-Stroissnigg, H. et al., Identification of HSP90 inhibitors as a novel class of senolytics. Nat. Commun. 8, 422 (2017).
Gorgoulis et al., Cellular senescence: defining a path forward. Cell 179:813-827 (2019).
Grether-Beck et al., Bioactive molecules from the Blue Lagoon: in vitro and in vivo assessment of silica mud and microalgae extracts for their effects on skin barrier function and prevention of skin ageing. Experimental Dermatology 17(9):771-779 (2008).
Hannum et al., Genome-wide methylation profiles reveal quantitative views of human aging rates. Molecular Cell 49(2):359-367 (2013).
Heyn et al., Aberrant DNA methylation profiles in the premature aging disorders Hutchinson-Gilford Progeria and Werner syndrome. Epigenetics 8(1):28-33 (2013).
Heyn et al., Distinct DNA methylomes of newborns and centenarians. PNAS USA 109(26):10522-10527 (2012).
Horvath et al., Accelerated epigenetic aging in Down syndrome. Aging Cell 14:491-495 (2015).
Horvath et al., An epigenetic clock analysis of race/ethnicity, sex, and coronary heart disease. Genome Biol. 17:171 [1-23] (2016).
Horvath et al., DNA methylation age of human tissues and cell types. Genome Biology 14(10):R115 (2013).
Horvath et al., Epigenetic clock for skin and blood cells applied to Hutchinson Gilford Progeria Syndrome and ex vivo studies. Aging 10(7):1758-1775 (2018).
Hudgins, A. D. et al., Age-and Tissue-Specific Expression of Senescence Biomarkers in Mice. Front. Genet. 9, 59 (2018).
Illumina, Infinium-Assay: Lab Setup and Procedure Guide, Document No. 11322460v3 (Research use only) [1-37] (May 2019).
Imhof, L. et al., Topical Over-the-Counter Antiaging Agents: An Update and Systematic Review. Dermatology 1-13 (2020).
International Cell Senescence Association (ICSA) Conference 2018, Cellular Senescence: Geroscience, Cancer and beyond, Montreal, Jul. 8-11, 2018. Program and Conference Information (2018). 100 pages.
Jacob, J. A., Men with HIV age faster according to DNA methylation study. JAMA 316:135-136 (2016).
Jaul, E. et al., Age-Related Diseases and Clinical and Public Health Implications for the 85 Years Old and Over Population. Front Public Health 5, 335 (2017).
Jobeili, L. et al., Selenium preserves keratinocyte stemness and delays senescence by maintaining epidermal adhesion. Aging 9, 2302-2315 (2017).
Kafi, R. et al., Improvement of naturally aged skin with vitamin A (retinol). Arch. Dermatol. 143, 606-612 (2007).
Karlin, Samuel et al., Applications and Statistics for Multiple High-scoring Segments in Molecular Sequences. Proceedings of the National Academy of Sciences of the United States of America vol. 90,12: pp. 5873-5877 (1993).
Karlin, Samuel, et al., Methods for Assessing the Statistical Significance of Molecular Sequence Features by Using General Scoring Schemes. Proceedings of the National Academy of Sciences of the United States of America 87(6):2264-2268 (1990).
Kent et al., BigWig and BigBed: enabling browsing of large distributed datasets. Bioinformatics 26(17):2204-2207 (2010).
Klughammer et al., Differential DNA methylation analysis without a reference genome. Cell Reports 13(11):2621-2633 (2015).
Koch et al., Monitoring of cellular senescence by DNA-methylation at specific CpG sites. Aging Cell 11(2):366-369 (2012).
Kovatcheva, M. et al., ATRX is a regulator of therapy induced senescence in human cells. Nat. Commun. 8, 386 (2017).
Kozlenkov et al., DNA methylation profiling of human prefrontal cortex neurons in heroin users show significant difference between genomic contexts of hyper-and hypomethylation and a younger epigenetic age. Genes (Basel) 8(6):152 [1-18] (2017).
Krishnamurthy, J. et al., Ink4a/Arf expression is a biomarker of aging. J. Clin. Invest. 114, 1299-1307 (2004).
Kruglikov, I. L. et al., Skin aging as a mechanical phenomenon: The main weak links. Nutr Healthy Aging 4, 291-307 (2018).
Lago, J. C. et al., The effect of aging in primary human dermal fibroblasts. PLoS One 14, e0219165 (2019).
Langevin et al., Peripheral blood DNA methylation profiles are indicative of head and neck squamous cell carcinoma. Epigenetics 7(3):291-299 (2012).
Lau, J. L. et al., Therapeutic peptides: Historical perspectives, current development trends, and future directions. Bioorg. Med. Chem. 26, 2700-2707 (2018).
Lawrence et al., Software for computing and annotating genomic ranges. PLoS Comput Biol. 9:8 e1003118 [1-10] (2013).
Lehninger et al., Principles of Biochemistry. pp. 793-800, Worth Publisher, New York (1982).
Levine et al., An epigenetic biomarker of aging for lifespan and healthspan. Aging 10(4):573-591 (2018).
Levine et al., DNA methylation age of blood predicts future onset of lung cancer in the women's health initiative. Aging 7(9):690-700 (2015).
Levine et al., Epigenetic age of the pre-frontal cortex is associated with neuritic plaques, amyloid load, and Alzheimer's disease related cognitive functioning. Aging 7(12):1198-1211 (2015).
Levine et al., Menopause accelerates biological aging. Proc Natl Acad Sci U S A. 113(33):9327-9332 (2016).
Li et al.: Basic science and cosmetic applications of bioactive polypeptide. China Surfactant Detergent& Cosmetics 32(5):41-43 [Machine Translated English Abstract] (2002).
Lippman et al., Profiling DNA methylation patterns using genomic tiling microarrays. Nat. Methods 2(3):219-224 (2005).
Liu, Y. et al., DNA damage responses in progeroid syndromes arise from defective maturation of prelamin A. J. Cell Sci. 119, 4644-4649 (2006).
Love, M. I. et al., Moderated estimation of fold change and dispersion for RNA-seq data with DESeq2. Genome Biol. 15, 550 (2014).
López-Otín, C. et al., The hallmarks of aging. Cell 153, 1194-1217 (2013).
Lu, A.T. et al., Genetic architecture of epigenetic and neuronal ageing rates in human brain regions. Nat Commun. 18:8:15353 (May 18, 2017).
Lu, A.T. et al., Genetic variants near MLST8 and DHX57 affect the epigenetic age of the cerebellum. Nat Commun. 2:7 DOI: 10.1038/ncomms10561 (2016).
Lu, A.T. et al., GWAS of epigenetic aging rates in blood reveals a critical role for TERT. Nat Commun. 26(9)387 (2018).
Lu et al., DNA methylation GrimAge strongly predicts lifespan and healthspan. Aging 11(2):303-327 (2019).
Maglioni, S. et al., Elegans screening strategies to identify pro-longevity interventions. Mechanisms of Ageing and Development vol. 157 60-69 (2016).

(56) References Cited

OTHER PUBLICATIONS

Maglioni, S. et al., An automated phenotype-based microscopy screen to identify pro-longevity interventions acting through mitochondria in C. elegans. Biochimica et Biophysica Acta (BBA)—Bioenergetics vol. 1847 1469-1478 (2015).

Malaspina et al., Depigmenting potential of lichen extracts evaluated by in vitro and in vivo tests. PeerJ. 8: e9150 (2020).

Marioni et al., Association of facial ageing with DNA methylation and epigenetic age predictions. Clinical Epigenetics 10(1):140 [1-3] (2018).

Marioni, R.E., et al. DNA methylation age of blood predicts all-cause mortality in later life. Genomic Biology 16(1):25 [1-12] (2015).

Matsuda et al., Melanogenesis Stimulation in Murine B16 Melanoma Cells by Piper nigrum Leaf Extract and its Lignan Constituents. Biol Pharm Bull 27(10): 1611-1616 (2004).

Matsuyama et al., Epigenetic clock analysis of human fibroblasts in vitro: effects of hypoxia, donor age, and expression of hTERT and SV40 largeT. Aging 11(10):3012-3022 (2019).

McCart, E. A. et al., Accelerated senescence in skin in a murine model of radiation-induced multi-organ injury. Journal of Radiation Research vol. 58 636-646 (2017).

McCook et al., Ability of sodium copper chlorophyllin complex to repair photoaged skin by stimulation of biomarkers in human extracellular matrix. Clinical, Cosmetic and Investigational Dermatology 9:167-174 (2016).

McHugh et al., Senescence and aging: Causes, consequences, and therapeutic avenues. J. Cell Biol. 217:65-77 (2018).

Mukherjee, S. et al., Retinoids in the treatment of skin aging: an overview of clinical efficacy and safety. Clin. Interv. Aging 1, 327-348 (2006).

Muñoz-Espín, D. et al., Programmed cell senescence during mammalian embryonic development. Cell 155, 1104-1118 (2013).

Natsuga, K., Epidermal barriers. Cold Spring Harb. Perspect. Med. 4, a018218 (2014).

Netmeds: Clove Oil: Discover About the Astonishing Wellness Benefits of this Essential Emollient—Infographic. 4 pages [retrieved online Aug. 31, 2022 at https://www.netmeds.com/health-library/post/clove-oil-discover-about-the-astonishing-wellness-benefits-of-this-essential-emollient-infographic ] (2021).

Niedernhofer et al., Senotherapeutics for healthy ageing. Nature Reviews—Drug Discovery 17:377 [1-3] (2018).

Ocampo, A. et al., In Vivo Amelioration of Age-Associated Hallmarks by Partial Reprogramming. Cell vol. 167 1719-1733.e12 (2016).

Olek et al., The pre-implantation ontogeny of the H19 methylation imprint. Nature Genetics 17(3):275-276 (1997).

Oliveira. OneSkin: The science of staying young while you grow older. Presentation. 23 pages. 2019.

OneSkin. The science of staying young while you grow older. Poster. Jan. 2019.

Pal et al., Epigenetics and aging. Sci Adv. 2(7):e1600584 [1-19] (2016).

Park et al., Epigenetics: linking nutrition to molecular mechanisms in aging. Prev. Nutr. Food Sci. 22(2):81-89 (2017).

Parrado et al., Environmental stressors on skin aging. Mechanistic insights. Front. Pharmacol. 10:759 [1-17] (2019).

PCT/US2018/051244 International Preliminary Report on Patentability dated Mar. 26, 2020.

PCT/US2018/051244 International Search Report and Written Opinion dated Apr. 23, 2019.

PCT/US2020/043033 International Search Report and Written Opinion dated Jan. 19, 2021.

Pennacchi, P. C. et al. Glycated Reconstructed Human Skin as a Platform to Study the Pathogenesis of Skin Aging. Tissue Eng. Part A 21, 2417-2425 (2015).

Pidsley, R. et al., A data-driven approach to preprocessing Illumina 450K methylation array data. BMC Genomics 14, 293 (2013).

Porto, W. F. et al., In silico optimization of a guava antimicrobial peptide enables combinatorial exploration for peptide design. Nat. Commun. 9, 1490 (2018).

Porto, W. F. et al., An algorithm to insert patterns into sequences for designing antimicrobial peptides. Biochim. Biophys. Acta Gen. Subj. 1862, 2043-2052 (2018).

Quach et al., Epigenetic clock analysis of diet, exercise, education, and lifestyle factors. Aging 9(2):419-446 (2017).

Quan, T. et al., Elevated matrix metalloproteinases and collagen fragmentation in photodamaged human skin: impact of altered extracellular matrix microenvironment on dermal fibroblast function. J. Invest. Dermatol. 133, 1362-1366 (2013).

Rahman, M. et al., NemaLife chip: a micropillar-based microfluidic culture device optimized for aging studies in crawling C. elegans. Sci. Rep. 10, 16190 (2020).

Ramos-E-Silva, M. et al., Anti-aging cosmetics: facts and controversies. Clin. Dermatol. 31, 750-758 (2013).

Rayess, H. et al., Cellular senescence and tumor suppressor gene p16. Int. J. Cancer 130, 1715-1725 (2012).

Rein et al., Identifying 5-methylcytosine and related modifications in DNA genomes. Nucleic Acids Res. 26(10):2255-2264 (1998).

Ressler S. et al., p16INK4A is a robust in vivo biomarker of cellular aging in human skin. Aging Cell vol. 5 379-389 (2006).

Riahi, R. et al., Topical Retinoids: Therapeutic Mechanisms in the Treatment of Photodamaged Skin. Am. J. Clin. Dermatol. 17, 265-276 (2016).

Roos et al., Higher nevus count exhibits a distinct DNA methylation signature in healthy human skin: implications for melanoma. Jour. Inv Derma. 137:910-920 (2017)—Dataset GSE90124.

Roos et al., Source for Dataset GSE90124 cited in Higher Nevus Count Exhibits a Distinct DNA Methylation Signature in Healthy Human Skin: Implications for Melanoma, Jour. Inv Derma. 137 (2017); downloaded from ittps://www.ncbi.nlm.nih.gov/geo/query/acc.cgi?acc=GSE90124 on Apr. 6, 2020 [1-2].

Rotzschke et al., Superactivation of an immune response triggered by oligomerized T cell epitopes. Proc Natl Acad Sci U S A. Dec. 23, 1997;94(26):14642-7.

Sandoval et al., Validation of a DNA methylation microarray for 450,000 CpG sites in the human genome. Epigenetics 6(6):692-702 (2011).

Schadendorf et al., Retinoic Acid receptor-gamma-selective retinoids exert antiproliferative effects on human-melanoma cell-growth in-vitro. Int J Oncol 5(6):1325-1331 (1994).

Shao, Y. et al., Molecular basis of retinol anti-ageing properties in naturally aged human skin in vivo. Int. J. Cosmet. Sci. 39, 56-65 (2017).

Shin, J. et al., Repeated exposure of human fibroblasts to UVR induces secretion of stem cell factor and senescence. J. Eur. Acad. Dermatol. Venereol. 26, 1577-1580 (2012).

Smith et al., Illuminaio: an open source IDAT parsing tool for Illumina microarrays [version 1; peer review: 2 approved] F1000Research 2:264 [1-8] (2013).

Soroka et al., Aged keratinocyte phenotyping: Morphology, biochemical markers and effects of Dead Sea minerals. Experimental Gerontology 43(10):947-957 (2008).

Sturm et al., Human aging DNA methylation signatures are conserved but accelerated in cultured fibroblasts. Epigenetics 14:961-976 (2019).

Takahashi, K. et al., Induction of Pluripotent Stem Cells from Adult Human Fibroblasts by Defined Factors. Cell 131, 861-872 (2007).

Takahashi, Kazutoshi, et al., Induction of Pluripotent Stem Cells from Mouse Embryonic and Adult Fibroblast Cultures by Defined Factors. Cell 126(4):663-676 (2006).

Tchkonia, T., et al., Cellular senescence and the senescent secretory phenotype: therapeutic opportunities. J. Clin. Invest. 123, 966-972 (2013).

The Lusis laboratory UCLA: Analysis of mouse plasma lipids, lipoproteins and apolipoproteins. 20 pages [retrieved online Aug. 16, 2022 at https://lusis.genetics.ucla.edu/protocols/mouse_lipid_analysis ] (2022).

Thompson et al., An overview of DNA typing methods for human identification: past, present, and future. Methods Mol Biol. 830:3-16 (2012).

(56) References Cited

OTHER PUBLICATIONS

Tobin D.J., Introduction to skin aging. J. Tissue Viability 26:37-46 (2017).
Toutfaire, M. et al., The impact of cellular senescence in skin ageing: A notion of mosaic and therapeutic strategies. Biochem. Pharmacol. 142, 1-12 (2017).
Towers, C. G. et al., Autophagy-dependent cancer cells circumvent loss of the upstream regulator RB1CC1/FIP200 and loss of LC3 conjugation by similar mechanisms. Autophagy 16, 1332-1340 (2020).
Törmä, H., Regulation of keratin expression by retinoids. Dermatoendocrinol. 3, 136-140 (2011).
Tse et al., ABT-263: A Potent and Orally Bioavailable Bcl-2 Family Inhibitor. Cancer Res 68(9):3421-3428 (2008).
UniProt Database, Accession No. Q9JLA7, 1 page (2000).
UniProt submission A0A259MX01_9PROT, Rhodospirillales bacterium 39-66-50 uncharacterized protein (2017).
UniProt submission A0A2T4VLY6_9DELT, *Vitiosangium* sp. GDMCC 1.1324 Peroxidase (2018).
U.S. Appl. No. 16/132,297 Final Office Action mailed Sep. 7, 2021.
U.S. Appl. No. 16/936,177 Final Office Action dated Jan. 12, 2023.
U.S. Appl. No. 16/936,177 Non-Final Office Action dated Aug. 17, 2023.
U.S. Appl. No. 16/936,177 Non-Final Office Action dated Aug. 24, 2022.
U.S. Appl. No. 16/132,297 Office Action dated Jan. 21, 2021.
U.S. Appl. No. 16/936,177 Office Action dated Jan. 16, 2024.
Van Oorschot et al., Forensic trace DNA: a review. Investigative Genetics 1(14):1-17 (2010).
Vandiver et al., Age and sun exposure-related widespread genomic blocks of hypomethylation in nonmalignant skin. Genome Biology 16:80 [1-15] (2015).
Vandiver et al., Source for Dataset GSE51954 cited in Age and sun exposure-related widespread genomic blocks pf hypomethylation in nonmalignant skin, Genome Biology, 16:80 (Apr. 2015); downloaded from https://www.ncbi.nlm.nih.gov/geo/query/acc.cgi?acc=GSE51954 on Apr. 6, 2020.
Varley, K.E. et al., Bisulfite Patch PCR enables multiplexed sequencing of promoter methylation across cancer samples. Genome Research 20:1279-1287 (2010).
Ventura, E. et al., RBL2/p130: a direct AKT substrate and mediator of AKT inhibition-induced apoptosis. Oncoscience 5, 278-280 (2018).
Waaijer, M. E. C. et al., P16INK4a Positive Cells in Human Skin Are Indicative of Local Elastic Fiber Morphology, Facial Wrinkling, and Perceived Age. J. Gerontol. A Biol. Sci. Med. Sci. 71, 1022-1028 (2016).
Waaijer, M. E. C. et al., The number of p16INK4a positive cells in human skin reflects biological age. Aging Cell 11, 722-725 (2012).
Wang, A. S. et al., Biomarkers of Cellular Senescence and Skin Aging. Front. Genet. 9, 247 (2018).
Wang, A. S. et al., Loss of lamin B1 is a biomarker to quantify cellular senescence in photoaged skin. Sci. Rep. 7, 15678 (2017).
Wang, J. et al., Deletion of Nrip1 Extends Female Mice Longevity, Increases Autophagy, and Delays Cell Senescence. J. Gerontol. A Biol. Sci. Med. Sci. 73, 882-892 (2018).
Wang, R. et al., Rapamycin inhibits the secretory phenotype of senescent cells by a Nrf2-independent mechanism. Aging Cell 16, 564-574 (2017).
Watson, R. E. B. et al., Repair of photoaged dermal matrix by topical application of a cosmetic 'antiageing' product. British Journal of Dermatology vol. 158 472-477 (2007).
Webb, A. E., et al., Characterization of the direct targets of FOXO transcription factors throughout evolution. Aging Cell 15, 673-685 (2016).
Wedel, S. et al., tBHP treatment as a model for cellular senescence and pollution-induced skin aging. Mech. Ageing Dev. 190, 111318 (2020).
Wilson et al., Safety, Pharmacokinetics, Pharmacodynamics, and Activity of Navitoclax, a Targeted High Affinity Inhibitor of BCL-2, in Lymphoid Malignancies. Lancet Oncol. 11(12):1149-1159 (2010).
Wootton, John et al., Statistics of local complexity in amino acid sequences and sequence databases. Computers & Chemistry 17(2):149-163 (1993).
Wu et al., Antioxidants add protection to a broad-spectrum sunscreen. Clinical and Experimental Dermatology 36(2):178-187 (2011).
Wulfridge et al., Choice of reference genome can introduce massive bias in bisulfite sequencing data. BioRxiv [1-31] doi: https://doi.org/10.1101/076844 (2016).
Xie et al., DNA methylation patterns separate senescence from transformation potential and indicate cancer risk. Cancer Cell 33:309-321.e5 (2018).
Xu, M. et al., Senolytics improve physical function and increase lifespan in old age. Nat. Med. 24, 1246-1256 (2018).
Yang, G.-Y. et al., Effects of cigarette smoke extracts on the growth and senescence of skin fibroblasts in vitro. Int. J. Biol. Sci. 9, 613-623 (2013).
Ye, L. et al., Topical applications of an emollient reduce circulating pro-inflammatory cytokine levels in chronically aged humans: a pilot clinical study. J. Eur. Acad. Dermatol. Venereol. 33, 2197-2201 (2019).
Yoo, B. S. et al., Regulation of proteins related to melanogenesis by heartwood extract of Morus bombycis using proteome analysis. Biotechnology and Bioprocess Engineering 12(6):662-667 (2007).
Yu et al., Reference materials for calibration of analytical biases in quantification of DNA methylation. PLoS One 10(9):e0137006 [1-12] (2015).
Zhu, Y., Armstrong et al., Cellular senescence and the senescent secretory phenotype in age-related chronic diseases. Current Opinion in Clinical Nutrition and Metabolic Care vol. 17 324-328 (2014).
Zonari, A. et al., Poly(hydroxybutyrate-co-hydroxyvalerate) bilayer skin tissue engineering constructs with improved epidermal rearrangement. Macromol. Biosci. 14, 977-990 (2014).
Zonari, Quem Quer Viver Para Sempre? SingularityU Brazil Summit. OneSkin. Presentation. 26 pages. (Jun. 2019).
Levast, Benoit et al. Vaccine Potentiation by Combination Adjuvants. Vaccines 2:297-322 (2014).
U.S. Appl. No. 16/936,177 Office Action dated Aug. 6, 2024.

\* cited by examiner

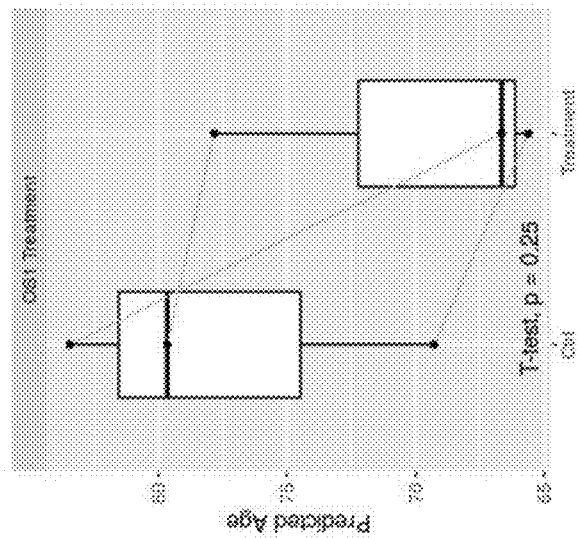
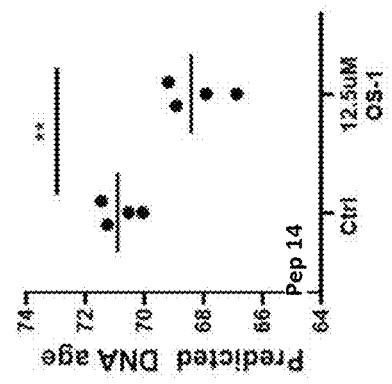
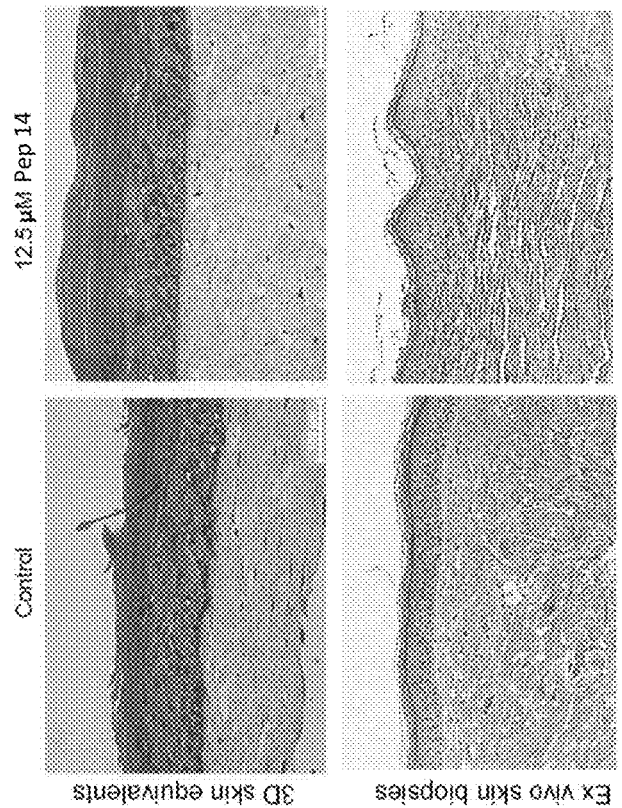
FIG. 11B
FIG. 11C
FIG. 11A

```
                           SEQUENCE LISTING

Sequence total quantity: 34
SEQ ID NO: 1            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 1
ETAKHWLKGI                                                                        10

SEQ ID NO: 2            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 2
ATAKAWLKGI                                                                        10

SEQ ID NO: 3            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 3
KLKGILRGAA                                                                        10

SEQ ID NO: 4            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 4
WLKGILREAA                                                                        10

SEQ ID NO: 5            moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 5
LKGI                                                                               4

SEQ ID NO: 6            moltype = AA  length = 5
FEATURE                 Location/Qualifiers
```

```
REGION                  1..5
                        note = Description of Artificial Sequence: Synthetic peptide
source                  1..5
                        mol_type = protein
                        organism = synthetic construct
SEQUENCE: 6
LKGIL                                                                             5

SEQ ID NO: 7            moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 7
WLKGI                                                                             5

SEQ ID NO: 8            moltype = AA  length = 10
FEATURE                 Location/Qualifiers
REGION                  1..10
                        note = Description of Artificial Sequence: Synthetic peptide
MOD_RES                 3
                        note = Any amino acid except Ser
MOD_RES                 5
                        note = Any amino acid
MOD_RES                 8
                        note = Any amino acid
REGION                  1..10
                        note = See specification as filed for detailed description
                         of substitutions and preferred embodiments
source                  1..10
                        mol_type = protein
                        organism = synthetic construct
SEQUENCE: 8
ETXKXWLXGI                                                                       10

SEQ ID NO: 9            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 9
STAKAWLKGI                                                                       10

SEQ ID NO: 10           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 10
ETAKAWEKGI                                                                       10

SEQ ID NO: 11           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 11
ETAKAWHKGI                                                                       10

SEQ ID NO: 12           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 12
ETAKAWLKSI                                                                       10

SEQ ID NO: 13           moltype = AA  length = 10
FEATURE                 Location/Qualifiers
```

```
REGION                   1..10
                         note = Description of Artificial Sequence: Synthetic peptide
source                   1..10
                         mol_type = protein
                         organism = synthetic construct
SEQUENCE: 13
ETAKAWLKGE                                                              10

SEQ ID NO: 14            moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 14
ETAKAWLKGI                                                              10

SEQ ID NO: 15            moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 15
WLKGILRGAA                                                              10

SEQ ID NO: 16            moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 16
KTAKAWLKGI                                                              10

SEQ ID NO: 17            moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 17
NTAKAWLKGI                                                              10

SEQ ID NO: 18            moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 18
PTAKAWLKGI                                                              10

SEQ ID NO: 19            moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 19
QTAKAWLKGI                                                              10

SEQ ID NO: 20            moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 20
EQAKAWLKGI                                                              10

SEQ ID NO: 21            moltype = AA   length = 10
```

-continued

| | |
|---|---|
| FEATURE | Location/Qualifiers |
| REGION | 1..10 |
| | note = Description of Artificial Sequence: Synthetic peptide |
| source | 1..10 |
| | mol_type = protein |
| | organism = synthetic construct |
| SEQUENCE: 21 | |
| WLKGICRGAA | 10 |
| | |
| SEQ ID NO: 22 | moltype = AA  length = 10 |
| FEATURE | Location/Qualifiers |
| REGION | 1..10 |
| | note = Description of Artificial Sequence: Synthetic peptide |
| source | 1..10 |
| | mol_type = protein |
| | organism = synthetic construct |
| SEQUENCE: 22 | |
| WLKGILPGAA | 10 |
| | |
| SEQ ID NO: 23 | moltype = AA  length = 10 |
| FEATURE | Location/Qualifiers |
| REGION | 1..10 |
| | note = Description of Artificial Sequence: Synthetic peptide |
| source | 1..10 |
| | mol_type = protein |
| | organism = synthetic construct |
| SEQUENCE: 23 | |
| WLKGILQGAA | 10 |
| | |
| SEQ ID NO: 24 | moltype = AA  length = 10 |
| FEATURE | Location/Qualifiers |
| REGION | 1..10 |
| | note = Description of Artificial Sequence: Synthetic peptide |
| source | 1..10 |
| | mol_type = protein |
| | organism = synthetic construct |
| SEQUENCE: 24 | |
| WLKGILSGAA | 10 |
| | |
| SEQ ID NO: 25 | moltype = AA  length = 10 |
| FEATURE | Location/Qualifiers |
| REGION | 1..10 |
| | note = Description of Artificial Sequence: Synthetic peptide |
| source | 1..10 |
| | mol_type = protein |
| | organism = synthetic construct |
| SEQUENCE: 25 | |
| WLKGILVGAA | 10 |
| | |
| SEQ ID NO: 26 | moltype = AA  length = 10 |
| FEATURE | Location/Qualifiers |
| REGION | 1..10 |
| | note = Description of Artificial Sequence: Synthetic peptide |
| source | 1..10 |
| | mol_type = protein |
| | organism = synthetic construct |
| SEQUENCE: 26 | |
| WLKGILRAAA | 10 |
| | |
| SEQ ID NO: 27 | moltype = AA  length = 10 |
| FEATURE | Location/Qualifiers |
| REGION | 1..10 |
| | note = Description of Artificial Sequence: Synthetic peptide |
| source | 1..10 |
| | mol_type = protein |
| | organism = synthetic construct |
| SEQUENCE: 27 | |
| WLKGILRGHA | 10 |
| | |
| SEQ ID NO: 28 | moltype = AA  length = 10 |
| FEATURE | Location/Qualifiers |
| REGION | 1..10 |
| | note = Description of Artificial Sequence: Synthetic peptide |
| source | 1..10 |
| | mol_type = protein |
| | organism = synthetic construct |
| SEQUENCE: 28 | |
| WLKGILRGIA | 10 |

| | |
|---|---|
| SEQ ID NO: 29<br>FEATURE<br>REGION<br><br>MOD_RES<br><br>MOD_RES<br><br>MOD_RES<br><br>REGION<br><br><br>source<br><br><br>SEQUENCE: 29<br>ETXKXWLXGI | moltype = AA  length = 10<br>Location/Qualifiers<br>1..10<br>note = Description of Artificial Sequence: Synthetic peptide<br>3<br>note = Any amino acid<br>5<br>note = Any amino acid<br>8<br>note = Any amino acid except Gly<br>1..10<br>note = See specification as filed for detailed description<br> of substitutions and preferred embodiments<br>1..10<br>mol_type = protein<br>organism = synthetic construct<br><br>                                                                      10 |
| SEQ ID NO: 30<br>FEATURE<br>REGION<br><br>MOD_RES<br><br>MOD_RES<br><br>MOD_RES<br><br>REGION<br><br><br>source<br><br><br>SEQUENCE: 30<br>ETXKXWLXGI | moltype = AA  length = 10<br>Location/Qualifiers<br>1..10<br>note = Description of Artificial Sequence: Synthetic peptide<br>3<br>note = Any amino acid<br>5<br>note = Any amino acid except Asn<br>8<br>note = Any amino acid<br>1..10<br>note = See specification as filed for detailed description<br> of substitutions and preferred embodiments<br>1..10<br>mol_type = protein<br>organism = synthetic construct<br><br>                                                                      10 |
| SEQ ID NO: 31<br>FEATURE<br>REGION<br><br>MOD_RES<br><br>MOD_RES<br><br>MOD_RES<br><br>MOD_RES<br><br>REGION<br><br><br>source<br><br><br>SEQUENCE: 31<br>KLXXILXGXA | moltype = AA  length = 10<br>Location/Qualifiers<br>1..10<br>note = Description of Artificial Sequence: Synthetic peptide<br>3<br>note = Any amino acid except Asn<br>4<br>note = Any amino acid<br>7<br>note = Any amino acid<br>9<br>note = Any amino acid<br>1..10<br>note = See specification as filed for detailed description<br> of substitutions and preferred embodiments<br>1..10<br>mol_type = protein<br>organism = synthetic construct<br><br>                                                                      10 |
| SEQ ID NO: 32<br>FEATURE<br>REGION<br><br>MOD_RES<br><br>MOD_RES<br><br>MOD_RES<br><br>MOD_RES<br><br>REGION<br><br><br>source<br><br><br>SEQUENCE: 32<br>KLXXILXGXA | moltype = AA  length = 10<br>Location/Qualifiers<br>1..10<br>note = Description of Artificial Sequence: Synthetic peptide<br>3<br>note = Any amino acid<br>4<br>note = Any amino acid<br>7<br>note = Any amino acid<br>9<br>note = Any amino acid except Ser<br>1..10<br>note = See specification as filed for detailed description<br> of substitutions and preferred embodiments<br>1..10<br>mol_type = protein<br>organism = synthetic construct<br><br>                                                                      10 |

```
SEQ ID NO: 33          moltype = AA  length = 10
FEATURE                Location/Qualifiers
REGION                 1..10
                       note = Description of Artificial Sequence: Synthetic peptide
MOD_RES                3
                       note = Any amino acid
MOD_RES                4
                       note = Any amino acid
MOD_RES                7
                       note = Any amino acid except Leu
MOD_RES                9
                       note = Any amino acid
REGION                 1..10
                       note = See specification as filed for detailed description
                        of substitutions and preferred embodiments
source                 1..10
                       mol_type = protein
                       organism = synthetic construct
SEQUENCE: 33
KLXXILXGXA                                                                        10

SEQ ID NO: 34          moltype = AA  length = 10
FEATURE                Location/Qualifiers
REGION                 1..10
                       note = Description of Artificial Sequence: Synthetic peptide
MOD_RES                3
                       note = Any amino acid
MOD_RES                4
                       note = Any amino acid except Ser
MOD_RES                7
                       note = Any amino acid
MOD_RES                9
                       note = Any amino acid
REGION                 1..10
                       note = See specification as filed for detailed description
                        of substitutions and preferred embodiments
source                 1..10
                       mol_type = protein
                       organism = synthetic construct
SEQUENCE: 34
KLXXILXGXA                                                                        10
```

POLYPEPTIDES HAVING ANTI-SENESCENT EFFECTS AND USES THEREOF

CROSS REFERENCE

This application is a divisional of U.S. application Ser. No. 16/936,177, filed Jul. 22, 2020, which claims the benefit of U.S. Provisional Patent Application No. 62/877,164, filed Jul. 22, 2019, each of which are entirely incorporated herein by reference.

SEQUENCE LISTING

The instant application contains a Sequence Listing which has been submitted electronically in XML format and is hereby incorporated by reference in its entirety. Said XML copy, created on May 24, 2024, is named 56292-701_301-SL.xml and is 56,937 bytes in size.

BACKGROUND

Accumulation of cellular senescence is not only a product of organism aging, it can also actively contribute to further senescence induction in a positive feedback cycle. Among the hallmarks of aging, cellular senescence may occupy a central position, integrating primary, antagonistic and integrative aspects of aging. First, senescence can compromise tissue-repair and renewal capacity of the affected tissue, since it decreases proliferation capacity of progenitor cells. Second, senescent cells can alter the paracrine signaling milieu, being characterized by their senescence-associated secretory phenotype (SASP), which can induce inflammation and further cellular senescence, possibly exacerbating a potentially deleterious inflammatory response and possibly promoting tissue injury. Third, the accumulation of senescent cells with age has been documented in several tissues, including, but not limited to, the skin. Fourth, cellular senescence can be an active player in diseases, such as macular degeneration, dementia, atherosclerosis and cancer.

Senescent cells can be identified by Senescence-Associated beta-galactosidase (SA-BGal) production, p16 expression, and alpha thalassemia/mental retardation X-linked chromatin remodeling protein (ATRX) foci accumulation in the nuclei. Functional alterations also distinguish senescent cells, including decreased proliferation capacity and resistance to mitogenic stimuli.

SUMMARY

Described herein are compositions comprising an isolated, synthetic, and/or recombinant polypeptide comprising an amino acid sequence of LKGI (SEQ ID NO: 5) or analogs thereof, an amino acid sequence of LKGIL (SEQ ID NO: 6) or analogs thereof, or an amino acid sequence of WLKGI (SEQ ID NO: 7) or analogs thereof. In some embodiments, such polypeptide can comprise at least 4, 5, 6, 7, 8, 9, 10, 11, 12, 13, 14, 15, 16, 17, 18, 19, 20, 21, 22, 23, 24, 25, 26, 27, 28, 29, 30, 35, or 40 amino acids. Alternatively or additionally, such polypeptide comprises at most 100, 90, 80, 70, 60, 50, 40, 35, 30, 25, or 20 amino acids. In some instances, the polypeptide has at least 70%, 75%, 80%, 85%, 90%, 95%, 96%, 97%, 98%, or 99% sequence identity to any of SEQ ID NO:1-4.

Also described herein are isolated, synthetic and/or recombinant polypeptides comprising an amino acid sequence of SEQ ID NO:8, which is represented by $X_1X_2X_3X_4X_5X_6X_7X_8X_9X_{10}$ or an analog thereof 1. wherein $X_1$ is E, $X_2$ is T, $X_4$ is K, $X_6$ is W, $X_7$ is L, $X_9$ is G, and $X_{10}$ is I; and (i) $X_3$ is not S (SEQ ID NO: 8); or
2. (ii) if $X_5$ is any amino acid then $X_8$ is not G (SEQ ID NO: 29); or
3. (iii) if $X_8$ is any amino acid then $X_5$ is not N (SEQ ID NO: 30);
4. or (iv) any one of (i), (ii), or (iii) optionally with 1, 2, 3, or 4 conservative amino acid substitutions; or
5. (b) the amino acid sequence has at least 70%, 80%, 85%, 90%, or 95% identity to a second sequence SEQ ID NO:2 wherein $X_1$ is A, $X_2$ is T, $X_3$ is A, $X_4$ is K, $X_5$ is A, $X_6$ is W, $X_7$ is L, $X_8$ is K, $X_9$ is G, and $X_{10}$ is I, optionally with 1, 2, 3, or 4 conservative amino acid substitutions; or (c) the amino acid sequence has at least 70%, 80%, 85%, 90%, or 95% identity to a third sequence SEQ ID NO:3 wherein $X_1$ is K, $X_2$ is L, $X_5$ is I, $X_6$ is L, $X_8$ is G, and $X_{10}$ is A; and (i) if $X_9$ is any amino acid then $X_3$ is not N (SEQ ID NO: 31); or (ii) if $X_3$ is any amino acid then $X_9$ is not S (SEQ ID NO: 32); or (iii) if $X_4$ is any amino acid then $X_7$ is not L (SEQ ID NO: 33); or (iv) if $X_7$ is any amino acid then $X_4$ is not S (SEQ ID NO: 34), and; or (v) any one of (i), (ii), (iii), or (iv) optionally with 1, 2, 3, or 4 conservative amino acid substitutions; or (d) the amino acid sequence has at least 70%, 80%, 85%, 90%, or 95% identity to a fourth sequence SEQ ID NO:4 wherein $X_1$ is W, $X_2$ is L, $X_3$ is K, $X_4$ is G, $X_5$ is I, $X_6$ is L, $X_7$ is R, $X_8$ is E, $X_9$ is A, and $X_{10}$ is A, optionally with 1, 2, 3, or 4 conservative amino acid substitutions.

In some embodiments, the amino acid sequence comprises LKGI (SEQ ID NO:5). In some embodiments, the amino acid sequence comprises WLKGI (SEQ ID NO:7). In some embodiments, the amino acid sequence comprises LKGIL (SEQ ID NO:6). In some embodiments, the amino acid sequence has at least 70%, 80%, 85%, 90%, or 95% identity to a sequence of SEQ ID NO:1. In some embodiments, the amino acid sequence is SEQ ID NO:1. In some embodiments, the amino acid sequence is SEQ ID NO:2. In some embodiments, the amino acid sequence has at least 70%, 80%, 85%, 90%, or 95% identity to a sequence of SEQ ID NO:3. In some embodiments, the amino acid sequence is SEQ ID NO:3. In some embodiments, the amino acid sequence is SEQ ID NO:4. In some embodiments, the recombinant polypeptide comprises at least 10 amino acids, 15 amino acids, or 20 amino acids.

The compositions provided herein can be formulated for use as a therapeutic, nutraceutical, or cosmetic.

In some embodiments, the formulation further comprises a therapeutic, nutraceutical, or cosmetic excipient. In some embodiments, the excipient is configured for topical application. In some embodiments, the excipient is configured as a topical supplement. In further embodiments, the formulation is configured for application to human skin. In some embodiments, the formulation is a cream, a transdermal patch, a topical patch, an ointment, an oil, a gel, a liquid, a powder, a lotion, a serum, an emulsion, a moisturizer, a toner, a foam, a face mask, a mousse, an aerosol, a spray, a cleanser, a hydrogel patch, a powder, or a shampoo. In some embodiments, the formulation may be used in conjunction with a sonic treatment, an ultrasonic treatment, a LED treatment, a light treatment, an electrical treatment, or a radiofrequency treatment. In some embodiments, the transdermal patch delivers the formulation to the epidermal layer of the skin. In some embodiments, the transdermal patch delivers the formulation to the epidermal and dermal layers of the skin. In some embodiments, the formulation is delivered in minimum or low amounts systemically in the subject or is not intended to be delivered directly into the bloodstream of the subject. In some embodiments, the formulation acts locally at and near the delivery site. In some embodiments, the formulation has minimal to no effects systemically.

In some embodiments, the formulation is configured as an edible supplement. In some cases, the formulation is configured as a beverage.

Described herein are therapeutic, nutraceutical, or cosmetic formulations comprising at least one recombinant or synthetic polypeptide herein and a therapeutic, nutraceutical, or cosmetic excipient.

In some embodiments, the excipient is configured for topical application. In some embodiments, the excipient is configured as a topical supplement. In further embodiments, the formulation is formulated for application to human skin. More specifically, the formulation can be configured to penetrate topically from the epidermis to the dermis. In some embodiments, the formulation can be configured to penetrate topically through the epidermis and dermis layers. In some embodiments, the formulation can be configured to penetrate topically through the epidermis layer and have low penetration into the dermis layer. Often, the penetration of a component in a formulation may be assessed using various permeation studies, including but not limited to those using a Franz diffusion cell. In some embodiments, the formulation comprises a carrier, a microsphere, a liposome, or a micelle in order to carry the polypeptide and control the release time and/or penetration depth of the polypeptide through the skin. In some cases, a formulation herein is a cream, an ointment, a gel, a liquid, an oil, a powder, a lotion, a serum, an emulsion, a moisturizer, a foam, a face mask, a mousse, an aerosol, a spray, a cleanser, a toner, a topical patch, a hydrogel patch, or a shampoo.

In some embodiments, the formulation is configured as an edible supplement. In some embodiments, the formulation is configured as a beverage. In some embodiments, the formulation is configured as a tablet, a capsule, a gel, a gummy, or a powder.

Described herein are methods of treating a condition in a subject in need thereof, the method comprising administering to the subject a therapeutic, nutraceutical, or cosmetic formulation comprising an amino acid sequence of at least one of SEQ ID NOS:5-7.

In some embodiments, the administering comprises topically applying the formulation to the subject. In further embodiments, the subject is a human or other animal. In some embodiments, the method comprises administering an effective amount of the formulation to the subject.

In some embodiments, the condition is a disorder associated with accumulation of senescent cells in the subject. In some embodiments, the disorder associated with accumulation of senescent cells comprises aging skin. In some embodiments, the condition is a disorder associated with progeria and/or an effect of progeria. In some embodiments, progeria comprises conditions having premature aging symptoms in the epidermal and dermal layers of skin.

Described herein are methods of reducing cellular senescence in a subject in need thereof, the method comprising administering to the subject a therapeutic, nutraceutical, or cosmetic formulation comprising a polypeptide comprising an amino acid sequence of LKGI (SEQ ID NO:5) optionally with 1 conservative amino acid substitution.

In some embodiments, the polypeptide comprises at least 4 amino acids, 10 amino acids, 15 amino acids, or 20 amino acids. In some embodiments, the formulation comprises an amino acid sequence of WLKGI (SEQ ID NO:7) optionally with 1 conservative amino acid substitution. In some embodiments, the formulation comprises an amino acid sequence of LKGIL (SEQ ID NO:6) optionally with 1 conservative amino acid substitution. In some embodiments, the polypeptide comprises at least 5 amino acids, 10 amino acids, 15 amino acids, or 20 amino acids. In some embodiments, the polypeptide comprises no more than 10 amino acids, 15 amino acids, 20 amino acids, 25 amino acids, 30 amino acids, 35 amino acids, or 40 amino acids.

In some embodiments, the formulation further comprises a therapeutic, nutraceutical, or cosmetic excipient.

Described herein are methods of reducing cellular senescence in a subject in need thereof, the method comprising administering to the subject a therapeutic, nutraceutical, or cosmetic formulation comprising at least one polypeptide described herein.

In some embodiments, the formulation further comprises a therapeutic, nutraceutical, or cosmetic excipient. In some embodiments, the administering comprises applying the formulation to a portion of the skin of the subject. In some embodiments, the formulation extends a lifespan of a plurality of cells of the subject, induces SIRT6 expression in a plurality of cells of the subject, increases cell renewal rates in a plurality of cells of the subject, promotes apoptosis in a plurality of cells of the subject, promotes DNA repair in a plurality of cells of the subject, increases collagen production in a plurality of cells of the subject, increases hyaluronic synthase production in a plurality of cells of the subject, decreases ATRX nuclear foci accumulation in a plurality of cells of the subject, decreases p16 expression in a plurality of cells of the subject, decreases senescence associated beta-galactosidase production in a plurality of cells of the subject, decreases IL8 expression in a plurality of cells of the subject, decreases MMP1 expression in a plurality of cells of the subject, increases BLM expression in a plurality of cells of the subject, and/or prevents UV-induced DNA damage in a plurality of cells of the subject.

Described herein are methods of treating a condition in a subject in need thereof, the method comprising administering to the subject a therapeutic, nutraceutical, or cosmetic formulation comprising an amino acid sequence of SEQ ID NO:5 optionally with 1 conservative amino acid substitution.

In some embodiments, the therapeutic, nutraceutical, or cosmetic formulation comprises an amino acid sequence of SEQ ID NO:6 optionally with 1 conservative amino acid substitution. In some embodiments, the therapeutic, nutraceutical, or cosmetic formulation comprises an amino acid sequence of SEQ ID NO:7 optionally with 1 conservative amino acid substitution.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 11A illustrates hematoxylin and eosin (H&E) stained histological images of the 3D skin equivalents (top row) and ex vivo skin biopsy samples (bottom row) cultured with no Peptide 14 (Control) and 12.5 µM Peptide 14 (12.5 µM Pep 14) for 5 days.

FIG. 11B illustrates the predicted age, also referred to as molecular DNA age, of the 3D skin model (top graph) and ex vivo skin biopsy (bottom graph) samples treated with 12.5 µM Peptide 14 (treatment) was lower than the predicted age for samples that were untreated control (ctrl). **$p<0.01$.

FIG. 11C illustrates the predicted age of ex vivo skin biopsy treated with 12.5 µM Peptide 14 (12.5 µM Pep 14) was lower than the predicted age of samples that were untreated control (ctrl).

DETAILED DESCRIPTION

Figure 1:
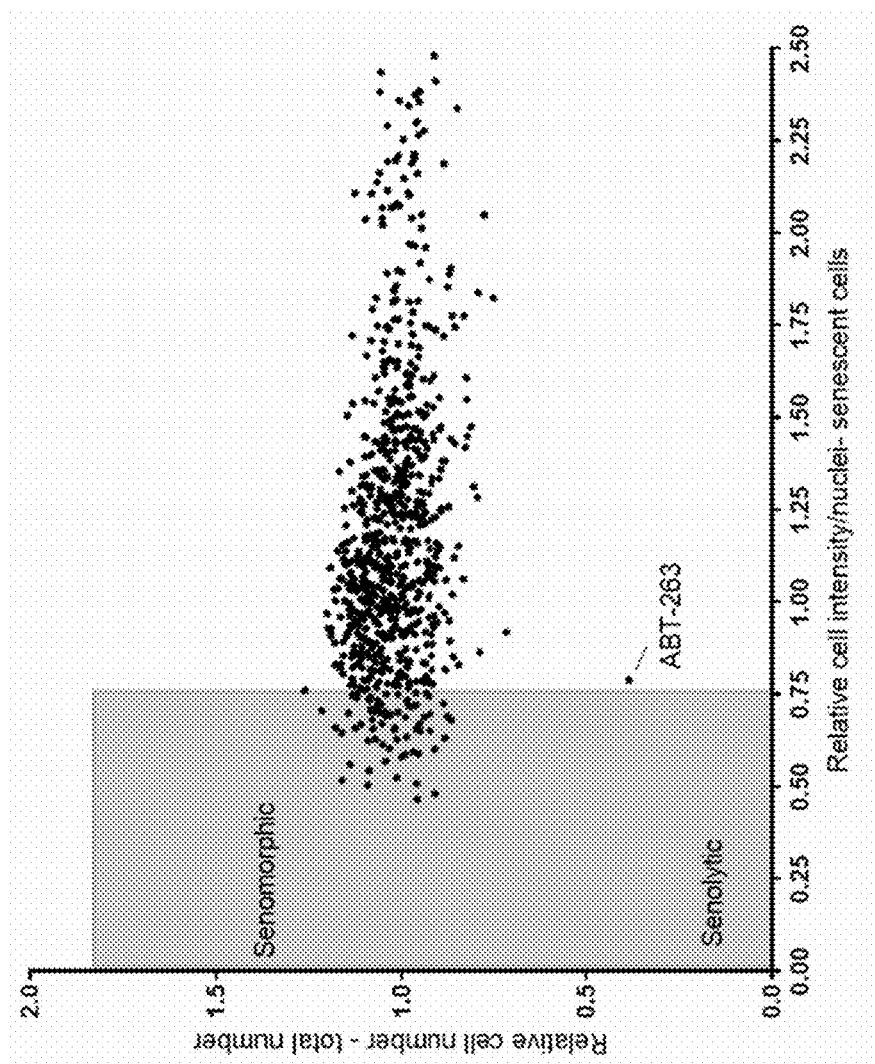
FIG. 1 illustrates the effects of individual polypeptides on progeria fibroblast cell number and senescence level.

Aging can largely result from a functional decline in the ability to maintain tissue homeostasis and integrity, possibly coupled with diminished responses to physiological demands under conditions of stress.

In a mosaic model of skin aging, senescent cells can be induced by intrinsic and extrinsic stimuli, such as time/age, UV exposure and smoking, among others. According to this model, senescent cells accumulate in the skin and actively promote tissue aging by altering the local microenvironment through a senescence-associated secretory phenotype (SASP) composed of proinflammatory cytokines among others. In some cases, senescent cells further promote skin aging by compromising epidermal stem cell renewal and promoting senescence of otherwise normal cells. Therefore, senescent cells are not only a product of skin aging, but are also active players in the aging process.

Skin dysfunction can affect the development of organismal aging and age-associated diseases and disorders. For instance, skin health and regular barrier function can be associated with lower levels of inflammatory and age-related cytokines IL-1β and IL-6 compared to counterparts with a compromised skin barrier. Increased levels of IL-1β and IL-6 have been observed in the serum of patients with several age-associated disorders, including cardiovascular disease (CVD), Alzheimer's disease, and type II diabetes. In some cases, in older adults' serum IL-6 can be associated with all-cause mortality, CVD, cancer, and liver-related mortality. In some cases, the recovery of epidermal function can effectively reduce circulating TNFα, IL-1β and IL-6 cytokine levels.

Provided herein are polypeptides, compositions comprising polypeptides and other components, and methods of use thereof. The polypeptides and compositions comprising the polypeptides can provide an anti-senescent effect (e.g., on cells of a subject). Polypeptides can promote a decrease of senescence levels in cells and tissues by promoting apoptosis, promoting DNA repair, and/or inhibiting DNA-damage induced senescence. Anti-senescent effects can include, but are not limited to, increased cell renewal rates, increased collagen production, increased hyaluronan synthase production, decreased ATRX nuclear foci accumulation, decreased p16 expression, lower SASP production, decreased senescence-associated beta-galactosidase production, reduced uneven pigmentation, maintenance of or improvement in an epidermal barrier, and reduced transepidermal water loss (TEWL). The polypeptides and compositions comprising the polypeptides provided herein may inhibit, prevent, or slow aging-associated and/or senescence-associated diseases or conditions. Furthermore, the polypeptides and compositions comprising the polypeptides may enhance or improve healthspan and/or promote lifespan.

It is to be understood that the methods and compositions described herein are not limited to the particular methodology, protocols, and reagents described herein and as such may vary. It is also to be understood that the terminology used herein is for the purpose of describing particular embodiments only, and is not intended to limit the scope of the methods and compositions described herein, which will be limited only by the appended claims.

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which the inventions described herein belong. Although any methods, devices, and materials similar or equivalent to those described herein can be used in the practice or testing of the invention described herein, the preferred methods, devices, and materials are now described.

In a peptide or polypeptide, suitable conservative substitutions of amino acids are known to those of skill in this art and can be made generally without altering the biological activity of the resulting molecule. Watson et al. (1987, Molecular Biology of the Gene, 4th Edition, The Benjamin Cummings Pub. Co., p. 224) is incorporated herein by reference. The amino acids may be either in the L- or D-isomeric form. When an amino acid residue is part of a polypeptide chain, the D-isomeric form of the amino acid can be substituted for the L-amino acid residue, as long as the desired functional property is retained. The amino acids herein can be represented by their standard IUPAC 1-letter code or 3-letter code. An amino acid residue represented by "X" or "Xxx" refers to any one of the naturally occurring or non-naturally occurring amino acid residues known in the art or to a modification of a nearby residue. Amino acid substitutions are typically of single residues, such substitutions are preferably made with those set forth in Table 1, but may be of multiple residues, either clustered or dispersed. An amino acid can be replaced with a different naturally occurring or a non-conventional amino acid residue. Such substitutions may be classified as "conservative," in which case an amino acid residue contained in a polypeptide is replaced with another naturally occurring amino acid of similar character either in relation to polarity, side chain functionality, or size. Additions encompass the addition of one or more naturally occurring or non-conventional amino acid residues. Deletion encompasses the deletion of one or more amino acid residues.

TABLE 1

Conservative and Non-Conservative Amino Acid Substitutions

| Amino Acid | Conservative Substitutions | Non-Conservative Substitutions |
|---|---|---|
| A | D, E, G, S, and T | P and V |
| C | G, R, S, W, and Y | F |
| D | A, E, G, H, N, V, and Y | |
| E | A, D, G, K, Q, and V | |
| F | I, L, and Y | C, S, and V |
| G | A, C, D, E, and R | S, V, and W |
| H | D, L, N, P, Q, R, and Y | |
| I | F, L, M, N, and V | K, R, S, and T |
| K | E, M, N, Q, R, and T | I |
| L | F, H, I, M, P, Q, R, V, and W | S |
| M | I, K, L, R, T, and V | |
| N | D, H, I, K, S, T, and Y | |
| P | H, L, Q, R, and S | A and T |
| Q | E, H, K, L, P, and R | |
| R | C, G, H, K, L, M, P, Q, T, and W | I and S |
| S | A, C, N, P, T, W, and Y | F, G, I, L, and R |
| T | A, K, M, N, R, and S | I and P |
| V | D, E, I, L, and M | A, F, and G |
| W | C, L, R, and S | G |
| Y | C, D, F, H, N, and S | |

Substitutions encompassed by the present disclosure may also be "non-conservative," in which an amino acid residue which is present in a polypeptide is substituted with an amino acid having different properties, such as a naturally-occurring amino acid from a different group (e.g., substituting a charged or hydrophobic amino acid with alanine), or alternatively, in which a naturally-occurring amino acid is substituted with a non-conventional amino acid.

The term "analog(s)" as used herein refers to a composition that retains the same structure or function (e.g., binding to a receptor) as a polypeptide, such as the same protein from a different organism. Examples of analogs include mimetics or peptidomimetics, peptides, small and large organic or inorganic compounds, as well as derivatives and variants of a polypeptide herein. Such derivatives and variants refer to polypeptides that differ from the naturally occurring polypeptides by one or more amino acid deletions, additions, substitutions, or side-chain modifications. In some embodiments, a peptide analog is a peptide in which one or more of the amino acids has undergone side-chain modifications. Examples of side-chain modifications contemplated by the present disclosure include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$. In some embodiments, a peptide analog is one in which the guanidine group of arginine residue(s) is modified by the formation of heterocyclic condensation products with reagents such as 2,3-butanedione, phenylglyoxal and glyoxal; carboxyl group(s) is modified by carbodiimide activation via O-acylisourea formation followed by subsequent derivatization, for example, to a corresponding amide; sulphydryl group(s) may be modified by methods such as carboxymethylation with iodoacetic acid or iodoacetamide; performic acid oxidation to cysteic acid; formation of mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. In any of the analogs herein, any modification of cysteine residues preferably do not affect the ability of the peptide to form the necessary disulphide bonds. In some embodiments, a peptide analog comprises tryptophan residue(s) that are modified, for example, by oxidation with N-bromosuccinimide or alkylation of the indole ring with 2-hydroxy-5-nitrobenzyl bromide or sulphenyl halides; tyrosine residues altered by nitration with tetranitromethane to form a 3-nitrotyrosine derivative; imidazole ring(s) of a histidine residue modification accomplished by alkylation with iodoacetic acid derivatives or N-carbethoxylation with diethylpyrocarbonate; proline residue(s) modified by, for example, hydroxylation in the 4-position; glycosylation variants from a completely unglycosylated molecule to a modified glycosylated molecule; and altered glycosylation patterns as a result from expression of recombinant molecules in different host cells.

The term "isolated" means altered from its natural state; i.e., if it occurs in nature, it has been changed or removed from its original environment, or both. For example, a naturally occurring polynucleotide or a polypeptide naturally present in a living animal in its natural state is not "isolated," but the same polynucleotide or polypeptide separated from the coexisting materials of its natural state is "isolated," as the term is employed herein.

The terms "protein," "peptide," "oligopeptide," or "polypeptide" as used herein refer to any composition that includes two or more amino acids joined together by a peptide bond. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. The known modifications, which may be present in polypeptides of the present disclosure, include, but are not limited to, acetylation, acylation, ADP-ribosylation, amidation, covalent attachment of a flavonoid or a heme moiety, covalent attachment of a polynucleotide or polynucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycation, glycosylation, glycosylphosphatidyl inositol (GPI) membrane anchor formation, hydroxylation, iodination, methylation, myristoylation, oxidation, proteolytic processing, phosphorylation, prenylation, racemization, selenoylation, sulfation, transfer-RNA mediated addition of amino acids to polypeptides such as arginylation and ubiquitination. The term "protein" also includes "artificial proteins" which refers to linear or non-linear polypeptides, consisting of alternating repeats of a polypeptide (e.g., SEQ ID NOs: 1-7) and a spacer. A DNA construct encoding the polypeptide and spacer alternate repeats can be synthesized using methods known in the art (see Rotzschke et al., 1997, Proc. Natl. Acad. Sci. USA 94:14642-14647).

The term "purified" as used herein to describe a polypeptide, polynucleotide, or other composition, refers to such polypeptide, polynucleotide, or other composition separated from one or more compounds which are usually associated with it in nature. Such other compositions can be, for example, other polypeptides or polynucleotides, carbohydrates, lipids, etc. The term "purified" can also be used to specify the separation of monomeric polypeptides of the disclosure from oligomeric forms such as homo- or heterodimers, trimers, etc. A substantially pure polypeptide typically comprises at least about 50%, 60%, 70%, 80%, or 90% weight/weight of a polypeptide sample, or more preferably at least about 95%, 96%, 97%, 98%, 99%, or 99.5% weight/weight of a polypeptide sample. As a preferred embodiment, a polypeptide of the present disclosure is at least 10%, 20%, 30%, 40%, 50%, 60%, 70%, 80%, 90%, 95%, 96%, 97%, 98%, 99%, or 100% pure relative to heterologous polypeptides.

The term "subject," or "patient" as used herein, encompasses animals. In some embodiments, the subject may be a mammal. Examples of mammals include, but are not limited to, any member of the Mammalian class: humans, non-human primates such as chimpanzees, and other apes and monkey species; farm animals such as cattle, horses, sheep, goats, and swine; domestic animals such as rabbits, dogs, and cats; laboratory animals including rodents, such as rats, mice, and guinea pigs, and the like. The mammal can be a human.

The terms "treat," "treating," or "treatment," as used herein, include delaying the onset of, reducing the occurrence of, or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "therapeutically acceptable," as used herein, refers to a material, including but not limited, to a salt, carrier, or diluent, which does not abrogate the biological activity or properties of the compound, and is relatively nontoxic, i.e., the material may be administered to a subject without causing undesirable biological effects or interacting in a deleterious manner with any of the components of the composition in which it is contained.

The term "carrier," as used herein, refers to relatively nontoxic chemical compounds or agents that facilitate the incorporation of a compound into cells or tissues.

The term "diluent," as used herein, refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to, a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

Senescent cells can be identified by senescence-associated beta-galactosidase (SA-BGal) production, p16 expression, presentation of SASP, and/or alpha thalassemia/mental retardation X-linked chromatin remodeling protein (ATRX) foci accumulation in the nuclei. Functional alterations that can also distinguish senescent cells, include, but are not limited to, decreased proliferation capacity and resistance to mitogenic stimuli.

Aging generally results from a functional decline in the ability to maintain tissue homeostasis and integrity, coupled with diminished responses to physiological demands under conditions of stress.

With regard to skin aging, a mosaic model has been proposed, in which senescent cells are induced by intrinsic and extrinsic stimuli, such as time/age, UV exposure, and smoking, among other stimuli. According to the mosaic model, senescent cells accumulate in the skin and actively promote tissue aging by altering the local microenvironment through a senescence-associated secretory phenotype (SASP) composed of proinflammatory cytokines among others. It has been shown that senescent cells can promote skin aging by compromising epidermal stem cell renewal and promoting senescence of otherwise normal cells. Therefore, senescent cells may not only be a product of skin aging, but may also be an active player in the aging process.

Polypeptides have properties such as multifunctional behavior which can make them useful for cosmetic or therapeutic applications, including senotherapy. Skin dysfunction observed during aging can affect the development of age-associated diseases and disorders.

Polypeptides

Polypeptides and compositions comprising polypeptides as provided herein can provide a senotherapeutic effect, e.g., the polypeptide can reduce senescence, such as by halting senescence, preventing senescence, inhibiting senescence, reversing senescence, destroying senescent cells, killing senescent cells, removing senescent cells, or by any suitable mechanism of reducing the burden or effects of senescent cell accumulation. Such polypeptides can in some cases comprise the amino acid sequence LKGI (SEQ ID NO:5). Compositions comprising such polypeptides can be employed or used to provide a senotherapeutic effect.

The polypeptides (e.g., senotherapeutic polypeptides) can comprise at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more amino acids. In some cases, the polypeptides may be no more than 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, or 100 amino acids long. In some cases, the polypeptides can be from 4 to 25, from 4 to 15, or from 4 to 10 amino acids in length. In some embodiments, the polypeptides can comprise at least 30, 40, 50, 60, 70, 80, 90, 100, or more amino acids. In certain embodiments, the polypeptides may comprise less than 100, 90, 80, 70, 60, 50, 40, 30, or fewer amino acids.

Examples of polypeptides which can provide a senotherapeutic effect are provided in Table 2 below.

TABLE 2

Example Polypeptide Amino Acid Sequences

| Name | SEQ ID NO: | Amino Acid Sequence |
|---|---|---|
| Peptide 14 | 1 | ETAKHWLKGI |
| Peptide 13 | 2 | ATAKAWLKGI |
| Peptide 15 | 3 | KLKGILRGAA |
| Peptide 16 | 4 | WLKGILREAA |

A polypeptide can be an isolated or recombinant polypeptide, which can comprise an amino acid sequence of $X_1X_2X_3X_4X_5X_6X_7X_8X_9X_{10}$. Amino acids included in the polypeptide can comprise a natural amino acid, which can include alanine (Ala, A), arginine (Arg, R), asparagine (Asn, N), aspartic acid (Asp, D), cysteine (Cys, C), glutamine (Glu, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), or valine (Val, V).

In some cases, the isolated or recombinant polypeptide comprising an amino acid sequence of $X_1X_2X_3X_4X_5X_6X_7X_8X_9X_{10}$ can comprise an amino acid sequence having at least 70%, 75%, 80%, 85%, 90%, or 95% identity to a first sequence, ETAKHWLKGI (SEQ ID NO:1), wherein $X_1$ is E, $X_2$ is T, $X_4$ is K, $X_6$ is W, $X_7$ is L, $X_9$ is G, and $X_{10}$ is I; and wherein at least either (i) $X_3$ is not S (SEQ ID NO: 8); or (ii) if $X_5$ is any amino acid then $X_8$ is not G (SEQ ID NO: 29); or (iii) if $X_8$ is any amino acid then $X_5$ is not N (SEQ ID NO: 30); or (iv) any one of (i), (ii), or (iii), where the sequence can optionally comprise 1, 2, 3, or 4 conservative amino acid substitutions. In some cases, the isolated or recombinant polypeptide can include an amino acid sequence having at least 70%, 75%, 80%, 85%, 90%, 95%, or 100% identity to a sequence of ETAKHWLKGI (SEQ ID NO:1). The present disclosure also contemplates analogs, such as peptidomimetics of the above.

In some cases, the isolated or recombinant polypeptide comprising an amino acid sequence of $X_1X_2X_3X_4X_5X_6X_7X_8X_9X_{10}$ can comprise an amino acid sequence having at least 70%, 75%, 80%, 85%, 90%, or 95% identity to a second sequence, ATAKAWLKGI (SEQ ID NO: 2), wherein $X_1$ is A, $X_2$ is T, $X_3$ is A, $X_4$ is K, $X_5$ is A, $X_6$ is W, $X_7$ is L, $X_8$ is K, $X_9$ is G, and $X_{10}$ is I. Such a recombinant polypeptide can optionally comprise 1, 2, 3, or 4 conservative amino acid substitutions. In some cases, the isolated or recombinant polypeptide can include an amino acid sequence having at least 70%, 75%, 80%, 85%, 90%, 95%, or 100% identity to a sequence of ATAKAWLKGI (SEQ ID NO:2). The present disclosure also contemplates analogs, such as peptidomimetics of the above.

In some cases, the isolated or recombinant polypeptide comprising an amino acid sequence of $X_1X_2X_3X_4X_5X_6X_7X_8X_9X_{10}$ can comprise an amino acid sequence having at least 70%, 75%, 80%, 85%, 90%, or 95% identity to a third sequence, KLKGILRGAA (SEQ ID NO:3), wherein at least either (i) if $X_9$ is any amino acid then $X_3$ is not N (SEQ ID NO: 31); or (ii) if $X_3$ is any amino acid then $X_9$ is not S (SEQ ID NO: 32); or (iii) if $X_4$ is any amino acid then $X_7$ is not L (SEQ ID NO: 33); or (iv) if $X_7$ is any amino acid then $X_4$ is not S (SEQ ID NO: 34); or (v) any one of (i), (ii), (iii), or (iv), where the sequence can optionally comprise 1, 2, 3, or 4 conservative amino acid substitutions. In some cases, the isolated or recombinant polypeptide can include an amino acid sequence having at least 70%, 75%, 80%, 85%, 90%, 95%, or 100% identity to a sequence of KLKGILRGAA (SEQ ID NO:3). The present disclosure also contemplates analogs, such as peptidomimetics of the above.

In some cases, the isolated or recombinant polypeptide comprising an amino acid sequence of $X_1X_2X_3X_4X_5X_6X_7X_8X_9X_{10}$ can comprise an amino acid sequence having at least 80%, 85%, 90%, or 95% identity to a fourth sequence, WLKGILREAA (SEQ ID NO:4), wherein $X_1$ is W, $X_2$ is L, $X_3$ is K, $X_4$ is G, $X_5$ is I, $X_6$ is L, $X_7$ is R, $X_8$ is E, $X_9$ is A, and $X_{10}$ is A. Such a recombinant polypeptide can optionally comprise 1, 2, 3, or 4 conservative amino acid substitutions. In some cases, the isolated or recombinant polypeptide can include an amino acid sequence having at least 80%, 85%, 90%, 95%, or 100% identity to a sequence of WLKGILREAA (SEQ ID NO:4). The present disclosure also contemplates analogs, such as peptidomimetics of the above.

In some cases, a polypeptide can comprise the amino acid sequence LKGI (SEQ ID NO:5), LKGIL (SEQ ID NO:6), or WLKGI (SEQ ID NO:7) (see Table 3 below).

TABLE 3

Example Polypeptide Amino Acid Sequences

| SEQ ID NO: | Amino Acid Sequence |
|---|---|
| 5 | LKGI |
| 6 | LKGIL |
| 7 | WLKGI |

A polypeptide comprising one of SEQ ID NOs:5-7 may comprise at least 4, 5, 6, 7, 8, 9, 10, 20, 30, 40, or 50 amino acids. In some embodiments, a polypeptide comprising one of SEQ ID NOs:5-7 may comprise no more than 4, 5, 6, 7, 8, 9, 10, 20, 30, 40, 50, 60, 70, 80, 90, or 100 amino acids. SEQ ID NOs:5-7 can be at the N-terminus of a polypeptide, at the C-terminus of a polypeptide, or between the N-terminus and C-terminus of a polypeptide. In some cases, a polypeptide can comprise more than one of SEQ ID NOs: 5-7.

The polypeptide can be isolated, substantially pure, or purified. In some cases, an isolated polypeptide can be (i) synthesized chemically or (ii) expressed in a host cell and purified away from associated and contaminating proteins. In some cases, the polypeptide can be present in a host cell as the expression product of a portion of an expression vector, and can be linked to a protein moiety or linked to a chemical moiety.

Analogs, including peptidomimetics, of the disclosed polypeptides can provide a senotherapeutic effect. The peptides and polypeptides disclosed herein may include peptidomimetic equivalents.

In some cases, as discussed above, a polypeptide can have a sequence identity to a polypeptide described herein. Sequence identity of a polypeptide can refer to an exact amino acid-to-amino acid correspondence of two polypeptide sequences. In some cases, techniques for determining sequence identity can include determining the amino acid sequence and comparing the amino acid sequence to a second amino acid sequence. Two or more sequences can be compared by determining their percent identity, or the number of exact matches between two aligned sequences divided by the length of the longer sequence and multiplied by 100. Percent identity may also be determined, for example, by comparing sequence information using the advanced BLAST computer program, including, e.g., version 2.2.9, available from the National Institutes of Health. The BLAST program is based on the alignment method of Karlin and Altschul, Proc. Natl. Acad. Sci. USA, 87:2264-2268 (1990) and as discussed in Altschul, et al., J. Mol. Biol., 215:403-410 (1990); Karlin and Altschul, Proc. Natl. Acad. Sci. USA, 90:5873-5877 (1993); and Altschul et al., Nucleic Acids Res. 25:3389-3402 (1997). The program may be used to determine percent identity over the entire length of the polypeptides being compared. Default parameters are provided to optimize searches with short query sequences in, for example, the blastp program. The program also allows the use of an SEG filter to mask-off segments of the query sequences as determined by the SEG program of Wootton and Federhen, Computers and Chemistry 17:149-163 (1993).

Compositions

Disclosed herein are compositions comprising one or more of the polypeptides described herein. In some embodiments, the compositions may be senotherapeutic. In some cases, a composition can be used to treat an age-related disease or condition or age-associated disorder, e.g., to delay the onset of, reduce the occurrence of, or ameliorate the age-related disease or condition or age-associated disorder. In some cases, a composition can be used to treat tissue lesion, to delay the onset of, reduce the occurrence of, or ameliorate the tissue lesion, for example, UV damage upon sun exposure.

In some cases, a composition may include, e.g., an effective amount of a polypeptide, alone or in combination, with one or more vehicles (e.g., therapeutically acceptable compositions or therapeutically acceptable carriers) and other therapeutically effective compounds. In some embodiments, the effective amount of the polypeptide refers to having a desired effect on a subject, including but not limited to a cell, a tissue, or an organism, treated with the composition. In some embodiments, the effective amount of the polypeptide has minimal or low effect systemically on the treated subject. In some embodiments, the effective amount of the polypeptide has maximal effect locally at or near the treated area. In some embodiments, the formulation can be configured to penetrate topically from the epidermis to the dermis. In some embodiments, the formulation is configured to penetrate topically through the epidermis layers. In some embodiments, the effective amount of a polypeptide is at least 1 nM, 5 nM, 10 nM, 50 nM, 100 nM, 500 nM, 1 µM, at least 10 µM, at least 25 µM, at least 50 µM, at least 75 µM, at least 100 µM, at least 150 µM, at least 200 µM, at least 250 µM, at least 300 µM, at least 350 µM, at least 400 µM, at least 450 µM or at least 500 µM. In some instances, the effective amount of a polypeptide is between about 1 nM to about 1000 nM, about 5 nM to about 750 nM, about 25 nM to about 750 nM, or about 50 nM to about 500 nM. In some instances, the effective amount of a polypeptide is between about 1 µM to about 500 µM, about 25 µM to about 250 µM, about 50 µM to about 200 µM, or about 75 µM to about 125 µM. In some instances, the effective amount of a polypeptide is at least 0.00001%, 0.00005%, 0.0001%, 0.0005%, 0.001%, at least 0.005%, at least 0.01%, at least 0.05%, at least 0.1%, at least 0.5%, at least 1%, at least 1.5%, at least 2%, at least 2.5%, at least 3%, at least 3.5%, at least 4%, at least 4.5%, or at least 5% (w/w) of the final composition. In some embodiments, the effective amount of a polypeptide between about 0.00001% to about 5%, 0.00001% to about 1%, 0.00001% to about 0.1%, about 0.001% to about 5%, about 0.005% to about 4%, about 0.005% to about 3%, about 0.005% to about 2%, about 0.005% to about 1%, or about 0.005% to about 0.5% of the final composition In some embodiments, the effective amount of the polypeptide for an in vivo application may be at least 2, 5, 10, 20, 30, 40, 50, 60, 70, 80, 90, 100, 150, 200, 250, 300, 350, 400, 450, or 500 times than the amount used in an in vitro application. The effective amount of polypeptide results in some dermis penetration of the polypeptide, in some instances about 1% penetration, about 2% penetration, about 4% penetration, about 5% penetration, or about 10% penetration. In some instances, no more than 1%, 2%, 3%, 4%, 5%, 6%, 7%, 8%, 9%, or 10% of the polypeptide in the composition applied onto the skin penetrates into the dermis. In some instances, at least 1%, 2%, 3%, 4%, 5%, 6%, 7%, 8%, 9%, or 10% of the polypeptide in the composition applied onto the skin penetrates into the dermis. In some instances, the amount used in an in vivo application is a factor of amount of dermal penetration in an in vitro penetration study. In some instances, the factor for the amount used in an in vivo application is at least 2, 5, 10, 20, 30, 40, 50, 60, 70, 80, 90, 100, 150, 200, 250, 300, 350, 400, 450, 500, 550, 600, 650, 700, 750, 800, 850, 900, 950, or 1000 times the amount of in vitro dermal penetration.

In some cases, the compositions described herein can be administered with one or more additional nutraceutical, cosmetic, therapeutic, or pharmaceutical treatments (e.g., co-administered, sequentially administered, or co-formulated).

In some embodiments, the formulation may be used in conjunction with one or more treatments. In some embodiments, the formulation may be used with a sonic treatment, an ultrasonic treatment, a LED treatment, a light treatment, an electrical treatment, a radiofrequency treatment, or other dermatological treatments. In some embodiments, the composition is applied to the skin before, after, or during the treatment.

A composition can be formulated for topical application. For example, the composition may be formulated for application onto skin. In some embodiments, the composition is configured as a topical supplement. Formulations such as those for topical application can be a cream, an ointment, a gel, a liquid, a powder, a lotion, a serum, an emulsion, a moisturizer, a foam, a face mask, a mousse, an aerosol, a spray, a cleanser, a toner, a topical patch, a hydrogel patch, or a shampoo. Polypeptides applied topically can be applied to an affected area, to an area which may become affected in the future, a portion of the subject, or substantially the entire subject. In some cases, a topical treatment can be applied with a buffer, another topical treatment, a cream, or a moisturizer.

A composition, such as for topical application, can be formulated as a cosmetic composition. Examples of cosmetic compositions can include makeup, foundation, sunscreen, after sun lotion, and skin care products, including anti-aging skin care products. In some cases, makeup compositions can leave color on the face, and can include foundation, bronzer, mascara, concealer, eye liner, brow color, eye shadow, blusher, lip color, powder, a solid emulsion compact, or other makeup items. In some cases, skin care products can be those used to treat or care for, or somehow moisturize, improve, accelerate renewal, protect, prevent damage, or clean the skin. A skin-care product can be applied as a cream, a topical patch, a hydrogel patch, a transdermal patch, an ointment, a gel, a liquid, a powder, a lotion, a serum, an emulsion, an oil, a clay, a moisturizer, a foam, a face mask, a mousse, an aerosol, a spray, a cleanser, a toner, or a shampoo. In some cases, skin-care products can be in the form of an adhesive, a bandage, exfoliant, a toothpaste, a moisturizer, a lotion, a primer, a lipstick, a lip balm, an anhydrous occlusive moisturizer, an antiperspirant, a deodorant, a personal cleansing product, an occlusive drug delivery patch, a nail polish, a powder, a tissue, a wipe, a hair conditioner, or a shaving cream.

A composition as contemplated herein can also be edible, i.e., formulated as an edible supplement or beverage, such that the composition is formulated to be safely consumed by humans. In some cases, an edible composition can be therapeutically effective to treat an age-related disease or condition or age-associated disorder. In some cases, an edible supplement can be configured as a tablet, capsule, chew, gummy, powder, food bar, meal replacement bar, or a food additive. In some cases, a beverage can be formulated to comprise water, a soda, a tea, coffee, milk, a juice, a shake, a drink, or other edible liquid.

In some cases, a composition can comprise a skin conditioning agent (e.g., a humectant, exfoliant, emollient, or hydrator). A humectant can be for moisturizing, reducing scaling, or stimulating removal of built-up scale from the skin. An exfoliant can be for the removal of old skin cells from the surface, and can be a physical exfoliant or a chemical exfoliant. An emollient can be a preparation or ingredient which can soften dry, rough, or flakey skin. A hydrator can be for moisturizing, reducing scaling, or stimulating removal of built-up scale from the skin. In some cases, emollient is an agent that prevents water loss and has a softening and soothing effect on skin. In some embodiments, emollients may comprise at least one of plant oils, mineral oil, shea butter, cocoa butter, petrolatum, fatty acids (animal oils, including emu, mink, and lanolin), triglycerides, benzoates, myristates, palmitates, stearates, glycolipids, phospholipids, squalene, glycerin, rose hip oil, andiroba oil, grape seed oil, avocado oil, plum seed oil, pracaxi oil, *Calycophyllum spruceanum* oil, almond oil, argan oil, caprylic/capric triglyceride, jojoba butter, jojoba oil, Spectrastat G2, ceramide, and algae extract. In some cases, the composition comprises a skin hydrating agent, also referred to as a skin hydrator. In some cases, the skin hydrating agent include but are not limited to glycerin, squalene, sorbitol, hyaluronic acid, hyaluronic acid derivatives, sodium hyaluronate, sodium hyaluronate crosspolymer, niacinamide, glycoproteins, pyrrolidone carboxylic acid (PCA), lysine HCl, allantoin and algae extract. In some embodiments, the composition comprises at least 1%, 2%, 3%, 4%, 5%, 6%, 7%, 8%, 9%, or 10% skin conditioning agent. In some embodiments, the composition comprises about 1% to about 70%, about 1% to about 60%, about 1% to about 50%, about 5% to about 50%, about 5% to 45%, or about 5% to 40% skin conditioning agent.

A composition can comprise a shine control agent, which can improve or regulate the shiny appearance of skin. Shine control agents can be porous in nature. Such agents can provide a reservoir to absorb excess moisture to reduce the appearance of shine. Shine control agents can be silicas, magnesium aluminum silicates, talc, sericite and various organic copolymers. Particularly effective shine control agents can include silicates or carbonates that are formed by reaction of a carbonate or silicate with the alkali (IA) metals, alkaline earth (IA) metals, or transition metals, and silicas (silicon dioxide). Preferred shine control agents are selected from the group consisting of calcium silicates, amorphous silicas, calcium carbonates, magnesium carbonates, zinc carbonates, bentonite clay, and combinations thereof.

A composition can comprise a film forming agent, which can aid film substantivity and adhesion to the skin. A film forming agent can improve long wear and non-transfer performance of a composition. Film forming agents can be water soluble, water insoluble, or water dispersing. Film forming agents can be 1) organic silicone resins, fluorinated silicone resins, copolymers of organic silicone resins, trimethylsiloxysilicate, GE's copolymers of silicone resins, SF1318 (silicone resin and an organic ester of isostearic acid copolymer) and CF1301 (silicone resin and alpha methyl styrene copolymer), Dow Corning's pressure sensitive adhesives copolymers of silicone resins and various PDMS's (BIO-PSA series); and 2) acrylic and methacrylic polymers and resins, silicone-acrylate type copolymers and fluorinated versions of, including silicones plus polymer from 3M, KP545 from Shin-Etsu, alkyl-acrylate copolymers, KP 561 and 562 from Shin-Etsu; 3) decene/butene copolymer from Collaborative Labs; 4) polyvinyl based materials, PVP, PVP/VA, including Antaron/Ganex from ISP (PVP/Triacontene copolymer), Luviskol materials from BASF; polyurethanes, the Polyderm series from Alzo including but not limited to Polyderm PE/PA, Polyderm PPI-SI-WS, Polyderm PPI-GH, Luviset P.U.R. from BASF; 6) polyquaternium materials, Luviquat series from BASF; 7) acrylates copolymers and acrylates/acrylamide copolymers, Luvimer and Ultrahold series, both available from BASF; 8) styrene based materials; and 9) chitosan and chitosan based materials including cellulose and cellulose-based materials.

A composition can comprise a thickening agent or an emulsifying agent. A thickening agent may be used to increase the viscosity of liquid base materials to be used in a cosmetic composition. The selection of a particular thickening agent can depend on a type of composition desired (e.g., gel, cream, lotion, or wax based), the desired rheology, the liquid base material used, and other materials to be used in the composition. Examples of thickening agent or an emulsifying agent can include waxy materials such as candelilla, carnauba waxes, beeswax, spermaceti, carnauba, baysberry, montan, ozokerite, ceresin, paraffin, synthetic waxes such as Fisher-Tropsch waxes, silicone waxes (DC 2503 from Dow Corning), microcrystalline waxes and the like; soaps, such as the sodium and potassium salts of higher fatty acids, acids having from 12 to 22 carbon atoms; amides of higher fatty acids; higher fatty acid amides of alkylolamines; dibenzaldehyde-monosorbitol acetals; alkali metal and alkaline earth metal salts of the acetates, propionates and lactates; and mixtures thereof. Also useful are polymeric materials such as, locust bean gum, sodium alginate, sodium caseinate, egg albumin, gelatin agar, carrageenin gum sodium alginate, xanthan gum, quince seed extract, tragacanth gum, starch, chemically modified starches and the like, semi-synthetic polymeric materials such as cellulose, cellulose derivatives, cellulose ethers hydroxyethyl cellulose, methyl cellulose, hydroxypropyl cellulose, carboxymethyl cellulose, hydroxy propylmethyl cellulose, polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol polyacrylic acid polymers, poly(acrylic acid), carbomers, polymethacrylic acid polymers, polyvinyl acetate polymers, polyvinyl chloride polymers, polyvinylidene chloride polymers and the like. Inorganic thickeners may also be used such as aluminum silicates, such as, for example, bentonites, or a mixture of polyethylene glycol and polyethylene glycol stearate or distearate. An emulsifier may be used to help keep hydrophilic and hydrophobic ingredients from separating in an emulsion. In some cases, emulsifiers include but are not limited to Olivem, Oliwax LC, polysorbates, laureth-4, and potassium cetyl sulfate.

A cosmetic composition can provide a temporary change in an appearance or can provide a long-term change in an appearance. In some cases, a cosmetic composition can be formulated to provide a short-term change in an appearance (e.g., color deposition or plumping of skin) as well as a long-term change in appearance (e.g., reduction in spots, appearance of fine lines, appearance of wrinkles, or other features which can affect appearance).

A composition can comprise an additive that has an additive or synergistic effect when applied with a polypeptide as disclosed herein. For example, a composition comprising a polypeptide and an additive can have a greater effect on senescence, and age-related disease or condition, or an age-associated disorder (e.g., delay the onset of, reduce the occurrence of, or ameliorate one or more symptoms) than the individual effect of the additive, the polypeptide, or the sum of the individual effects of the additive and the polypeptide. Additives can be an additional polypeptide, a glycosaminoglycan, a carbohydrate, a polyphenol, a protein, a lipid, a plant aqueous or oil extract, a nucleic acid, an antibody, a small molecule, a vitamin, a humectant, an emollient, or another suitable additive. In some embodiments, the composition comprises a UV blocker. In some embodiments, the UV blocker may include but is not limited to aminobenzoic acid, avobenzone, cinoxate, dioxybenzone, homosalate, meradimate, octocrylene, octinoxate, octisalate, oxybenzone, padimate O, ensulizole, sulisobenzone, titanium dioxide, trolamine salicylate, and zinc oxide.

Often the methods, systems, and compositions provided herein comprise a vitamin. In some instances, the vitamin provides skin soothing, skin restoring, skin replenishing, and/or hydrating effects. In some instances, the vitamin provides antioxidant effects. In some instances, the vitamin acts as an emollient. In some instances, the vitamin improves the appearance of enlarged pores, uneven skin tone, fine lines, dullness, and/or a weakened skin surface. In some instances, the vitamin is vitamin A, vitamin D, vitamin E, vitamin F, vitamin K, vitamin B1 (thiamine), vitamin B2 (riboflavin), vitamin B3 (niacin), vitamin B5 (pantothenic acid), vitamin B7 (biotin), vitamin B6, vitamin B12 (cyanocobalamin), vitamin B9, folic acid, niacinamide, and mixtures thereof. In some instances, the composition comprises a derivative of a vitamin. In some instances, a derivative of a vitamin is used to improve stability of the vitamin in the composition and/or compatibility of the vitamin derivative with other ingredients in the composition. In some instances, the composition comprises vitamin B3 or its derivative and vitamin E or its derivative. In some instances, the composition comprises niacinamide and vitamin E or its derivative. In some instances, the composition comprises vitamin C or its derivative, vitamin B3 or its derivative, and vitamin E or its derivative. In some embodiments, the composition comprises at least 0.01%, 0.05%, 0.5%, 1%, 2%, 3%, 4%, 5%, 6%, 7%, 8%, 9%, or 10% vitamin. In some embodiments, the composition comprises about 0.1% to about 10%, about 0.1% to about 5%, about 0.5% to about 10%, about 0.5% to about 5%, about 1% to 10%, or about 1% to 5% vitamin.

Compositions for topical administration can further comprise a carrier. The carrier may be a solution, an emulsion, an ointment, an oil, or a gel base. The gel base, for example, may comprise one or more of the following: petrolatum, lanolin, PEG(s), beeswax, mineral oil, diluents such as water and alcohol, emulsifiers, and/or stabilizers. Thickening agents may be present in a therapeutic composition for topical administration. If intended for transdermal administration, the composition may include a transdermal patch or iontophoresis device. In some cases, biodegradable microspheres (e.g., polylactic acid) may also be employed as carriers for a composition. In some cases, the transdermal patch is prepared to deliver the formulation to the epidermal layer of the skin. In some cases, the transdermal patch is prepared to deliver the formulation to the epidermal and dermal layers of the skin. In some cases, the formulation is prepared as to be minimally delivered systemically in the subject or is not intended to be delivered directly into the bloodstream of the subject.

A composition may also contain one or more diluents such as buffers, or one or more antioxidants such as ascorbic acid, low molecular weight polypeptides, polypeptides, amino acids, carbohydrates including glucose, sucrose or dextrins, chelating agents such as EDTA, glutathione and other stabilizers. Neutral buffered saline or saline mixed with nonspecific serum albumin are exemplary diluents. A product may be formulated as a lyophilizate using suitable excipient solutions (e.g., sucrose) as diluents.

A composition can also comprise one or more excipients, such as a therapeutic, nutraceutical, or cosmetic excipient. Examples of excipients can comprise antiadherents, binders, coatings, colors, disintegrants, flavors, glidants, lubricants, preservatives, sorbents, sweeteners, or vehicles.

Suitable excipients or stabilizers can be nontoxic to recipients at the dosages and concentrations employed, and can comprise buffers such as phosphate, citrate, and other organic acids; salts such as sodium chloride; antioxidants including ascorbic acid, vitamin E, and methionine; preservatives (such as, for example, octadecyldimethylbenzyl ammonium chloride; hexamethonium chloride; benzalkonium chloride, benzethonium chloride; glucoonolactone and sodium benzoate; phenol, butyl or benzyl alcohol; low molecular weight (less than about 10 residues) polypeptides; proteins such as serum albumin or gelatin; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA or EDTA alternatives (e.g. Biopure GLDA, Spectrastat G2); sugars such as sucrose, mannitol, trehalose, or sorbitol; salt-forming counter-ions such as sodium; metal complexes (e.g., Zn-protein complexes); and/or surfactants. In some instances, a surfactant includes, but is not limited to, polysorbate 20, polysorbate 80, alginate, a poloxamer, TRITON (t-octylphcnoxypolyethoxyethanol); nonionic detergent; sodium dodecyl sulfate (SDS); sodium laurel sulfate; sodium octyl glycoside; lauryl-, myristyl-, linoleyl-, or stearyl-sulfohetame; lauryl-, yristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroarnidopropyl); myristamidopropyl-, palmidopropyl-, or isostearamidopropyl-dimethylamin sodium methyl cocoyl-, or disodium methyl oleyl-taurate; sorbitan monopalmitate; and the MONAQUAT series (Mona Industries. Inc., Paterson, NJ); polyethylene glycol (PEG), polypropylene glycol (PPG), copolymers of poloxyethylene and poloxypropylene glycol (e.g., Pluronies/Poloxamer, PLURONIC® F68, etc.); or another suitable surfactant. In some cases, the composition can comprise squalene, natural oils, plant extracts, hyaluronic acid, or clay. In some cases, the composition comprises a skin penetrating enhancer to enhance the penetration of active ingredients into the skin. In some cases, the skin penetrating enhancer may include but are not limited to fatty acids, essential oils, urea, liposomes, microsphere, DMSO, azone, sodium PCA, and squalene.

In some embodiments, the formulation comprises a carrier, a microsphere, a liposome, or a micelle in order to carry the polypeptide and control the release time and/or penetration depth of the polypeptide in the through the skin.

In some embodiments, the polypeptide is functionalized. In some embodiments, the polypeptide is functionalized with a chemical group. In some embodiments, the polypeptide is functionalized with a functional group comprising no more than 3, 4, 5, 6, 7, 8, 9, 10, 11, 12, 13, 14, 15, 16, 17, 18, 19, 20, or more than 20 carbons. In some embodiments, the polypeptide is functionalized with acetyl or palmitoyl.

A polypeptide or composition to be applied to a subject can be sterilized. This may be accomplished by, for example, filtration through sterile filtration membranes, or any other art-recognized method for sterilization.

A composition can comprise a therapeutically effective amount of a polypeptide or peptidomimetic in an amount which can delay the onset of, reduce the occurrence of, or ameliorate one or more symptoms, such as a symptom of the skin, of an age-related disease or condition, or age-associated disorder. In some cases, a therapeutically effective amount can be an amount of a therapeutic agent (e.g., a polypeptide) that can provoke a therapeutic (e.g., senotherapeutic) or desired response in a subject. A therapeutically effective amount can be sufficient to cause a therapeutic benefit to the subject. The therapeutically effective amount can vary depending on a variety of factors including the active agent selected for use, and the age, weight, height, and/or general health of a subject to be treated.

As is understood in the clinical context, an effective therapeutic amount of an active agent may or may not be achieved in conjunction with another drug, compound, therapeutic, or pharmaceutical composition. Thus, an effective therapeutic amount may be considered in the context of administering one or more active agents, and a single active agent may be considered to be given in an effective amount if, in conjunction with one or more other active agents, a desirable result may be or is achieved. Accordingly, in some instances, one or more active agents may be administered to the subject. In other instances, treatment with an active agent described herein is conducted prior to, or after, one or more other treatment modalities described herein.

Polypeptide Synthesis

Also disclosed are isolated polynucleotides encoding one or more of the presently disclosed polypeptides. The isolated polynucleotides may be present in an expression vector comprising the isolated polynucleotides operably linked to a promoter. The expression vector may be present in an isolated cell (i.e., a recombinant cell transfected or transformed with the expression vector).

Suitable expression vectors may include bacterial, plant, fungal, insect, or animal host cell replication, and/or expression vectors that express the disclosed peptides, polypeptides, and variants thereof. Expression vectors may be used to transform appropriate host cells (e.g., *E. coli*). The transformed host cell may be cultivated or fermented such that the peptide or polypeptide is expressed constitutively or after adding a reagent that induces expression (e.g., via an inducible promoter). Expression vectors as contemplated herein may include control sequences that modulate expression of the encoded polypeptide. Expression control sequences may include constitutive or inducible promoters (e.g., T3, T7, Lac, trp, or phoA), ribosome binding sites, or transcription terminators.

An expression vector can be utilized to transform host cells. Suitable host cells include bacterial, plant, fungal, insect, or animal host cells. Suitable bacteria include, but are not limited to: Gram-negative bacteria such as *Escherichia* species (e.g., *E. coli*), other Gram-negative bacteria, (e.g., *Pseudomonas* sp., such as *Pseudomonas aeruginosa*, or *Caulobacter* sp., such as *Caulobacter crescentus*), or Gram-positive bacteria (e.g., *Bacillus* sp., such as *Bacillus subtilis*). Suitable fungal cells may include yeast (e.g., *Saccharomyces cerevisiae*).

An expression vector can, for example, provide a mechanism for synthesis of a polypeptide. Synthesis can take place in a cell, for example an animal cell, a plant cell, a bacterial cell, or a yeast cell. An expression vector can comprise nucleic acids, e.g., DNA derived from a plasmid, cosmid, phasmid, or bacteriophage or synthesized by chemical or enzymatic means, into which one or more fragments of nucleic acid may be inserted or cloned which can encode one or more polypeptides described herein. An expression vector may be capable of autonomous replication in a defined host or organism such that the cloned sequence is reproduced. An expression vector can have a linear, circular, or supercoiled configuration and may be complexed with other vectors or other materials for certain purposes. The components of an expression vector can comprise, but are not limited to, a DNA molecule incorporating: (1) DNA; (2) a sequence encoding a therapeutic or desired product; or (3) regulatory elements for transcription, translation, RNA stability, and replication.

A polypeptide can be produced using an expression vector. In some cases, such production can comprise cultivating or fermenting a transformed host cell (e.g., a bacterial host cell as contemplated herein) which comprises an expression vector (as contemplated herein) which in turn comprises a nucleic acid molecule encoding the disclosed peptides, polypeptides, or variants thereof (as contemplated herein), wherein cultivation occurs under conditions which cause expression of the peptides, polypeptides, or variants; and isolating, separating, or purifying the peptides, polypeptides, or variants. The transformed bacteria may be cultivated or fermented using methods known in the art in order to express the peptides, polypeptides, or variants. An exemplary isolation, separation, or purification method may include one or more of the following steps: a cell disruption step, a clarification step (e.g., via centrifugation or filtration), a chromatographic separation step, a dialysis step, and a precipitation step.

In some other embodiments, the polypeptide can be chemically synthesized. Synthesis of a polypeptide can be performed using solution-phase techniques, solid-phase methods, or other suitable methods of polypeptide synthesis.

Methods

Provided are methods for the use of the polypeptides and compositions disclosed herein. Such methods can comprise application of one or more of the polypeptides described herein to a subject. Methods described herein can delay the onset of, reduce the occurrence of, or ameliorate an age-related disease or condition or age-associated disorder.

Methods described herein can delay the onset of, reduce the occurrence of, reduce the appearance of, or ameliorate a disease, a disorder, or a condition associated with the accumulation of senescent cells. A disease or disorder associated with the accumulation of senescent cells can be age related. In some cases, the disease or disorder can worsen over time if untreated.

A polypeptide or composition can be applied or administered to a subject to treat a condition directly or indirectly influenced by skin health. Such a method can comprise administering to the subject a compound that promotes skin health or applying topical treatment to the skin.

An age-associated disorder can comprise a biological progression of events that occurs during a disease process that can affect the body, which can mimic or substantially mimic all or part of the aging events which occur in a normal subject. In some cases, this biological progression of events can occur over an accelerated time frame.

An age-related disease or condition or age-associated disorder can relate to regular processes in the body, such as movement and eating capacity.

In some cases, the age-related disease or condition or age-associated disorder can be a disease, condition, or disorder affecting the skin, such as a skin disorder or a dermatosis, which can comprise wrinkles, lines, dryness, itchiness, spots, age spots, bedsores, ulcers, cancer, dyspigmentation, infection (e.g., fungal infection), or a reduction in a skin property such as clarity, texture, elasticity, color, tone, pliability, firmness, tightness, smoothness, thickness, radiance, luminescence, hydration, water retention, skin barrier, evenness, laxity, or oiliness, or other dermatoses. In some instances, the age-related disease or condition or age-associated disorder is hyperpigmentation of the skin. In some instances, the hyperpigmentation disorder is melasma, age spots, lentigines, and/or progressive pigmentary purpura. In some instances, the hyperpigmentation is a result of sun damage, inflammation, hormone changes, or skin injuries. In some instances, the hyperpigmentation occurs after a cosmetic procedure, including but not limited to a laser treatment, a light treatment, or a chemical peel; administration of an antibiotic, an oral contraceptive, or a photosensitizing drug; or application of a topical agent. In some instances, the hyperpigmentation is a result of excess production of melanin.

In some instances, treatment of the age-related disease or condition or age-associated disorder with the methods, systems and compositions disclosed herein results in lightening, increasing luminescence, brightening, evening, smoothing and/or firming of the skin's appearance. In some instances, treatment with the methods, systems, and compositions disclosed herein improves the epidermal barrier, skin hydration level, skin water retention, appearance of wrinkles, smoothness, firmness, elasticity, appearance of radiance and luminosity, and/or improves or maintains the ceramide level in the skin. In some instances, the effect of treatment with the methods, systems, and compositions disclosed herein is assessed by measuring skin moisture content, trans-epidermal water loss (TEWL), dermal thickness and echogenicity, intracutaneous analysis, skin viscoelastic properties, or skin surface profile. In some instances, the effect of treatment with the methods, systems, and compositions disclosed herein assesses for reduction in appearance of lines/wrinkles, appearance of skin tone (evenness), appearance of pores, appearance of texture/smoothness, firmness (visual), elasticity (tactile), epidermal barrier, skin roughness, skin hyperpigmentation, or overall appearance. In some instances, the effect of treatment with the methods, systems, and compositions disclosed herein is measured using an instrument, including but not limited to a corneometer for measuring skin moisture content/hydration, a VapoMeter for measuring the trans-epidermal water loss (TEWL), an ultrasound measuring dermal thickness (density) and echogenicity, a non-invasive optical skin imaging instrument for measuring skin evenness and chromophore mapping, a cutometer using suction for measuring viscoelastic properties of the skin (firmness and elasticity), skin profilometry, multi-spectral analysis, and colorimetry for measuring skin surface profile, lines, and wrinkles In some instances, the treatment of the age-related disease or condition or age-associated disorder results in the reduction of the appearance of wrinkles or skin pigmentation by, for example, 10%, 20%, 30%, 40%, 50%, 60%, 70%, 80%, 90%, 95% or 99%. In some instances, the instrumental measurement shows an improvement in at least one of appearance of lines/wrinkles, appearance of skin tone (evenness), appearance of pores, appearance of texture/smoothness, firmness (visual), elasticity (tactile), epidermal barrier, skin roughness, skin radiance, or overall appearance by at least 1%, 2%, 3%, 4%, 5%, 6%, 7%, 8%, 9%, 10%, 11%, 12%, 13%, 14%, 15%, 16%, 17%, 18%, 19%, or 20% after the use of the composition as compared to before the use of the composition. In some instances, the improvement is presented as a mean percentage improvement (MPI) compared to baseline before the use of the composition. In some instances, MPI is at least 1%, 2%, 3%, 4%, 5%, 6%, 7%, 8%, 9%, 10%, 11%, 12%, 13%, 14%, 15%, 16%, 17%, 18%, 19%, or 20% after the use of the composition as compared to before the use of the composition. In some instances, the measurements are taken at 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 5 months, 6 months, or one year after the use of the composition. In some instances, the effect of the treatment is assessed by an expert in skin conditions, disorders, or diseases who analyzes one or more of the skin measurements. In some instances, the effect of the treatment is assessed by the user themselves. In some instances, at least 10%, 20%, 30%, 40%, 50%, 60%, 70%, 80%, or 90% of the users may report an improvement in at least one of skin barrier, skin roughness, skin radiance, appearance of lines/wrinkles, appearance of skin tone (evenness), appearance of pores, appearance of texture/smoothness, firmness (visual), elasticity (tactile), or overall appearance after using the methods, systems, and compositions disclosed herein. In some instances, at least 10%, 20%, 30%, 40%, 50%, 60%, 70%, 80%, or 90% of the users may report an improvement in hydration of the skin. In some instances, at least 10%, 20%, 30%, 40%, 50%, 60%, 70%, 80%, or 90% of the users may report an improvement in skin barrier function.

In some instances, the methods, systems, and compositions provided herein may reduce hyperpigmentation of the skin. In some instances, hyperpigmentation is associated with excess production of melanin. In some instances, the methods, systems, and compositions provided herein reduces the excess production of melanin. In some instances, the methods, systems, and compositions provided herein reduce the presence of melanin pigment in the skin. In some instances, the methods, systems, and compositions provided herein reduce the expression levels of proteins involved in melanogenesis, including tyrosinase, melanocyte inducing transcription factor (MITF) and dopachrome tautomerase (DCT), by the cells in the treated skin. In some instances, the methods, systems, and compositions provided herein result in reduction of tyrosinase activity, reduction of the expression or activation of tyrosinase, scavenging of the intermediate products of melanin synthesis, reducing the transfer of melanosomes to keratinocytes, reduction of existing melanin content, or reduction in melanocyte activity or viability.

In some cases, the methods, systems, and compositions provided herein may reduce cutaneous inflammation. In some cases, the methods, systems, and compositions provided herein may reduce expression levels of proteins involved in inflammation, interferon-gamma (IFN-γ) and interleukin 10 (IL-10), by the cells in the treated skin.

In some embodiments, the compositions described herein are administered once per day, twice per day, three times per day or more. In some embodiments, the compositions described herein are administered twice daily administration, e.g., morning and evening. In some embodiments, the compositions described herein are administered daily, every day, every alternate day, five days a week, once a week, every other week, two weeks per month, three weeks per month, once a month, twice a month, three times per month, or more. In some embodiments, the compositions described herein are administered for at least 1 week, 2 weeks, 3 weeks, 1 month, 2 months, 3 months, 4 months, 5 months, 6 months, 7 months, 8 months, 9 months, 10 months, 11 months, 12 months, 18 months, 2 years, 3 years, 4 years, 5 years, or longer. In some embodiments, the composition is directed to be applied as a smooth layer onto clean, dry skin on face and/or neck in the morning and the evening. In some embodiments, formulation is a daily essential topical supplement scientifically formulated to improve skin resilience and strengthen epidermal barrier for long-lasting health of the skin. In some embodiments, the user applies the compositions described herein comprising at least one of the polypeptides to the face and/or neck. In some embodiments, the composition is directed to be applied to the skin on the body. In some embodiments, the compositions described herein is used in conjunction with other topical compositions, such as a UV blocker. In some embodiments, the compositions described herein is applied before, together with, or after the application of the other topical composition. In some embodiments, the composition comprises a UV blocker.

A polypeptide or composition can be applied topically, i.e., to skin, to delay the onset of, reduce the occurrence of, or ameliorate the disease, condition, or disorder affecting the skin.

An age-related disease or condition or age-associated disorder can be caused by UV damage, DNA damage, ATRX foci accumulation in cell nuclei, increased p16 expression, increased senescence-associated β-galactosidase activity, accumulation of senescent cells in the tissue, increased SASP production, chemically induced senescence, chronological aging, decreased hyaluronic acid production, decreased expression of sirtuin 6, altered insulin-like growth factor-1 (IGF-I) pathway signaling, increased production of matrix metallopeptidase 1 (MMP1), thin epidermal layer of the skin, or genetic variants. In some instances, the age-related disease or condition or age-associated disorder is initiated or exacerbated by a therapeutic regimen, for example, a side effect of a therapeutic drug. An age-related disease or condition or age-associated disorder can affect the health or appearance of skin directly or indirectly. Topical application of a polypeptide or composition herein can improve the health or appearance of skin in some such cases.

An age-related disease or condition or age-associated disorder can comprise a cell proliferative disorder. A cell-proliferative disorder can affect the health or appearance of the skin. In some cases, a treatment administered for a cell-proliferative disorder, such as chemotherapy or radiation can affect the health or appearance of the skin. Topical application of a polypeptide or composition herein can improve the health or appearance of skin in some such cases.

Also provided herein are methods for treating the skin of a subject comprising administering to a subject a composition that can promote a decrease in a number of senescent cells in a tissue or organism, inducing a pro-apoptotic state in the treated cells, inducing SIRT6 expression, preventing DNA-induced senescence, and/or enhancing DNA repair capacity. In some cases, a skin disease such as a dermatological disease or condition can comprise skin sagging or wrinkling, accumulation of senescent cells in the tissue, decreased epidermal thickness, decreased collagen production, increased MMP-1 production, decreased DNA repair capacity, decreased SIRT6 expression, skin disorganization, a thin epidermal layer of the skin, inflammation, a senescence-associated secretory phenotype, or stem cell exhaustion of the skin.

Methods can comprise administering to the subject a composition comprising a polypeptide that can promote a significant decrease in the number of senescent cells in the tissue or organism. A decrease in the number of senescent cells can comprise a pro-apoptotic state in the treated cells, inducing SIRT6 expression, preventing DNA-induced senescence, or enhancing DNA repair capacity. In some cases, the number of senescent cells in a sample, a portion of a subject (e.g., the facial skin of a subject), and/or a subject can be reduced by at least 10%, at least 20%, at least 30%, at least 40%, at least 50%, at least 60%, at least 70%, at least 80%, or at least 90%.

A polypeptide or compositions can be applied or administered to a cell, tissue, or subject. In some cases, application or administration of a polypeptide can result in a senotherapeutic effect in a cell, tissue, or subject. In some cases, a polypeptide can be administered to a subject, applied topically to a subject, or incubated with cultured cells to provide a senotherapeutic effect.

A cell can be a cultured cell or a cell isolated from a subject or from a cell line. Some examples of cultured cells can comprise a keratinocyte or a fibroblast or a melanocyte. A cell can be wild type or can be genetically modified. Some genetic modifications can promote senescence, such as genetic modifications in the p53/p21 pathway, the p16/RB pathway, the, a mRNA or miR gene, among other RNA classes. In some cases, application of a polypeptide or composition to a cell can reduce senescence in the cell. In some cases, cells may comprise cells in vivo or in situ in an organism, including but not limited to animals, *C. elegans*, and humans.

A tissue can be a tissue which is a tissue of a subject or a tissue which has been isolated from a subject, i.e., ex vivo. In some cases, a tissue can be artificially grown. A tissue can comprise skin, and examples of tissues can comprise healthy skin, diseased skin, aged skin, or scalp. In some cases, application of a polypeptide or composition to a tissue can reduce senescence in one or more cells of the tissue or the entire tissue. In some cases, tissue may comprise tissue in vivo or in situ in an organism, including but not limited to animals, *C. elegans*, and humans.

In cases where the subject is a human, the subject may be of any age. In some cases, the subject has an age-related disease or condition or age-associated disorder, is at risk for an age-related disease or condition or age-associated disorder, or is healthy. A subject can be male or female.

A method can comprise topical application of a polypeptide or composition. Topical application can comprise rubbing, spraying, dipping, dabbing, or otherwise applying a polypeptide or composition to skin or mucosa.

EXAMPLES

Example 1

Primary fibroblasts isolated from Progeria patients can constitute a genetic model of early aging and cellular senescence in humans. Primary fibroblasts from Progeria patients were cultured in DMEM (Dulbecco's Modified Eagle's Medium) supplemented with 10% v.v. fetal bovine serum (FBS), and 1% v.v. of penicillin/streptomycin solution (1,000 U·mL−1). Cells were kept in a 5% $CO_2$, 37° C. and 95% humidity atmosphere. After expansion, these cells were seeded in 96-well plates (1,000 cells per well) and, 6 hours after plating, were incubated with individual polypeptides from a proprietary library at 50 μM for 48 hours. Negative control comprised untreated cells, which received vehicle only; positive control group comprised cells incubated with 10 μM ABT-263, a senolytic compound for the same period. After incubation, relative cellular senescence (assessed by the activity of senescence associated B-galactosidase staining relative to untreated control) was analyzed as shown in FIG. 1, in which the Y axis indicates the total number of cells in the well (normalized to the untreated control), and the X axis represents senescence associated B-galactosidase staining intensity/nuclei (i.e., senescence level), also normalized to negative control. Three independent experiments including three technical replicates were performed. Polypeptides which promoted a significant decrease of cellular senescence to below 75% that of the untreated control sample were considered positive hits.

A total of 764 polypeptides were tested, among which 56 promoted a decrease in cellular senescence to below 75% that of the untreated control sample. Therefore, they were considered as positive hits, and putative senotherapeutic compounds. ABT-263, which was considered a positive control in the experiment, also promoted significant reduction of cellular senescence, but also cellular toxicity. This observation confirmed the senolytic characteristic of ABT-263, as well as the senotherapeutic potential of some of the tested polypeptides (FIG. 1).

Example 2

Primary fibroblasts isolated from 3 healthy chronologically aged patients were used. Cells were cultured in DMEM (Dulbecco's Modified Eagle's Medium) supplemented with 10% v.v. fetal bovine serum (FBS), and 1% v.v. of penicillin/streptomycin solution (1,000 U·mL−1). Cells were kept in a 5% $CO_2$, 37° C. and 95% humidity atmosphere. After expansion, these cells were seeded in 96-well plates (4,000 cells per well) and, 6 hours after plating the cells were treated with one of 4 senotherapeutic polypeptides (Peptide 14, Peptide 13, Peptide 15, and Peptide 16) and incubated for 48 hours. Each polypeptide was tested at 6 different concentrations: 50 μM, 25 μM, 12.5 μM, 6.25 μM, 3.12 μM, and 1.56 μM, except for Peptide 16, which was tested at 5 different concentrations: 25 μM, 12.5 μM, 6.25 μM, 3.12 μM, and 1.56 μM. A negative control comprised untreated cells, which received vehicle only. After incubation, relative cellular senescence (assessed by the activity of senescence associated B-galactosidase staining relative to untreated control) was analyzed (FIG. 2, panels A-D), in which the Y axis indicates the relative senescence levels normalized to untreated control. Each column corresponds to a different concentration of a polypeptide. Three independent experiments (biological replicates) including three technical replicates were performed. Data was analyzed using Analysis of Variance (ANOVA) and a Bonferroni post-hoc tests. Statistical significance was determined as p values equal or lower than 0.05.

Figure 2:
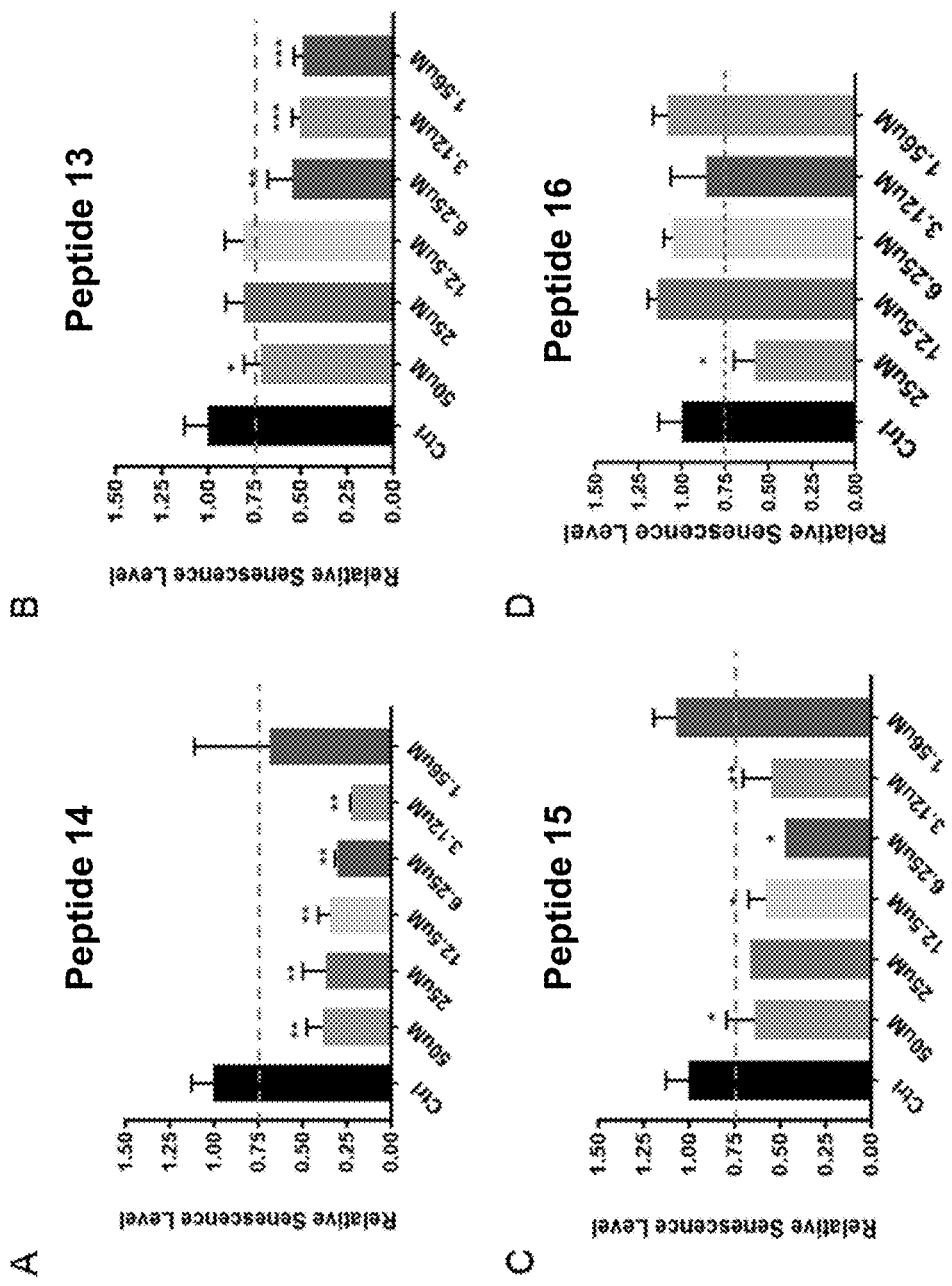
FIG. 2 illustrates the senotherapeutic effects of four polypeptides, Peptide 14 (panel A), Peptide 13 (panel B), Peptide 15 (panel C), and Peptide 16 (panel D), on senescent fibroblasts. *$p<0.05$; $p<0.01$; *$p<0.001$.

All polypeptides presented senotherapeutic potential in at least one of the tested concentrations, evidenced by the significant reduction of cellular senescence compared to untreated control. *$p<0.05$; $p<0.01$; *$p<0.001$ compared to untreated control (ctrl) (FIG. 2, panels A-D).

Example 3

Figure 3:
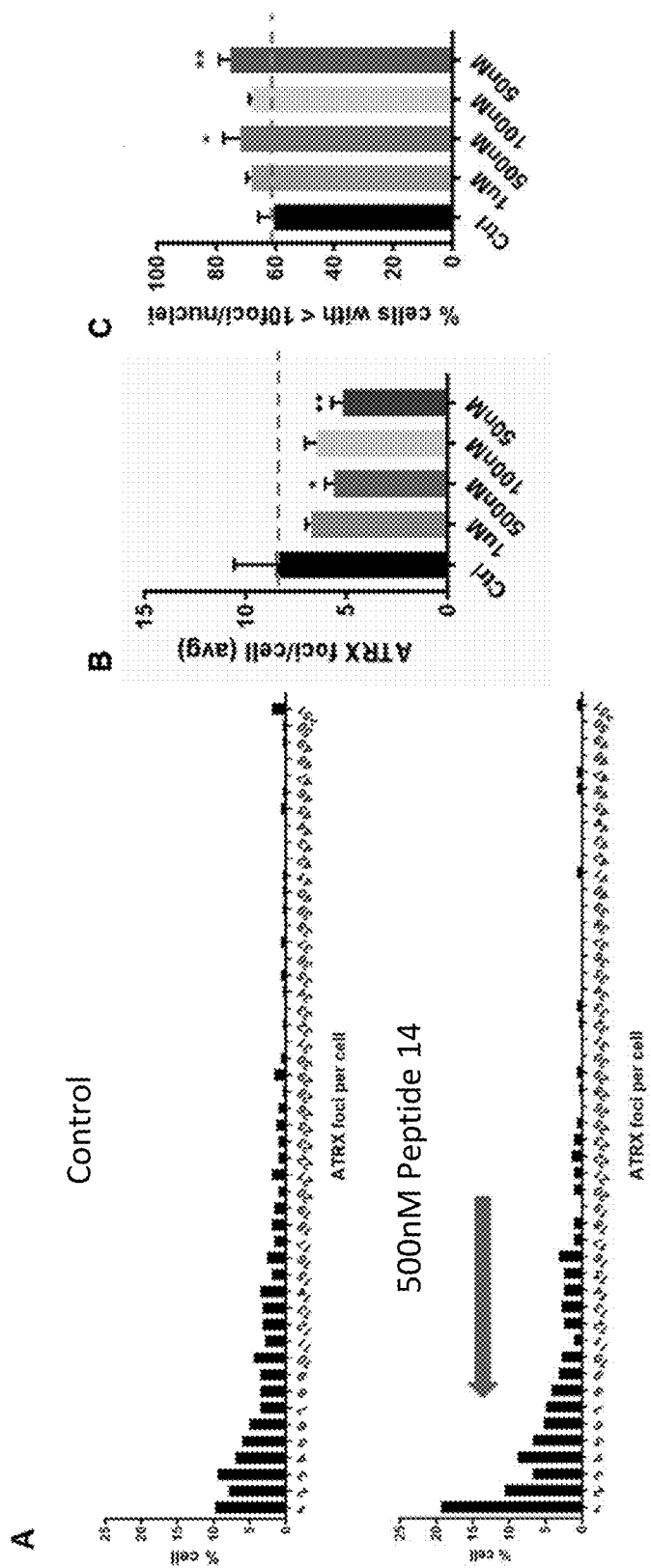
FIG. 3 illustrates a senotherapeutic effect of a polypeptide which promotes a higher number of cells with less ATRX foci/nuclei (panel A), a lower average of ATRX foci/nuclei (panel B), and a higher number of cells with less than 10 ATRX foci/nuclei (panel C). *$p<0.05$; **$p<0.01$.

ATRX is a chromatin remodeling enzyme, which contributes to the formation of senescence associated heterochromatic foci. It increasingly accumulates in nuclear foci during senescence. Therefore, it constitutes a marker of cellular senescence. To investigate whether Peptide 14 decreased levels of cellular senescence, ATRX foci were analyzed in Peptide 14 treated (1 μM, 500 nM, 100 nM, and 10 nM) and untreated cells. To do so, primary fibroblasts isolated from 3 healthy chronologically aged (elder) donors were used. These cells were cultured in DMEM (Dulbecco's Modified Eagle's Medium) supplemented with 10% v.v. fetal bovine serum (FBS) and 1% v.v. of penicillin/streptomycin solution (1,000 U·mL−1). Cells were kept in a 5% $CO_2$, 37° C. and 95% humidity atmosphere. After expansion, these cells were seeded in 96-well plates (4,000 cells per well) and, 6 hours after plating, were incubated for 48 hours with the Peptide 14 polypeptide in the aforementioned concentrations. A negative control comprised untreated cells, which received vehicle only. After incubation, relative cellular senescence was assessed. Briefly, immunostaining was performed by fixing, permeabilizing, and incubating the cells with anti-ATRX antibody, followed by secondary antibody. The number of nuclei and stained ATRX foci were counted. Panel A of FIG. 3 shows a representative graph showing the number of cells (Y axis) presenting a specific amount of ATRX foci/cell, represented as columns (X axis). The upper graph depicts untreated cells, while the lower graph depicts cells treated with Peptide 14 at 500 nM. Panel B of FIG. 3 shows the average number of ATRX foci/nuclei of fibroblasts treated with different conditions of Peptide 14 (columns). Panel C of FIG. 3 shows the percentage of cells presenting less than 10 ATRX foci/nuclei among fibroblasts treated with different conditions of Peptide 14 (columns). Three independent experiments (biological replicates) including three technical replicates were performed. Data in panels B and C of FIG. 3 were analyzed using ANOVA and Bonferroni post-hoc tests. Statistical significance was determined as p values equal or lower than 0.05.

Peptide 14 treatment significantly decreased ATRX foci/nuclei, when used at 500 nM and 50 nM, compared to untreated cells. In the same concentrations, Peptide 14 also increased the number of cells which presented less than 10 foci/nuclei. *$p<0.05$; $p<0.01$ compared to untreated control (ctrl) (FIG. 3**).

Example 4

Figure 4:
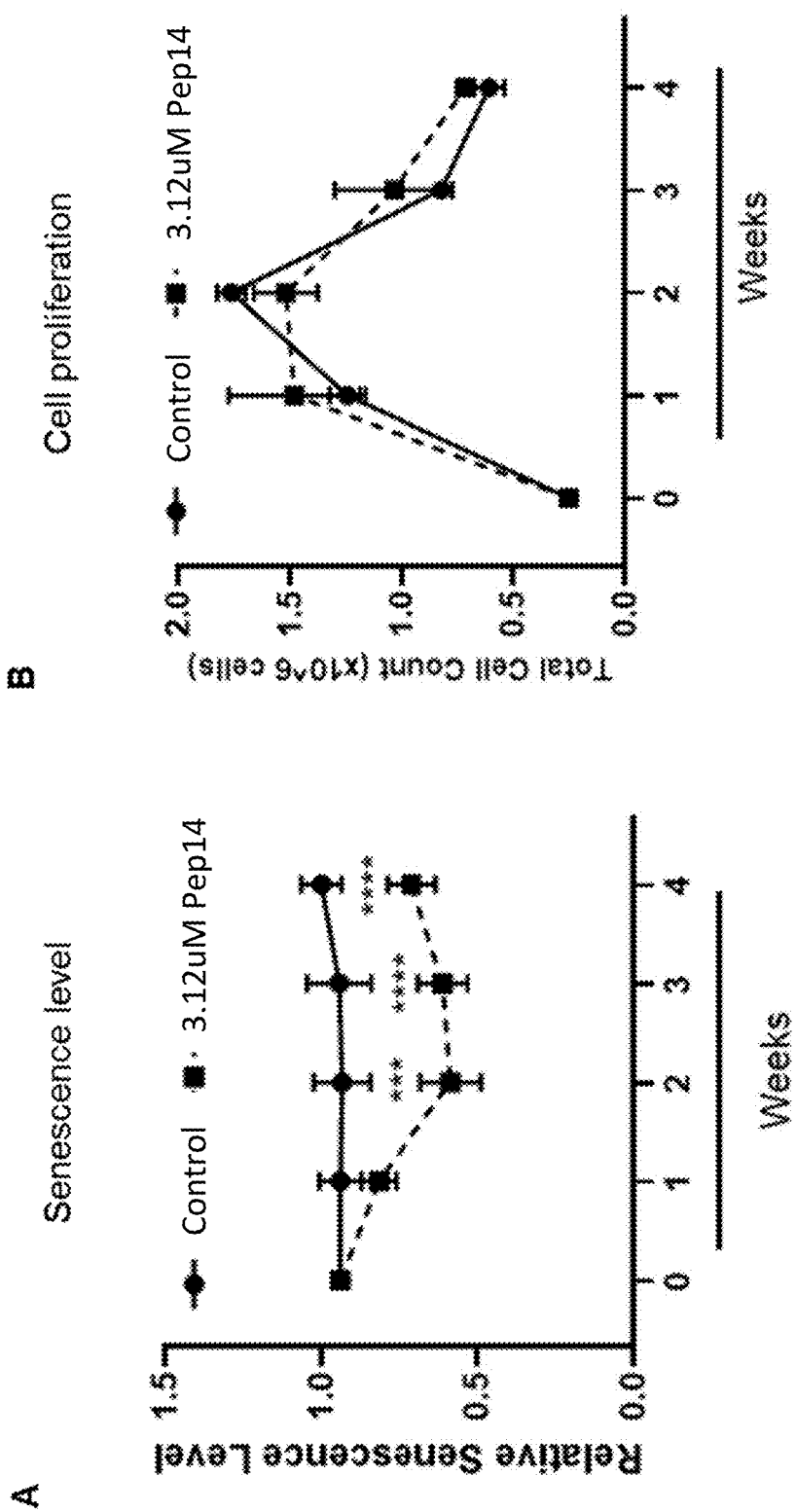
FIG. 4 illustrates the effect of a senotherapeutic polypeptide which can decrease the number of senescent fibroblasts in a cell population during a 3-week long exposure keeping the senotherapeutic effect for at least one week after treatment (panel A) without inducing cell toxicity or significantly affecting cellular proliferation during this period (panel B). *$p<0.001$; **$p<0.0001$.

Human primary fibroblasts isolated from 3 healthy chronologically aged (elder) donors were used. These cells were cultured in DMEM (Dulbecco's Modified Eagle's Medium) supplemented with 10% v.v. fetal bovine serum (FBS), and 1% v.v. of penicillin/streptomycin solution (1,000 U·mL−1). Cells were kept in a 5% $CO_2$, 37° C. and 95% humidity atmosphere. After expansion, these cells were seeded in T-75 flasks (250,000 cells per flask) and, 6 hours after plating, were incubated for 3 weeks (21 days) with Peptide 14 at 3.12 μM. A negative control comprised untreated cells, which received vehicle only. Day 0 was defined as the day cells started to be treated with Peptide 14. No Peptide 14 treatment was performed between days 21 and 28. Weekly, cellular senescence was assessed according to senescence associated β-galactosidase staining levels. Data was normalized to untreated group and plotted (FIG. 4, panel A). Cellular proliferation was also determined weekly. At days 7, 14, 21, and 28, cells were trypsinized and counted (FIG. 4, panel B). After counting, 250,000 cells were plated in new T-75 flasks. Three independent experiments (biological replicates) including three technical replicates were performed. Data was analyzed using T-test. Statistical significance was determined as p values equal or lower than 0.05.

Peptide 14 promoted a significant decrease (*p<0.001; p<0.0001) of cellular senescence beginning at the second week. After 21 days of treatment, the senotherapeutic effect of Peptide 14 was maintained for at least 7 days after polypeptide removal (between experimental days 21 and 28). No significant differences were observed regarding cell proliferation comparing Peptide 14 treated group and untreated control (FIG. 4**).

Example 5

Figure 5:
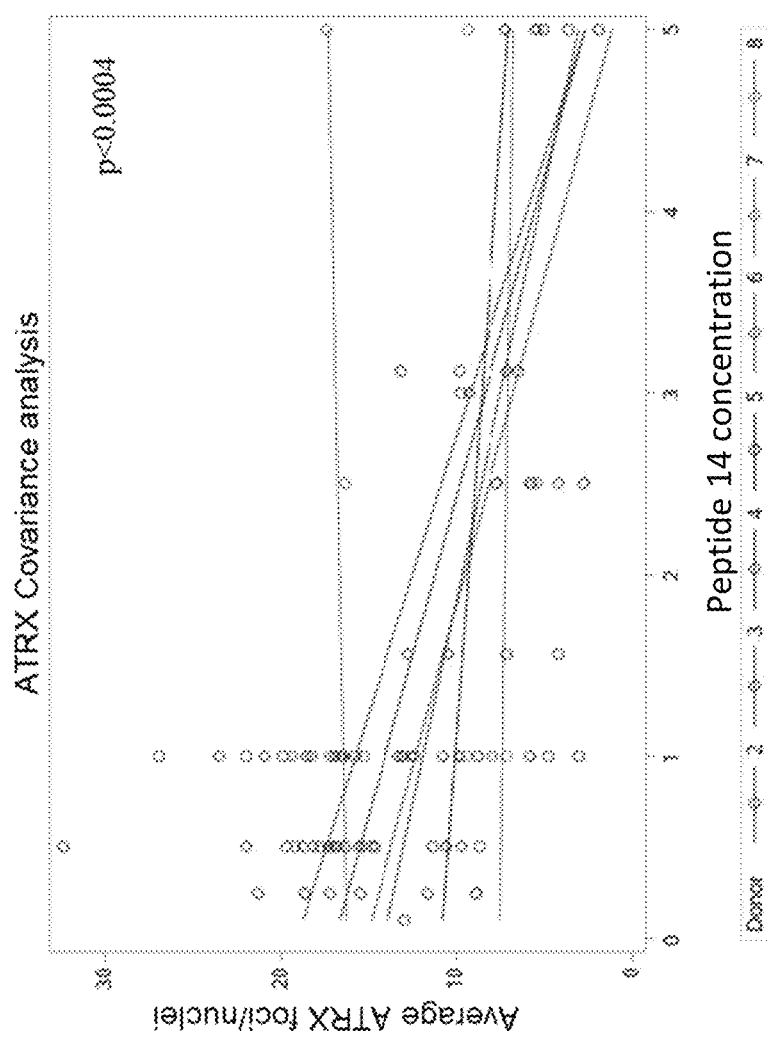
FIG. 5 illustrates that treatment with a polypeptide can promote a dose response decrease in cellular senescence, as measured by average ATRX foci accumulation per cell in cells derived from multiple donors.

Primary fibroblasts isolated from 7 healthy chronologically aged patients were used (patients were aleatory identified as patient 2, 3, 4, 5, 6, 7, or 8). These cells were cultured in DMEM (Dulbecco's Modified Eagle's Medium) supplemented with 10% v.v. fetal bovine serum (FBS), and 1% v.v. of penicillin/streptomycin solution (1,000 U·mL−1). Cells were kept in a 5% $CO_2$, 37° C. and 95% humidity atmosphere. After expansion, these cells were seeded in 96-well plates (4,000 cells per well) and, 6 hours after plating, were incubated for 48 hours with Peptide 14 at 5 different concentrations: 25 μM (concentration 5), 12.5 μM (concentration 4), 6.25 μM (concentration 3), 3.12 μM (concentration 2), and 1.56 μM (concentration 1). A negative control comprised untreated cells (concentration 0), which received vehicle only. After incubation, relative cellular senescence was determined according to the average number of ATRX foci/nuclei quantified following ATRX immunostaining. Seven independent experiments (biological replicates) including three technical replicates were performed. Data was analyzed using a covariance test. Statistical significance was determined as p-values equal or lower than 0.05 (FIG. 5).

Covariance analysis shows that the number of ATRX foci/nuclei was significantly reduced following Peptide 14 treatment. Peptide 14 efficacy followed a dose-response pattern, with concentration and ATRX foci/nuclei being significantly correlated (p<0.0004) (FIG. 5).

Example 6

Cellular senescence may be caused by several different stimuli. In order to assess whether Peptide 14 was effective against UVB-induced and chemically-induced senescence, human primary fibroblasts isolated from 3 healthy donors were used. These cells were cultured in DMEM (Dulbecco's Modified Eagle's Medium) supplemented with 10% v.v. fetal bovine serum (FBS), and 1% v.v. of penicillin/streptomycin solution (1,000 U·mL−1). Cells were kept in a 5% $CO_2$, 37° C. and 95% humidity atmosphere. After expansion, these cells were seeded in 96-well plates (4,000 cells per well) and, 6 hours after plating, were submitted to either etoposide (20 μM) treatment for 24 hours, or exposed twice to 0.05 J/cm² of UVB radiation. Each UVB exposure corresponds to approximately 1 to 3 hours of daily sun exposure in April of major cities around the world (e.g. Auckland, NZ; Los Angeles, US; and Brasilia, BR). After the different senescence induction protocols, etoposide treated cells were incubated with Peptide 14 at 5 μM, 2.5 μM, or 1 μM for 48 hours. UVB exposed cells were treated with Peptide 14 at 5 μM for 48 hours. A negative control comprised untreated cells, which were submitted to stress, but received vehicle only. After incubation, relative cellular senescence (assessed by the activity of senescence associated β-galactosidase staining relative to untreated control) was analyzed and plotted in column graphs. ATRX foci were also assessed following ATRX immunofluorescence staining. Graphs were built using the average ATRX foci detected per nuclei. Three independent experiments (biological replicates) including three technical replicates were performed. Data was analyzed using with either t-test or ANOVA followed by a Bonferroni post-hoc test. Statistical significance was determined as p-values equal or lower than 0.05 (FIG. 6).

Figure 6:
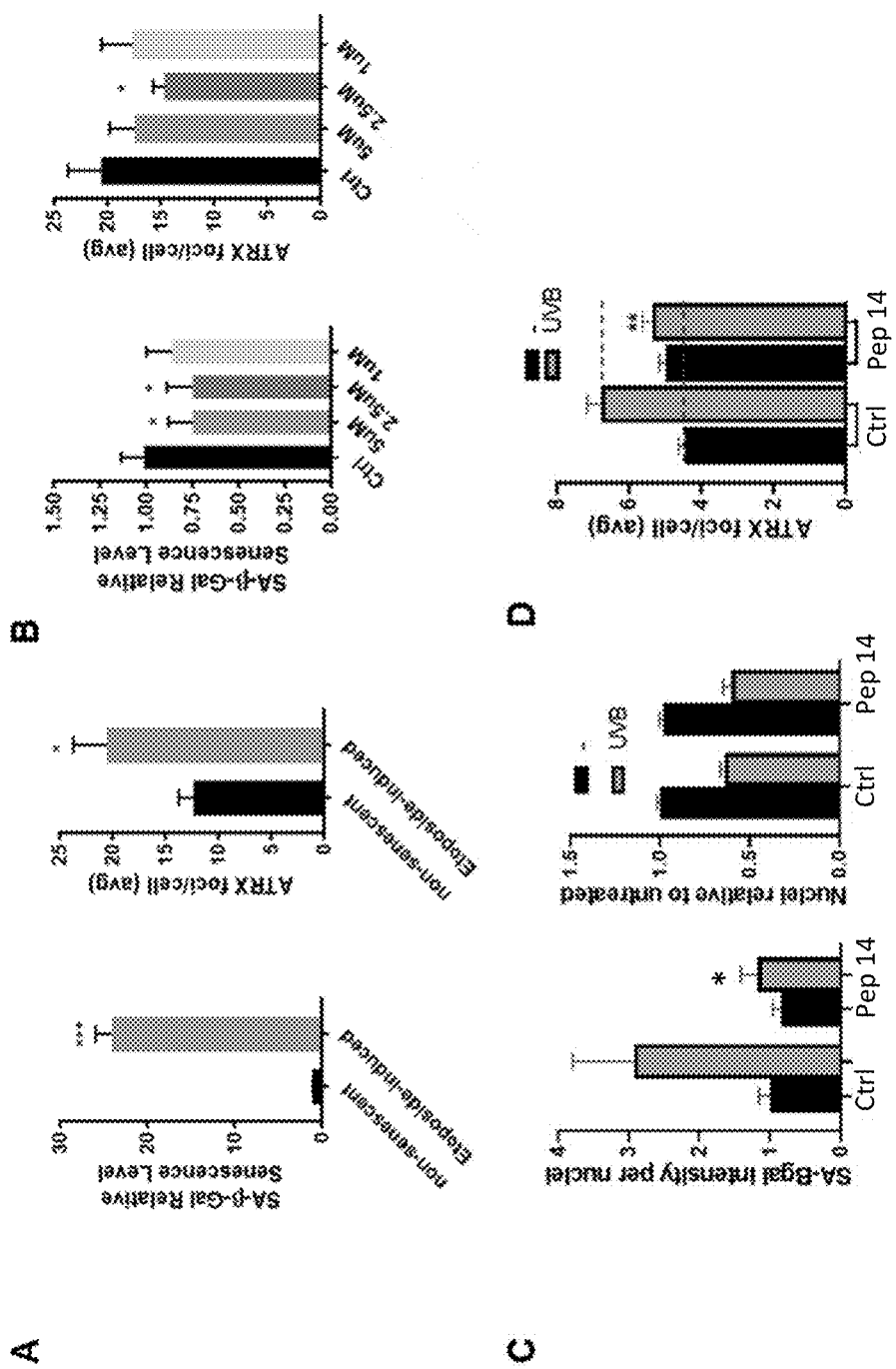
FIG. 6 illustrates that cellular senescence can be induced in fibroblasts with exposure to etoposide (panel A), treatment of etoposide-induced senescent cells with a polypeptide can result in reduced senescence (panel B), cellular senescence can be induced by UVB exposure (panel C), and treatment of a UVB treated sample with a polypeptide can result in reduced senescence (panel D). *$p<0.05$; $p<0.01$; *$p<0.001$.

Etoposide treatment promoted a significant increase in cellular senescence level (p<0.001), and also a significant increase of ATRX foci nuclear accumulation (represented as the average number of ATRX foci/cell; p<0.05) (FIG. 6, panel A). When etoposide-stressed cells were treated with 2.5 μM or 5 μM of Peptide 14, senescence associated β-galactosidase staining was significantly reduced (*p<0.05) (FIG. 6, panel B, left graph). Average ATRX foci/cell was also significantly reduced when etoposide-exposed cells were treated with 2.5 μM Peptide 14, as shown in the right graph of panel B of FIG. 6. UVB exposure also promoted significant increase in cellular senescence, as assessed by senescence associated β-Galactosidase staining, 5 μM Peptide 14 treatment being able to significantly prevent cellular senescence (*p<0.05), as shown in the left graph of panel C of FIG. 6. Treatment with Peptide 14 did not significantly alter cell number, as shown in the right graph of panel C of FIG. 6. UVB exposure promoted significant increase in the average number of ATRX foci per nuclei, and 5 μM Peptide 14 treatment significantly prevented cellular senescence, leading to significantly reduced ATRX foci/nuclei, compared to UVB treated samples which did not receive Peptide 14 (*p<0.01) (FIG. 6, panel D).

Example 7

Human primary fibroblasts and keratinocytes isolated from healthy elder donors were used to build human skin equivalents. Those skin equivalents were treated with 0.01% w.v. Peptide 14 for 5 days and were characterized according to levels of senescence using senescence associated B-galactosidase staining, overall structure, as indicated by epidermal thickness. Quality assessment based several parameters was performed by blind analysts. The observed parameters include general organization of cell layers, as well as the thickness of the horny layer, among other aspects and were shown to decrease with aging and senescence level. The assessment had a maximum score of 28, where higher score correlated with decrease in age and senescence. A minimal score of 19 was required for batch use. This score was validated internally and shown to decrease with age/ senescence of the skin equivalents or cultured cells. Furthermore, skin equivalents were characterized according to the expression of specific genes by reverse transcription-quantitative polymerase chain Reaction (RT-qPCR). Following treatment, epidermis and dermis were processed for RT-qPCR separately. For epidermis samples, glyceraldehyde 3-phosphate dehydrogenase (GAPDH; ubiquitously expressed); p16 (associated to senescence), IL-8 (linked to irritation), and Ki-67 (associated to cell proliferation) were analyzed. For dermis samples, glyceraldehyde 3-phosphate dehydrogenase (GAPDH; ubiquitously expressed); p16 (associated to senescence), IL-8 (linked to irritation), Ki-67 (associated to cell proliferation); hyaluronic synthase 2 (HAS-2; associated with hyaluronic acid production), and matrix metalloprotease 1 (MMP1; associated to extracellular matrix protein degradation) were analyzed. CT values were analyzed using the $2^{-\Delta\Delta Ct}$ method. Average mRNA expression was normalized to GAPDH ($\Delta$Ct) and to the negative control group ($\Delta\Delta$Ct). Negative controls received formulation only. Three independent experiments were performed with three technical replicates. Data was analyzed using T-test. Statistical significance was determined as p-values equal or lower than 0.05 (FIG. 7)

Figure 7:
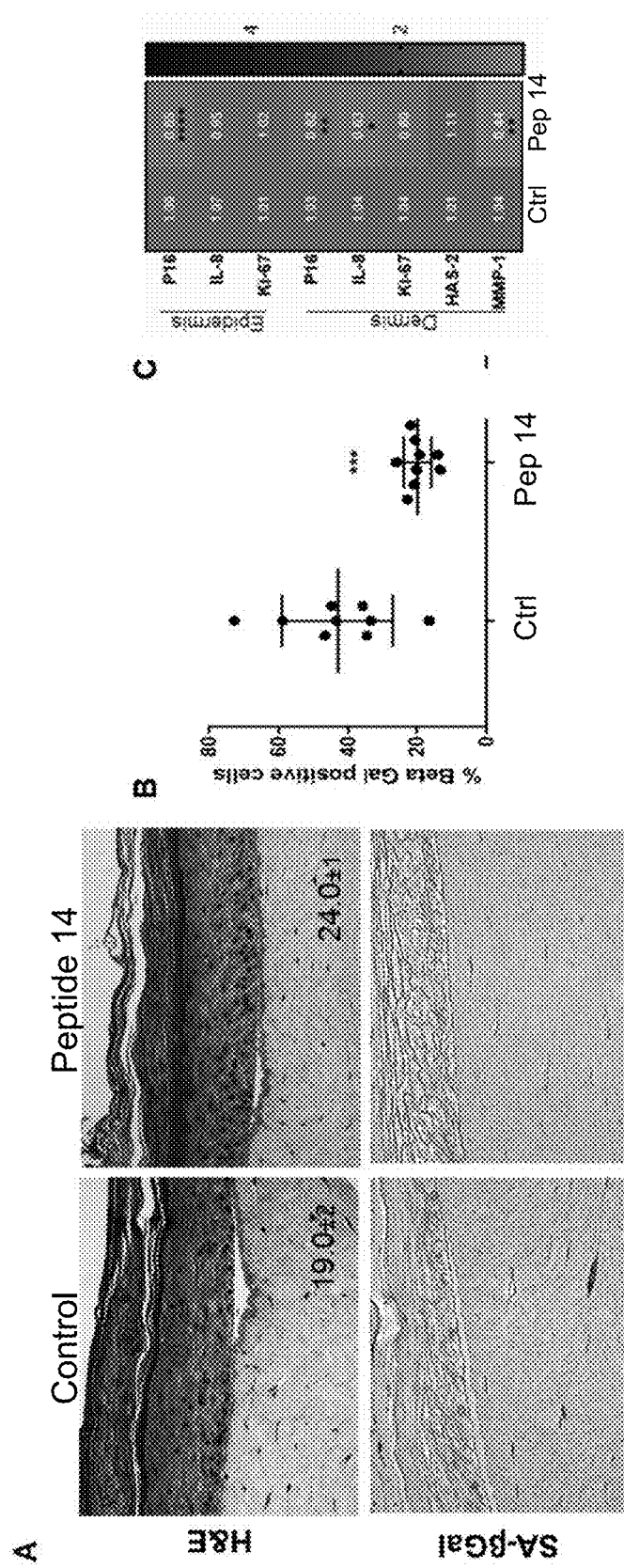
FIG. 7 illustrates that human skin equivalents treated with a polypeptide can show higher quality according to an overall structure analysis score (panel A), that human skin equivalents treated with a polypeptide can comprise significantly fewer senescent cells than untreated human skin equivalents (panels A and B), and altered gene expression in which p16 can have a significantly lower expression in polypeptide treated epidermis and dermis, compared to untreated control; and IL-8 and MMP-1 were significantly less expressed in polypeptide-treated dermis, compared to untreated counterparts (panel C). *$p<0.05$; $p<0.01$; *$p<0.001$; ****$p<0.0001$.

Peptide 14 treatment of human skin equivalents promoted increased skin equivalent score (Peptide 14 group 24±1 versus 19.0±2), as shown in panel A of FIG. 7, suggesting treatment safety, tolerability and beneficial effects. This is in contrast to other senolytic agents that may have safety and tolerability issues. See, e.g., Tse et al., Cancer Res. 68:3421 (2008); Wilson et al., Lancet Oncol. 11:1149 (2010). In addition, treatment promoted a significant decrease in senescence associated β-galactosidase staining (*p<0.001), as shown in panel A of FIG. 7 and panel B of FIG. 7, corroborating the senotherapeutic effect of the polypeptide. Furthermore, Peptide 14 treatment led to significant decrease of p16 in epidermis (p<0.0001) and dermis (p<0.01); decreased expression of IL-8 in the dermis (*p<0.5); and decreased expression MMP-1 in the dermis (p<0.01). The data corroborates the senotherapeutic potential of Peptide 14, safety and tolerability, as well as the beneficial effects of the polypeptide to skin gene expression, as shown in panel C of FIG. 7**.

Example 8

Figure 8:
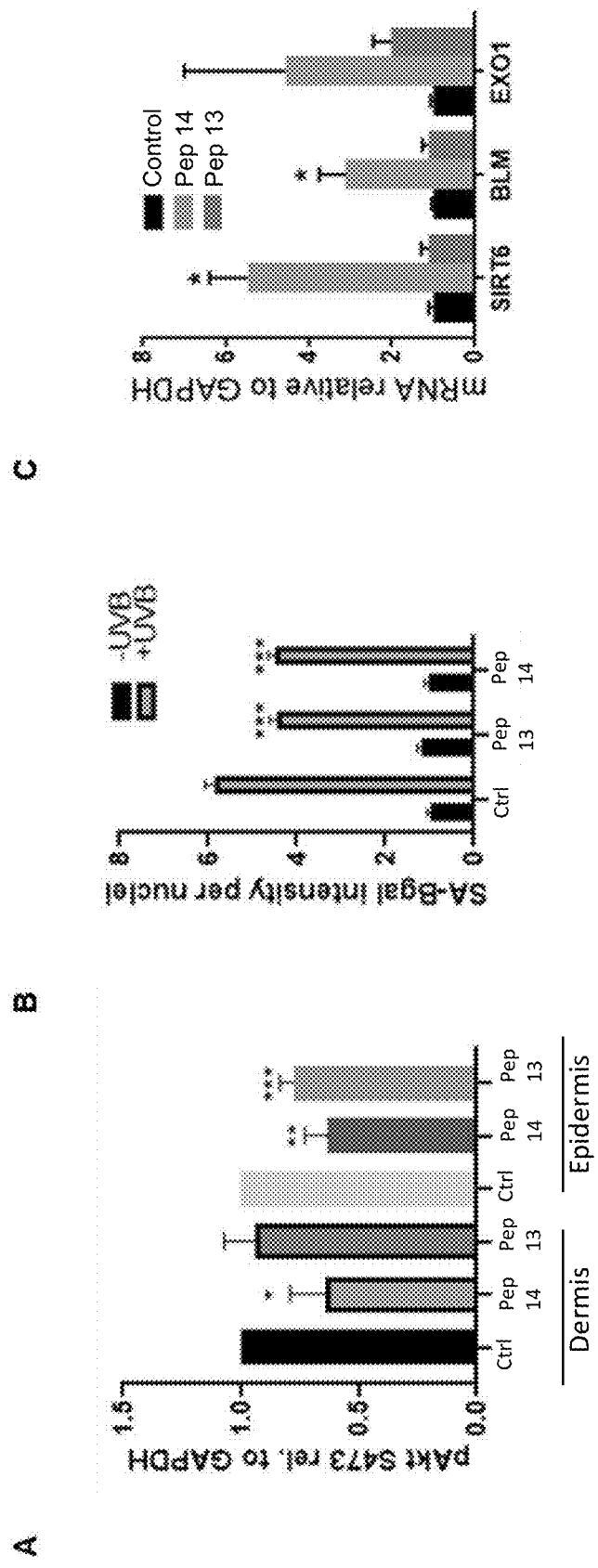
FIG. 8 illustrates pAkt S473 can be significantly decreased in both epidermal and dermal samples treated with a polypeptide (panel A), polypeptide treatment can decrease SA-B gal staining in UVB exposed samples indicating protection from UVB-induced cellular senescence (panel B), and that a polypeptide can increase the expression of SIRT6 and BLM (panel C). *$p<0.05$; $p<0.01$; *$p<0.001$.

In order to shed light into the mechanism of action of Peptide 14 and similar Peptide 13, Akt S473 phosphorylation (FIG. 8, panel A), senescence associated β-galactosidase staining (FIG. 8, panel B), as well as mRNA expression (FIG. 8, panel C) were investigated. For Akt S473 phosphorylation analysis using western blotting, human primary fibroblasts and keratinocytes were used. These cells were used to build human skin equivalents, which were kept in a 5% $CO_2$, 37° C. and 95% humidity atmosphere air liquid interface. Then, skin equivalents were treated with 1 µM of either Peptide 14 or Peptide 13 for 5 days, and protein analysis was performed on the skin equivalents. Protein was isolated and quantified. Equal amounts of protein were loaded in polyacrylamide gels and transferred into a nitrocellulose membrane. GAPDH (loading control) and pAkt S473 antibodies were incubated with the membrane and staining was revealed by chemiluminescence. Relative pAkt S473/GAPDH signal was compared between treated and non-treated samples. For senescence associated B-galactosidase staining experiments, fibroblasts were used. These cells were cultured in DMEM (Dulbecco's Modified Eagle's Medium) culture supplemented with 10% v.v. fetal bovine serum (FBS), and 1% v.v. of penicillin/streptomycin solution (1,000 U·mL−1). Cells were kept in a 5% $CO_2$, 37° C. and 95% humidity atmosphere. After expansion, these cells were seeded in 96-well plates (4,000 cells per well) and incubated with basal medium for 6 hours to allow cell attachment. After, cells were exposed twice to 0.05 J/$cm^2$. This was followed immediately by a second incubation, wherein Peptide 14 or Peptide 13 were added to the medium and left for 48 hours, when medium was changed, and cells were stained for senescence associated B-galactosidase. Untreated cells were incubated with vehicle only as negative controls (−). Relative staining was obtained after normalizing untreated control senescence associated B-galactosidase levels to 100%. For mRNA analysis, fibroblasts were used. These cells were cultured in DMEM (Dulbecco's Modified Eagle's Medium) supplemented with 10% v.v. fetal bovine serum (FBS), and 1% v.v. of penicillin/streptomycin solution (1,000 U·mL−1). Cells were kept in a 5% $CO_2$, 37° C. and 95% humidity atmosphere. After expansion, these cells were seeded in either 6-well plates (50,000 cells per well) and incubated with basal medium for 6 hours to allow cell attachment. After, cells were incubated for 48 hours with either Peptide 14 or Peptide 13. A negative control comprised untreated cells, which received vehicle only. Total RNA was isolated, samples were reverse transcribed, and mRNA expression of GAPDH, sirtuin 6 (SIRT6), BLM, and exonuclease 1 (EXO1) genes were determined using qPCR. Negative controls received vehicle only. CT values were analyzed using the $2^{-\Delta\Delta Ct}$ method. Average mRNA expression was normalized to GAPDH ($\Delta$Ct) and to the negative control group ($\Delta\Delta$Ct). For all analysis, three independent experiments were performed with three technical replicates. Data was analyzed using a T-test. Statistical significance was determined as p values equal or lower than 0.05 (FIG. 8).

pAkt S473 was significantly decreased in both epidermal, as well as dermal samples treated with Peptide 14 (*p<0.05, and p<0.01, respectively). Peptide 13 decreased pAkt S473 in dermal samples only (*p<0.001) (FIG. 8, panel A). For UVB and senescence associated B-galactosidase staining, it was observed that staining always increased following UVB exposure. Additionally, both Peptide 14 and Peptide 13 decreased staining in UVB-exposed samples (***p<0.001). Peptide 14 specifically led to increased SIRT6 and BLM expression in treated samples (*p<0.05) (FIG. 8).

Example 9

Human primary fibroblasts and keratinocytes isolated from healthy elder donors were used to build human skin equivalents. Those skin equivalents were treated with 0.01% w.v. of Peptide 14 for 5 days and characterized according to epidermal thickness, which was quantified according to total epidermal area. Negative controls were treated with formulation only. Example histological images are shown in panel A of FIG. 9. Three independent experiments were performed with three technical replicates. Data was analyzed using a t-test. Statistical significance was determined as p-values equal or lower than 0.05 (panel B of FIG. 9).

Figure 9:
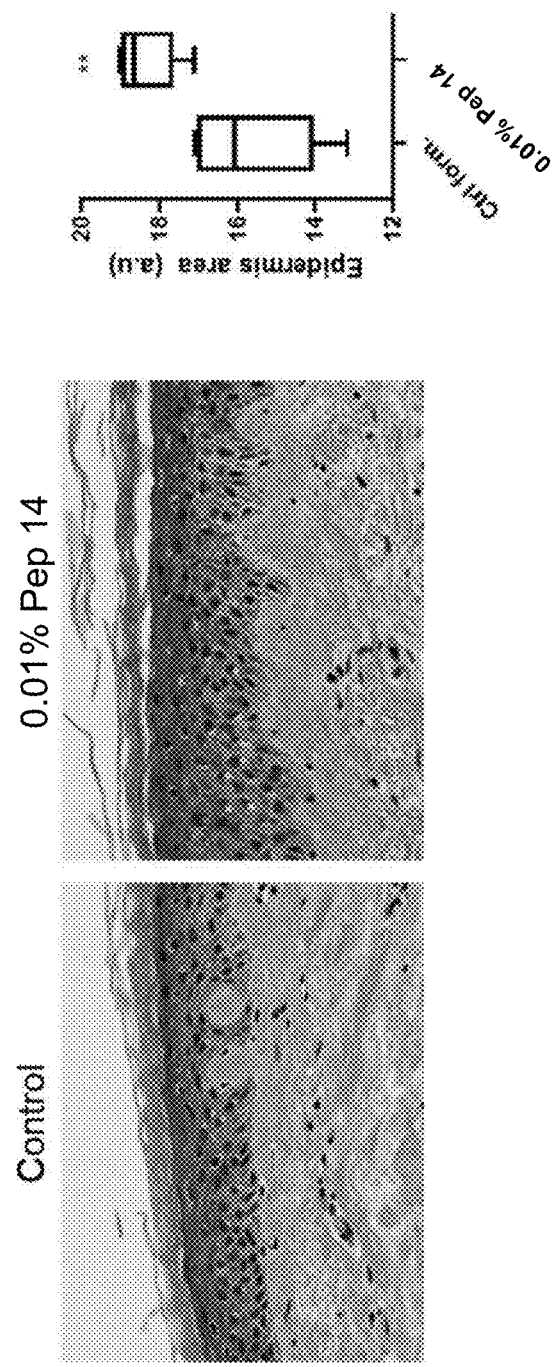
FIG. 9 illustrates increased epidermal layer thickness in human skin equivalents as histological images (panel A) and statistical analysis of acquired data (panel B). **$p<0.01$.

Peptide 14 treatment of human skin equivalents promoted increased epidermal thickness (p<0.01), compared to untreated control, suggesting beneficial effects of the polypeptide over skin epidermis (FIG. 9**).

Example 10

Figure 10:
FIG. 10 illustrates the predicted three dimensional structures of two polypeptides, Peptide 14 (panel A) and Peptide 13 (panel B), as well as the superposition of the two polypeptides (panel C).
Figure 10:
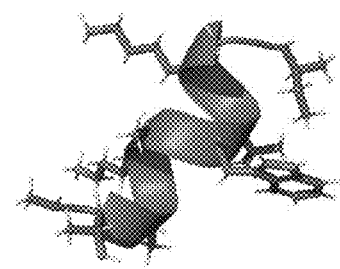
Figure 10:
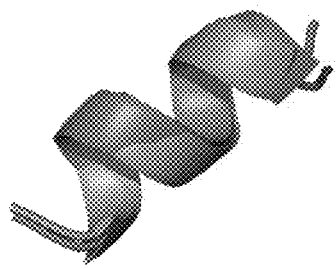

Predicted three-dimensional structures of polypeptides having the amino acid sequence ETAKHWLKGI (SEQ ID NO:1) and ATAKAWLKGI (SEQ ID NO:2) were determined in water. The structure predictions are shown in FIG. 10, panel A (SEQ ID NO:1) and FIG. 10, panel B (SEQ ID NO:2). The structures were superimposed (FIG. 10, panel C) to illustrate the resemblance of the structures.

Example 11

A topically-applied formulation of Peptide 14 is made including niacin, vitamin E, at least one preservative, at least one emulsifier and between 50-150 µM Peptide 14. The topical formulation was applied to human skin, resulting in the reduction of the appearance of wrinkles.

Example 12

A topically-applied formulation of Peptide 14 is made including niacin, vitamin E, at least one preservative, at least one emulsifier and between 75-100 µM Peptide 14. The topical formulation was applied to human skin, resulting in the reduction of the appearance of wrinkles.

Example 13

An exemplary topically-applied formulation is shown below in Table 4. The topical formulation was applied to human skin, resulting in the reduction of at least one of appearance of wrinkles, appearance of skin tone (evenness), appearance of pores, appearance of texture and smoothness, firmness, elasticity, and overall appearance. The polypeptides in the formulation comprises at least one of the polypeptides disclosed herein.

TABLE 4

Exemplary Formulation

| Components | Percentage in formulation |
|---|---|
| Water | 40%-65% |
| Skin hydrators | 5%-45% |
| Emollients | 6%-20% |
| Vitamins | 0.5%-5% |
| Emulsifiers/stabilizers | 0.5%-9% |
| Polypeptides | 0.001%-4% |

Example 14

An exemplary topically-applied formulation comprising Peptide 14 is shown below in Table 5. The topical formulation was applied to human skin, resulting in the reduction of at least one of appearance of wrinkles, appearance of skin tone (evenness), appearance of pores, appearance of texture and smoothness, firmness, elasticity, and overall appearance. The polypeptides in the formulation comprises Peptide 14.

TABLE 5

Exemplary Formulation

| Components | Percentage in formulation |
|---|---|
| Water | 40%-65% |
| Skin hydrators | 5%-45% |
| Emollients | 6%-20% |

TABLE 5-continued

Exemplary Formulation

| Components | Percentage in formulation |
|---|---|
| Vitamins | 0.5%-5% |
| Emulsifiers/stabilizers | 0.5%-9% |
| Polypeptides | 0.001%-4% |

Example 15

Three-dimensional in vitro skin models and ex vivo human skin samples were assessed for skin aging after treatment with Peptide 14.

In vitro 3D skin model: 3D skin models were prepared using a modified method based on the preparation described in Pennacchi, P. C. et al. Glycated Reconstructed Human Skin as a Platform to Study the Pathogenesis of Skin Aging. Tissue Eng. Part A 21, 2417-2425, 2015. Briefly, type I collagen gels embedded with fibroblasts were seeded with normal human epidermal keratinocytes (NHEKs) on top of the gel and cultured for 24 hours in order for NHEKs to reach a monolayer. Then, the gels with NHEKs on the top were raised to an air-liquid interface and cultured for additional 10 days to allow for epidermal cornification. The gels were treated with 12.5 µM of Peptide 14 by addition of Peptide 14 to the culture medium.

Ex-vivo human skin model: Skin samples from healthy human donors were obtained from ZenBio (Research Triangle, NC) and maintained in an air-liquid interface culture with Dulbecco's Modified Eagle Medium (DMEM) (Invitrogen, Carlsbad, CA), supplemented with 10% (v/v) FBS. The skin samples were treated either with a control vehicle or 12.5 µM Peptide 14 in the media, on day one and day three. After five days, the samples were harvested and fixed in formalin for histology or used for DNA isolation.

DNA methylation analysis: The predicted biological age, also referred to as molecular DNA age, was determined from the level of DNA methylation in 3D skin model samples and ex vivo human skin biopsy samples. Total DNA samples were obtained from the samples using the QIAamp DNA Mini Kit (Qiagen) following manufacturer instructions. DNA methylation assessment, as a marker of skin aging, was performed using the human Illumina Infinium EPIC 850K chip. DNA samples included: i) four skin biopsy samples (from same donor) which were considered as untreated controls, ii) four skin biopsy samples (same donor) treated with 12 µM Peptide 14, iii) three 3D skins samples (each sample a pool of 3 skins from 1 donor, total 3 donors) which were considered as untreated controls, iv) three 3D skins samples (each sample a pool of 3 skins from 1 donor, total 3 donors) treated with 12 µM Peptide 14. The raw image data was processed using the commands preprocessRaw( ) followed by preprocessSWAN( ). Methylation signals (M-values) were then converted to ratios using the ratioConvert( ) and next to beta values using getBeta( ), all functions implemented in the "minfi" R package. Beta values were normalized using the betaqn( ) method, which quantile normalizes betas, implemented by the "watermelon" package. and normalized using the "preprocessQuantile" normalization method implemented in the "minfi" R package. Normalized beta values were used for age estimation.

Statistical analysis: Data was tested for normal distribution by Shapiro-Wilk test. In cases where more than 2 groups were compared, one-way ANOVA was performed, followed by Bonferroni's multiple comparisons test. For cases where paired samples were compared, a paired t-test was performed. p≤0.05 was considered statistically significant. Statistical analyses were performed using GraphPad Prism (GraphPad software) or R software.

Results: The in vitro 3D skin models and ex vivo human skin samples showed a decrease in skin aging after 5 days of treatment with Peptide 14 as shown in FIGS. 11A, 11B and 11C. FIG. 11A shows hematoxylin and eosin (H&E) stained histological images of the 3D skin equivalents (top row) and ex vivo skin biopsy samples (bottom row) cultured with no Peptide 14 (Control) and 12.5 µM Peptide 14 for 5 days. The 3D skin equivalents and ex vivo skin samples treated with Peptide 14 generally showed epidermal thicknesses that are similar to or thicker than the untreated control samples. FIG. 11B shows the predicted age, also referred to as molecular DNA age, of the 3D skin model samples treated with 12.5 µM Peptide 14 (treatment) was lower than the predicted age for samples that were untreated control (ctrl). The mean of predicted age for the untreated 3D skin model was about 80 whereas the mean of the predicted age for the Peptide 14-treated 3D skin model was about 66 (p=0.25 by t-test). FIG. 11C shows the predicted age of ex vivo skin biopsy treated with 12.5 µM Peptide 14 was lower than the predicted age of samples that were untreated control (ctrl). The mean of predicted age for the ex vivo skin biopsy samples was about 71 whereas the mean of the predicted age for the Peptide 14-treated ex vivo skin biopsy samples was about 68 (**p<0.01).

Example 16

In vertebrates, specialized cells called melanocytes usually produce melanin. MeWo cells are a human immortalized melanocyte cell line that represent late differentiated melanocytes expressing retinoic acid receptors and may provide an experimental model for in vitro investigation of melanogenesis. Additional description regarding the use of MeWo cells as an in vitro model melanogenesis is found in Schadendorf et al., 1994. Retinoic Acid Receptor-gamma-selective Retinoids Exert Antiproliferative Effects on Human-melanoma Cell-growth In-vitro. International Journal of Oncology. Doi:10.3892/Ijo.5.6.1325 and Malaspina et al., Depigmenting potential of lichen extracts evaluated by in vitro and in vivo tests. PeerJ 8:e9150 https://doi.org/10.7717/peerj.9150.

To test whether Peptide 14 promotes depigmentation of melanocytes, MeWo cells were cultured in DMEM supplemented with 10% v/v FBS and 1% v/v of penicillin/streptomycin solution (1,000 U·mL$^{-1}$) at 5% $CO_2$, 37° C. and 95% humidity. For two weeks prior to treatment with one of the experimental conditions (pre-treatment), the MeWo cells were cultured with isobutyl methylxanthine (IBMX) to stimulate melanin synthesis. After the MeWo cells were seeded in 6-well plates at 1,000,000 cells per well for 6 hours, the cells were incubated with one of the experimental conditions for 7 days and analyzed for intracellular and supernatant melanin content.

The experimental conditions included a positive control group, a negative control group, a Peptide 14 (IBMX) 7d group, and a retinoic acid (IBMX) 7d group. The negative control group comprised MeWo cells which were stimulated with 25 µM IBMX for 2 weeks in the pre-treatment period and then were untreated for 7 days, receiving the vehicle only, after being plated for the experiment. The positive control group comprised MeWo cells that were incubated with 25 µM IBMX during the entire experiment, for 2 weeks in the pre-treatment period and for 7 days in the treatment period. The Peptide 14 (IBMX) 7d group comprised MeWo cells that were incubated with 25 µM IBMX 2 weeks in the pre-treatment period and then treated for 7 days with 25 µM IBMX and 3.12 µM Peptide 14. The retinoic acid (IBMX) 7d group comprised MeWo cells that were incubated with 25 µM IBMX 2 weeks in the pre-treatment period and then treated for 7 days with 25 µM IBMX and 2 µM retinoic acid.

After treatment, the melanin content in the cell pellet and the cell culture supernatant was assessed by the absorbance of the samples at 492 nm. The cell pellet was prepared by trypsinization, counting and incubated for 16 hours in 200 µL of 1M NaOH (Matsuda et al., 2004; Yoo et al., 2007). The cell culture supernatant was obtained after 1.2×g centrifugation for 10 minutes. Data are presented as relative melanin content, absorbance of the samples at a specified wavelength (492 nm) normalized to the absorbance of the negative control samples also as the same wavelength. Three independent experiments including three technical replicates were performed. The data were analyzed using ANOVA and Bonferroni post-hoc test when a statistical significance was detected. The statistically significant p-values are noted by * for p<0.05;  for p<0.01; * for p<0.001; **** for p<0.0001 between the groups.

Figure 12A:
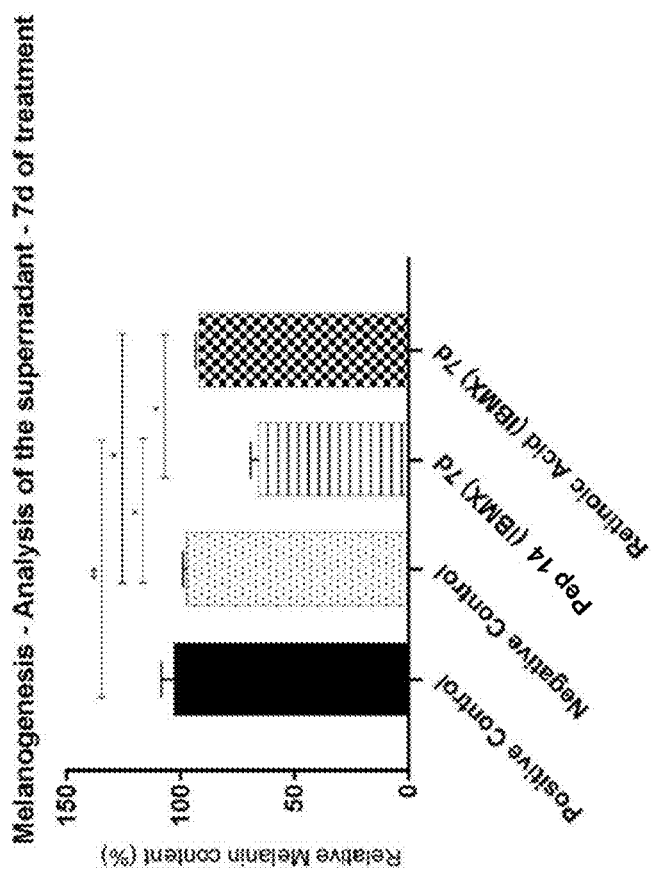
FIG. 12A illustrates the relative melanin content of cellular pellet of MeWo cells treated with the positive control of isobutyl methylxanthine (IBMX), negative control, Peptide 14 with IBMX, and retinoic acid with IBMX for 7 days after 14 day pre-treatment culture with IBMX. Data are presented as average and standard deviation of melanin content normalized to negative control (100%). $p<0.01$; *$p<0.001$; ****$p<0.0001$.
Figure 12B:
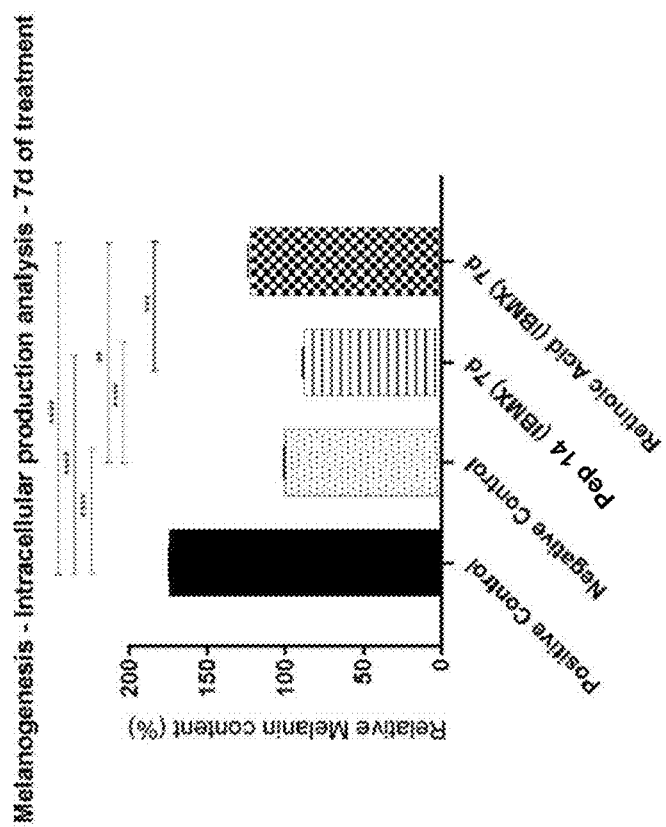
FIG. 12B illustrates the relative melanin content of cell culture medium supernatant from MeWo cells treated with the positive control with IBMX, negative control, Peptide 14, and retinoic acid for 7 days after 14 day pre-treatment culture with isobutyl methylxanthine (IBMX). Data are presented as average and standard deviation of melanin content normalized to negative control (100%). *$p<0.05$; **$p<0.01$.

The Peptide 14 treatment promoted a significant decrease in the relative melanin content as compared to the positive control, negative control and retinoic acid treatment groups in the cellular pellet, as shown in FIG. 12A, and in the cell culture supernatant, as shown in FIG. 12B. In the cell pellets as shown in FIG. 12A, the positive control had a relative melanin content of about 170% times of the negative control group (** p<0.0001) and the retinoic acid treatment group had a relative melanin content of about 125% of the negative control group (p<0.01) while Peptide 14 treatment had a relative melanin content of about 90% of the negative control group (***p<0.001) or lower than the negative control group. In the cell culture supernatant as shown in FIG. 12B, the positive control and the retinoic acid treatment group had relative melanin contents that were very similar to the negative control group while Peptide 14 treatment had a relative melanin content of about 70% of the negative control group (*p<0.05) or lower than the negative control group.

This shows that Peptide 14 may have applications to reduce various melanogenesis-related conditions, including but not limited to melasma, skin hyperpigmentation caused by cutaneous inflammation, hormonal changes, aging, sun exposure, and chronic lesions. In addition, Peptide 14 appeared to perform better than retinoic acid, currently considered the gold standard molecule for anti-aging skincare.

Example 17

The skin frequently may experience rebound hyperpigmentation, where pigmentation is reestablished in the skin after the discontinuation of the lightening treatment(s). To test whether the depigmentation effect of Peptide 14 remained after the Peptide 14 treatment was discontinued, MeWo cells were cultured in DMEM supplemented with 10% v/v FBS and 1% v/v of penicillin/streptomycin solution (1,000 U·mL$^{-1}$) at 5% $CO_2$, 37° C. and 95% humidity. For two weeks prior to treatment with one of the experimental conditions (pre-treatment), the MeWo cells were cultured with isobutyl methylxanthine (IBMX) to stimulate melanin synthesis. After the MeWo cells were seeded in 6-well plates at 1,000,000 cells per well for 6 hours, the cells were incubated with one of the experimental conditions for 14 days and analyzed for intracellular and supernatant melanin content.

The experimental conditions included a positive control group, a negative control group, a Peptide 14 (IBMX) 14 days group, a retinoic acid (IBMX) 14 days group, a Peptide 14 (IBMX) interrupted on $7^{th}$ day group, and a retinoic acid (IBMX) interrupted on $7^{th}$ day group. The negative control group comprised MeWo cells which were stimulated with 25 µM IBMX for 2 weeks in the pre-treatment period and then were untreated for 14 days, receiving the vehicle only, after being plated for the experiment. The positive control group comprised MeWo cells that were incubated with 25 µM IBMX during the entire experiment, for 2 weeks in the pre-treatment period and for 14 days in the treatment period. Some of the groups were treated with both IBMX 25 µM for 7 or 14 days, as well as 3.12 µM Peptide 14, or both IBMX 25 µM (for 7 or 14 days), as well as retinoic acid 2 µM. The Peptide 14 (IBMX) 14 day group comprised MeWo cells that were incubated with 25 µM IBMX 2 weeks in the pre-treatment period and then treated for 14 days with 25 µM IBMX and 3.12 µM Peptide 14. The retinoic acid (IBMX) 14 day group comprised MeWo cells that were incubated with 25 µM IBMX 2 weeks in the pre-treatment period and then treated for 14 days with 25 µM IBMX and 2 µM retinoic acid. The Peptide 14 (IBMX) 7 day group comprised MeWo cells that were incubated with 25 µM IBMX 2 weeks in the pre-treatment period, then treated for only 7 days with 25 µM IBMX and 3.12 µM Peptide 14, and cultured for additional 7 days with 25 µM IBMX only. The retinoic acid (IBMX) 7 day group comprised MeWo cells that were incubated with 25 µM IBMX 2 weeks in the pre-treatment period, then treated for only 7 days with 25 µM IBMX and 2 µM retinoic acid and cultured for additional 7 days with 25 µM IBMX only.

After treatment, the melanin content in the cell pellet and the cell culture supernatant was assessed by the absorbance of the samples at 492 nm. The cell pellet was prepared by trypsinization, counting and incubated for 16 hours in 200 µL of 1M NaOH (Matsuda et al., 2004; Yoo et al., 2007). The cell culture supernatant was obtained after 1.2×g centrifugation for 10 minutes. Data are presented as relative melanin content, absorbance of the samples at a specified wavelength (492 nm) normalized to the normalized to the number of cells in the sample absorbance of the negative control samples also as the same wavelength. Since cell proliferation is significant during the 14 day period, in this experiment only, the melanin content data was normalized to the number of cells in the sample within each group. Three independent experiments including three technical replicates were performed. The data were analyzed using ANOVA and Bonferroni post-hoc test when a statistical significance was detected. The statistically significant p-values are noted by * for $p<0.05$;  for $p<0.01$; * for $p<0.001$; **** for $p<0.0001$ between the groups.

In addition, the mRNA level of key genes involved in melanogenesis, including tyrosinase, melanocyte inducing transcription factor (MITF) and dopachrome tautomerase (DCT) was analyzed.

Figure 13A:
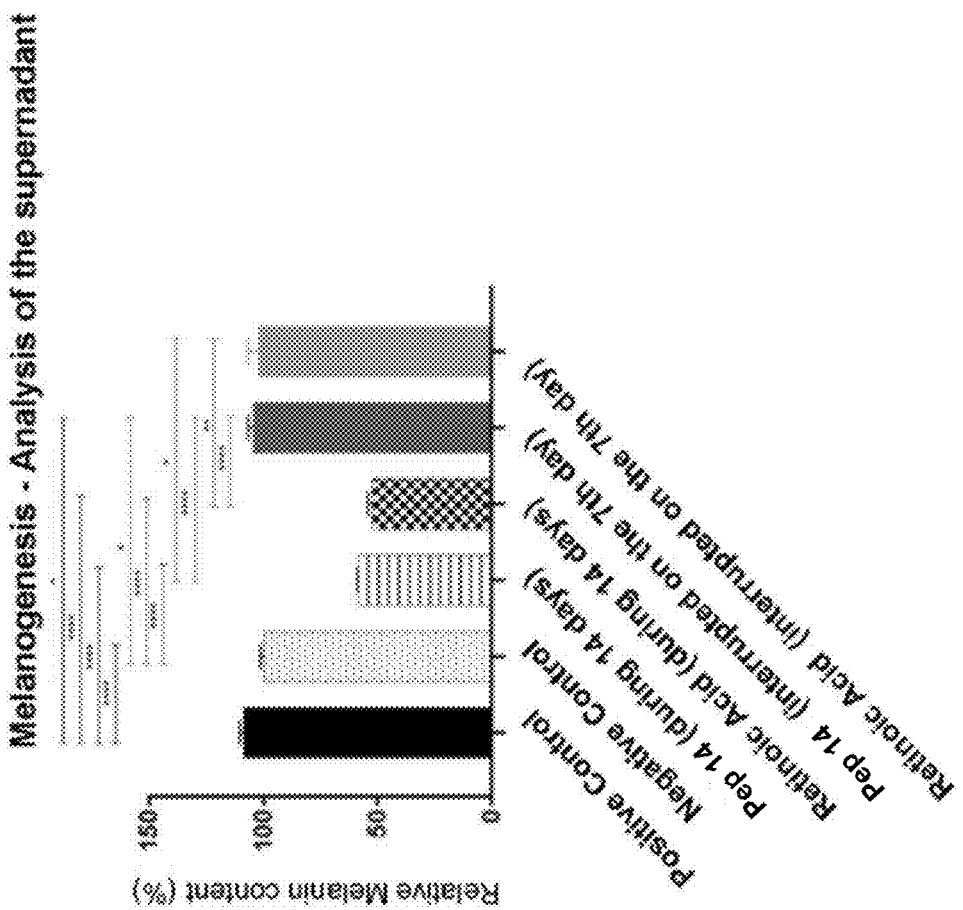
FIG. 13A illustrates the relative melanin content of cellular pellet of MeWo cells treated with the positive control of IBMX, negative control, Peptide 14 with IBXM for 14 days, retinoic acid with IBMX for 14 days, Peptide 14 with IBXM for 7 days, retinoic acid with IBMX for 7 days, after 14 day pre-treatment culture with isobutyl methylxanthine (IBMX). Data are presented as average and standard deviation of melanin content normalized to negative control (100%). *$p<0.05$; $p<0.01$; **$p<0.0001$.
Figure 13B:
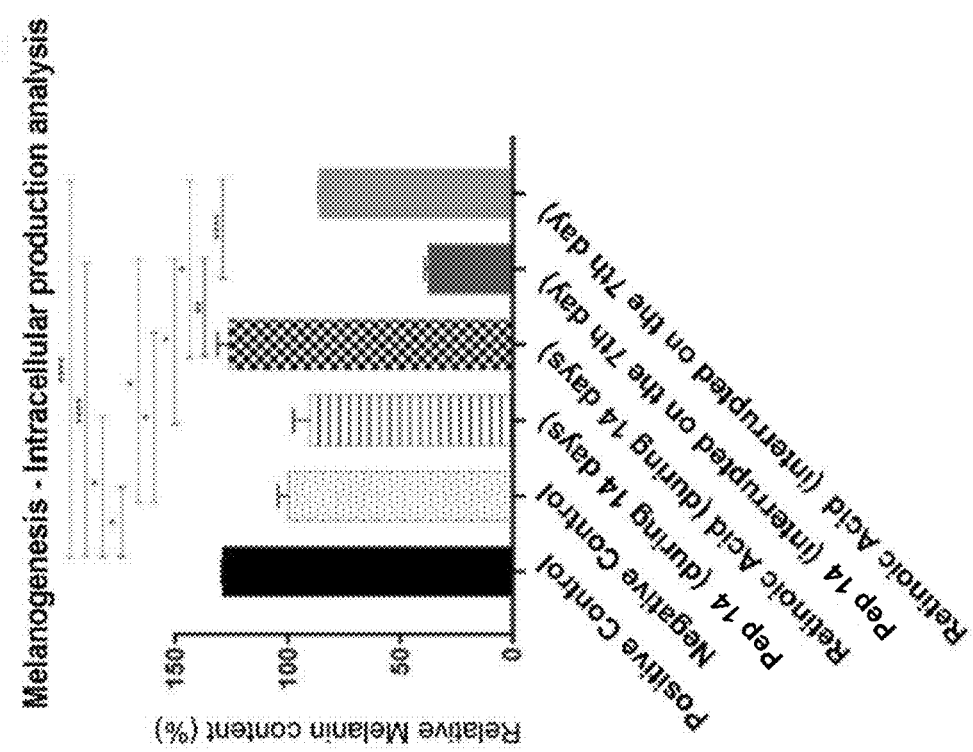
FIG. 13B illustrates the relative melanin content of cell culture medium supernatant from MeWo cells treated with the positive control of IBMX, negative control, Peptide 14 with IBXM for 14 days, retinoic acid with IBMX for 14 days, Peptide 14 with IBXM for 7 days, retinoic acid with IBMX for 7 days, after 14 day pre-treatment culture with isobutyl methylxanthine (IBMX). Data are presented as average and standard deviation of melanin content normalized to negative control (100%). *$p<0.05$; $p<0.01$; **$p<0.0001$.

The Peptide 14 treatment promoted a significant decrease in the relative melanin content as compared to the positive control and retinoic acid treatment groups in the cellular pellet, as shown in FIG. 13A, and in the cell culture supernatant, as shown in FIG. 13B. In the cell pellets as shown in FIG. 13A, the positive control had a relative melanin content of about 130%, and the retinoic acid 14 day treatment group had a relative melanin content of about 130% while Peptide 14 14 day treatment group had a relative melanin content of about 90%, or lower than the negative control group. The Peptide 14 7 day treatment group had a relative melanin content of about 40%, the lowest relative melanin content of the experimental groups. The retinoic acid 7 day treatment group had a relative melanin content of about 90%. In the cell culture supernatant as shown in FIG. 13B, the positive control had a relative melanin content of about 110%, while the retinoic acid 14 day treatment group and the Peptide 14 14 day treatment group had relative melanin contents of about 50%. The retinoic acid 7 day treatment group and the Peptide 14 7 day treatment group had relative melanin contents of about 100%.

Figure 14A:
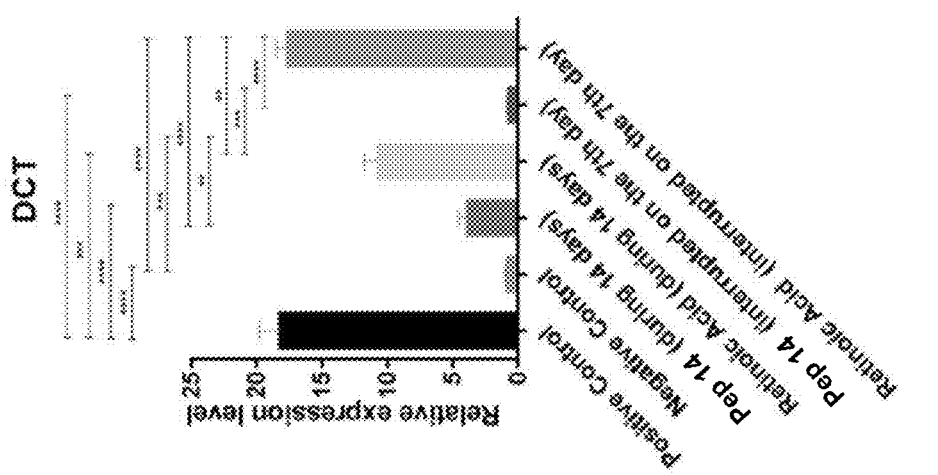
FIG. 14A illustrates the relative mRNA expression level of tyrosinase of MeWo cells treated with the positive control of IBMX, negative control, Peptide 14 with IBXM for 14 days, retinoic acid with IBMX for 14 days, Peptide 14 with IBXM for 7 days, retinoic acid with IBMX for 7 days. Data are presented as average and standard deviation of 2-ddCt normalized to GAPDH and negative control expression (100%). *$p<0.05$; $p<0.01$; **$p<0.0001$.
Figure 14B:
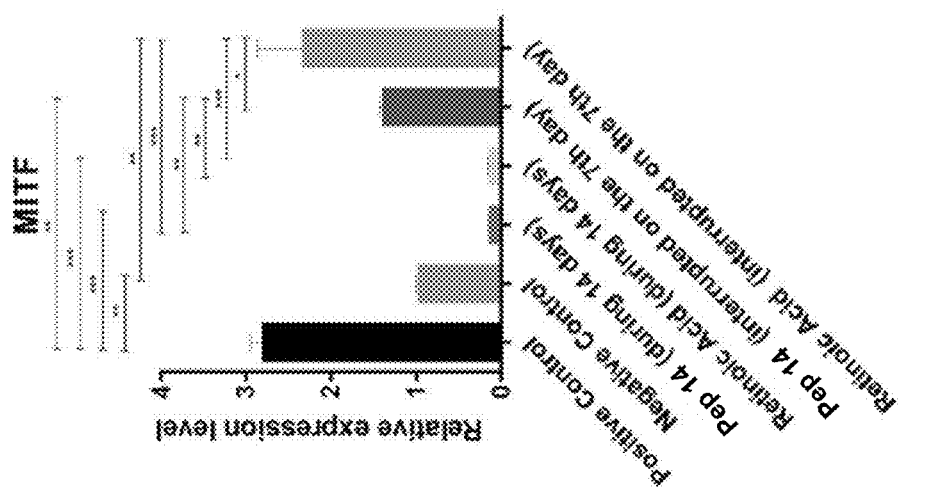
FIG. 14B illustrates the relative mRNA expression level of melanocyte inducing transcription factor (MITF) of MeWo cells treated with the positive control of IBMX, negative control, Peptide 14 with IBXM for 14 days, retinoic acid with IBMX for 14 days, Peptide 14 with IBXM for 7 days, retinoic acid with IBMX for 7 days. Data are presented as average and standard deviation of 2-ddCt normalized to GAPDH and negative control expression (100%). *$p<0.05$; $p<0.01$; *$p<0.001$.
Figure 14C:
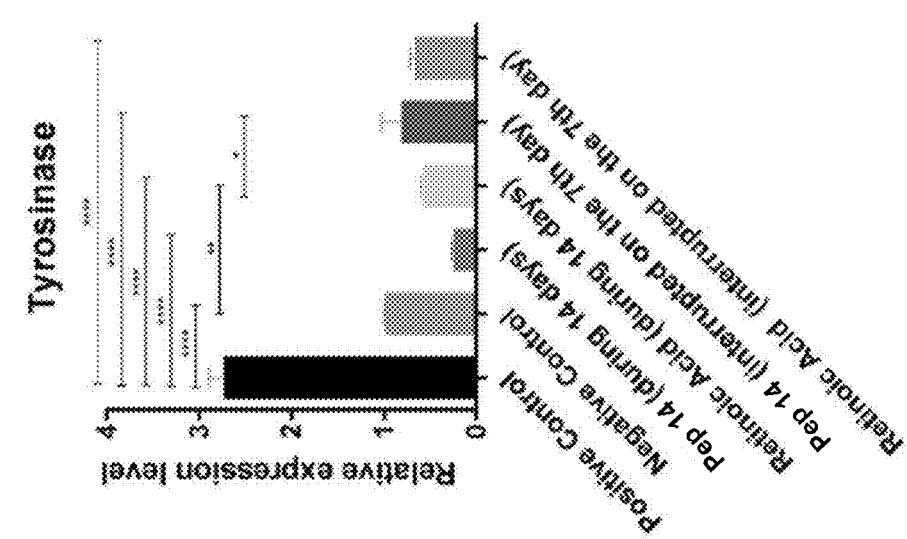
FIG. 14C illustrates the relative mRNA expression level of dopachrome tautomerase (DCT) of MeWo cells treated with the positive control of IBMX, negative control, Peptide 14 with IBXM for 14 days, retinoic acid with IBMX for 14 days, Peptide 14 with IBXM for 7 days, retinoic acid with IBMX for 7 days. Data are presented as average and standard deviation of 2-ddCt normalized to GAPDH and negative control expression (100%). p<0.01; *p<0.001; ****p<0.0001.

The mRNA levels of melanogenesis-related genes are shown in FIGS. 14A, 14B, and 14C. Peptide 14 treatment appears to result in significant decreases in the expression of tyrosinase, MITF, and DCT genes, that are lower than or at least similar to the mRNA levels for retinoic acid treated groups. As shown in FIG. 14A, the relative expression level of tyrosinase was lowest for Peptide 14 14 day treatment group as compared to the other experimental groups. As shown in FIG. 14B, the relative expression level of MITF was the lowest for Peptide 14 14 day treatment group and the retinoic acid 14 day treatment group. As shown in FIG. 14C, the relative expression level of DCT was lowest for Peptide 14 14 day treatment group and Peptide 14 7 day treatment group as compared to the other experimental groups.

This shows that Peptide 14 may reduce melanogenesis and continue to result in lower melanogenesis after discontinuing Peptide 14 treatment. In addition, Peptide 14 appeared to perform better than retinoic acid, currently considered the gold standard molecule for anti-aging skincare.

Example 18

To test the effect of Peptide 13 and Peptide 14 treatment on human skin models and the skin morphology, human primary fibroblasts and keratinocytes isolated from healthy elder donors (71, 84, and 90 years old) were used to build human skin equivalents. The skin equivalents were treated with 0.01% w/v (or 1 µM) of Peptide 13 or Peptide 14 for 5 days. The negative controls were treated with formulation only. After the 5-day culture, the skin equivalents were analyzed for epidermal thickness, which was quantified according to total epidermal area. Quality assessment based several parameters was performed by blind analysts. The observed parameters include general organization of cell layers, as well as the thickness of the horny layer, among other aspects and were shown to decrease with aging and senescence level. The assessment had a maximum score of 28, where higher score correlated with decrease in age and senescence. A minimal score of 19 was required for batch use. This score was validated internally and shown to decrease with age/senescence of the skin equivalents or cultured cells. Three independent experiments were performed with three technical replicates. Data were analyzed using a t-test. Statistical significance was determined as p-values equal or lower than 0.05. The statistically significant p-values are noted by * for $p<0.05$;  for $p<0.01$; * for $p<0.001$; **** for $p<0.0001$ between the groups.

Figure 15B:
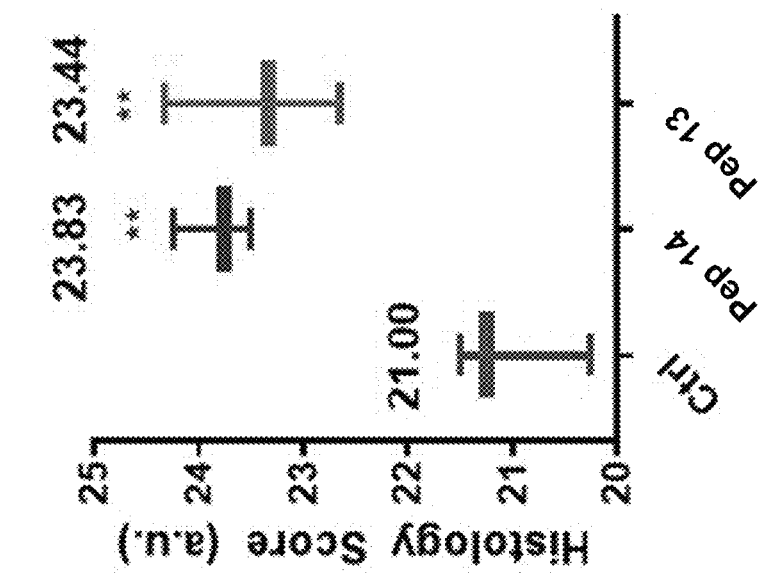
FIG. 15B illustrates the mean of histology scores of human skin models treated with a vehicle only (control), Peptide 14, or Peptide 13, which were 21.00, 23.83, and 23.44, respectively. **p<0.01.
Figure 15A:
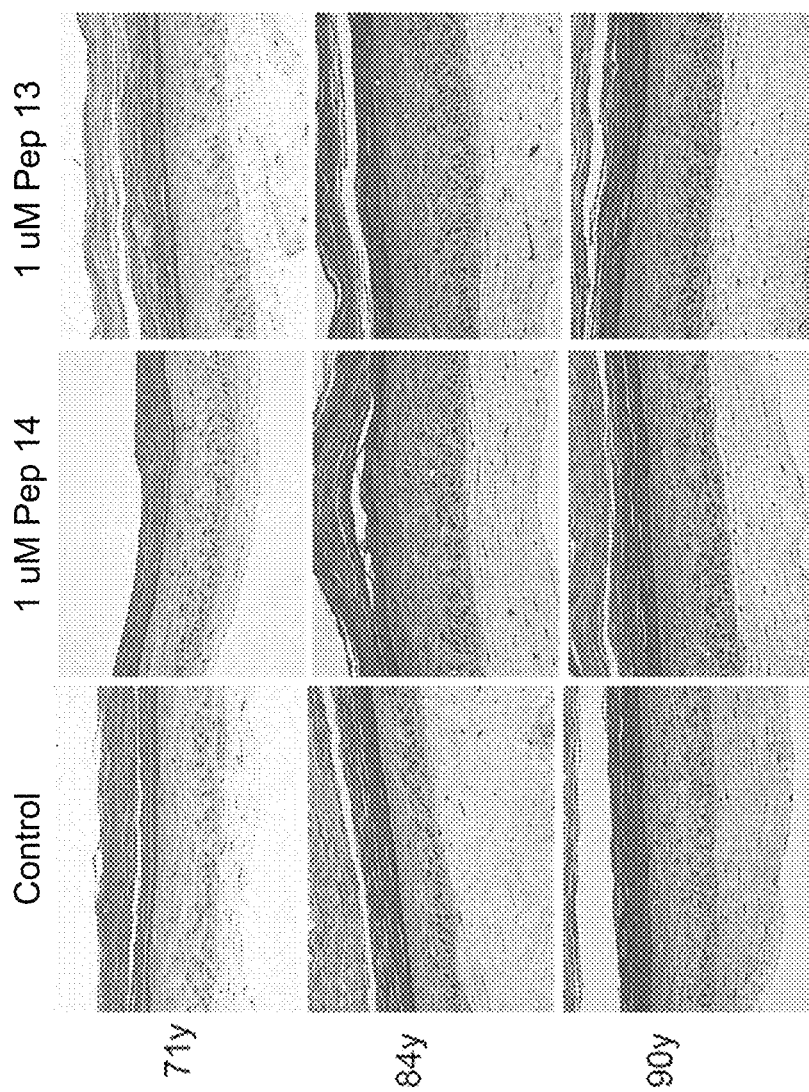
FIG. 15A illustrates the H&E-stained histological images of the in vitro human skin models treated with a vehicle only (control), Peptide 13, or Peptide 14.

FIG. 15A shows the H&E-stained histological images of the in vitro human skin models treated with a vehicle only (control), Peptide 13, or Peptide 14. The human skin models treated with Peptide 13 or Peptide 14 generally showed similar or increased thickness of stratum corneum layer (as indicated by dark gray layer on top of the images or stained bright pink by H&E) and epidermal layer (as shown by medium gray layer in the middle of the images or stained purple by H&E) to the untreated control samples. FIG. 15B shows the mean of histology scores of human skin models treated with a vehicle only (control), Peptide 14, or Peptide 13, which were 21.00, 23.83, and 23.44, respectively. The histology scores were higher for samples treated with Peptide 13 or Peptide 14 than for the negative control. Treatment of skin samples with Peptide 13 or Peptide 14 appeared to improve skin morphology as assessed by epidermal thickness and barrier.

Example 19

To study the level of penetration by Peptide 14 through the depth of the skin, a diffusion study was performed using Franz cells and on ex vivo skin culture sample. Fresh human skin from the abdomen of a female donor (79 years old) was cut in small pieces ~2.5 cm×2.5 cm.

In the Franz cell study, the skin was treated with 10 µL of a formulated cream comprising 0.01% Peptide 14 and placed in a Franz cell with a contact area of 5 mm diameter (0.2 cm$^2$). The receptor chamber had 2 mL of PBS, pH 7.4. The Franz cells were kept for 24 hours at 32° C. under agitation.

In the ex vivo skin culture study, the skin was treated with 2 µL of a formulated cream comprising 0.01% of Peptide 14 (for a total of 200 ng of Peptide 14). The skin sample was then placed in an air-liquid interface with DMEM media in the bottom and were kept for 24 hours at 37° C.

After 24 hours, the excess formulation on the skin was removed with a tissue paper, and the skin samples were washed 4 times in PBS. All the surrounding skin was also removed. The skin was then incubated at 60° C. for 1-2 minutes to separate epidermis from dermis. The PBS in the receptor chamber (2 mL), the epidermis layer, and the dermis layer were collected and frozen at −80° C. until further analysis. The dermis layer was analyzed mass spectrometry for the Peptide 14 to determine amount of Peptide 14 that penetrated into the dermis.

In the Franz cell study, about 1.37% to 2.60% of the applied Peptide 14 was found in the dermis layer. In the ex vivo skin culture study, about 1.94% to 1.96% of the applied Peptide 14 was found in the dermis layer. Very little to no Peptide 14 penetrated into the dermis when Peptide 14 was applied topically to the surface of the skin. This demonstrates that Peptide 14 achieves very low to minimal dermal penetration with topical application.

Example 20

A clinical study was performed on human subjects to assess the effect of topical application of Peptide 14 on the face. This study was approved by an IRB board. 22 human subjects participated in the clinical study and were asked to use two products, one in each side of the face. On the right side of the face, the subjects used the negative control comprising the formulation only. On the left side of the face, the subjects used the treatment formulation comprising 0.01% Peptide 14. The subjects underwent assessments before starting to use the product (baseline) and after 6 weeks and 12 weeks of daily topical application of the formulations to the respective sides of the face. Various measures of skin moisture content, trans-epidermal water loss (TEWL), dermal thickness and echogenicity, intracutaneous analysis, skin viscoelastic properties, and skin surface profile were taken as detailed below to assess the effect of topical Peptide 14 application on facial skin on the appearance of lines/wrinkles, appearance of skin tone (evenness), appearance of pores, appearance of texture/smoothness, firmness (visual), elasticity (tactile), and overall appearance.

Clinical expert grading. Grading for Efficacy: Visual and tactile assessments were performed using 10 cm Visual Analog Scales (VAS) on bilateral face at baseline, week 6 and week 12. The following parameters were evaluated: fine lines/wrinkle, skin tone (color evenness), texture/smoothness (visual), firmness (visual), elasticity (tactile), skin pores, radiance/luminosity, and overall appearance using the instruments and methods detailed below.

Corneometer: Corneometer CM 825 (Courage+Khazaka, Germany) was used to evaluate skin moisture content/hydration by measuring skin capacitance. Measurements were taken in triplicate and averaged on bilateral face at baseline, week 6 and week 12. A test site map was used to ensure the same location is measured at each visit.

Vapo Meter: The VapoMeter (Delfin Technologies Ltd., Finland) measures the trans-epidermal water loss (TEWL) of the skin with a closed cylindrical chamber which has sensors to measure relative humidity and temperature. Changes in TEWL rates provide a measure of barrier disruption or integrity, thereby providing an indication of the effect of Peptide 14 on skin integrity. All subjects had VapoMeter measurements taken in duplicate and averaged on the bilateral face at baseline, week 6 and week 12. Assessment location was recorded on a body map for each subject.

Ultrasound—DermaScan: The DermaScan C USB (Cortex Technology ApS, Hadsund, Denmark) is a compact high-resolution ultrasound scanner. All subjects had ultrasound assessments taken on the bilateral face at baseline and week 12. The location of assessments was the same at each visit and was recorded on a face map. Upon acquisition of the ultrasound scans, they were analyzed for dermal thickness (density) and echogenicity.

SIAScope: The COSMETRICS™ SIAScope (Astron Clinical, Toft, UK) is a non-invasive optical skin imaging instrument using Spectrophotometric Intracutaneous Analysis (SIA) or chromophore mapping. Dermal collagen and hemoglobin were measured on the bilateral face at baseline, week 6 and week 12.

Cutometer: The Cutometer MPA 580 (Courage+Khazaka, Germany) measures the viscoelastic properties of the skin (firmness and elasticity) by applying suction to the skin surface, drawing the skin into the aperture of the probe and determining the penetration depth using an optical measuring system. Measurements were taken on the bilateral face at baseline, week 6 and week 12. The same location was measured at each time point and recorded using a face map. Measurements included firmness, elasticity and net elasticity.

VISTA-CR: Photo documentation was provided using the VISTA-CR imaging system (Canfield Scientific, Paramus, NJ, USA) which captures high-resolution images in multiple lighting modes. Photographs were captured in standard 1 and parallel polarized light of the center, right and left view at baseline, week 6 and week 12.

ANTERA 3D®: The Antera 3D® (Miravex, Ireland) is an instrument combining skin profilometry, multi-spectral analysis and colorimetry to provide reconstruction of the skin surface in three dimensions and subsequent image analysis. Images were captured on the crow's feet area on the left and right in all subjects at baseline, week 6 and week 12. The same location was measured at each time point and recorded using a face map. Images were analyzed for texture, breadth and depth lines/wrinkles.

Expert Clinical Grading

Comparison of Week 6 and Week 12 to Baseline

Peptide 14 Formulation: Comparison of mean scores of the left side of the face treated with Peptide 14 at baseline to the subsequent time points revealed statistically significant improvements in clinical grading at week 6 which continued to week 12 for appearance of lines/wrinkles, skin tone (evenness), appearance of pores, texture/smoothness, firmness (visual), elasticity (tactile), and overall appearance. Additionally, the appearance of radiance/luminosity was statistically significantly improved at week 12 compared to the baseline for left side of the face treated with Peptide 14.

Control Formulation: Comparison of mean scores of the right side of the face treated with the negative control formulation at baseline to the subsequent time points revealed statistically significant improvements in clinical grading at week 6 which continued to Week 12 for appearance of lines/wrinkles, skin tone (evenness), appearance of pores, texture/smoothness, firmness (visual), elasticity (tactile), radiance/luminosity, and overall appearance.

Comparison of Peptide 14 Treatment to Negative Control (Left vs Right Side of Face)

Comparison of Peptide 14 Treatment to Negative Control with Treatment Time

Figure 16:
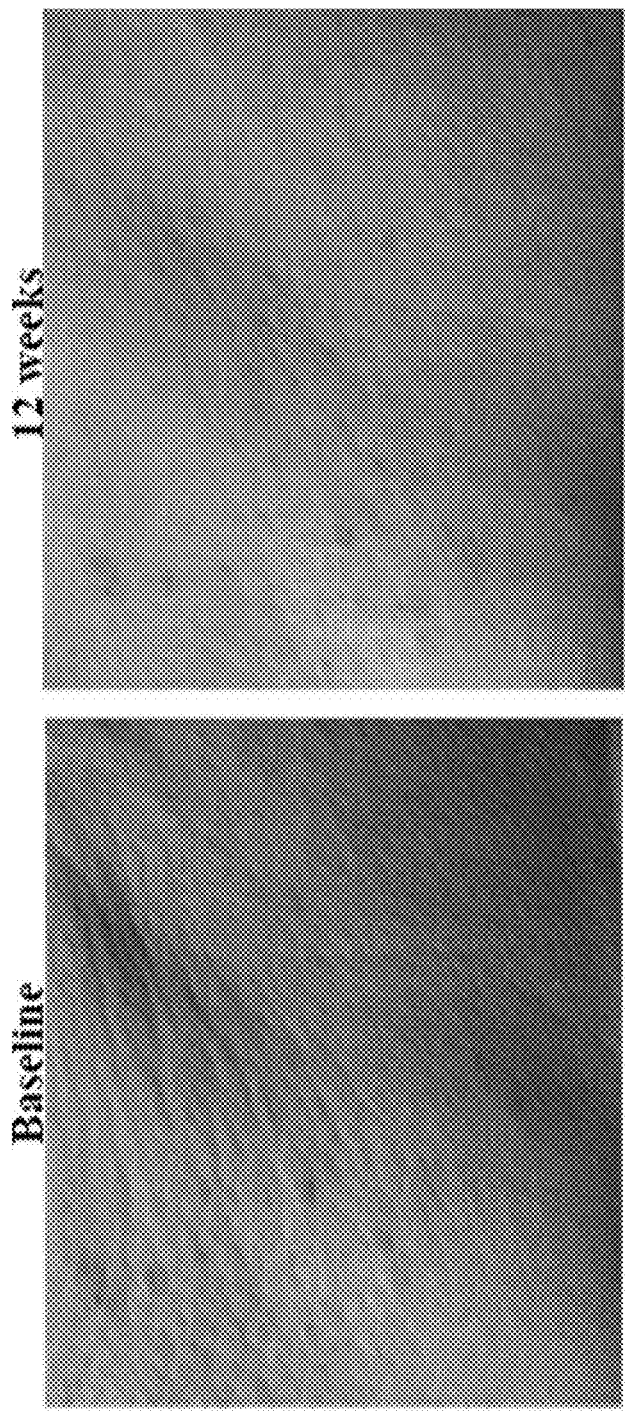
FIG. 16 illustrates an example of the left side of the face treated with Peptide 14 at baseline (left, Baseline) before treatment and after 12 weeks of treatment (right, 12 weeks).

When compared to baseline (before treatment), the left side of the face treated with Peptide 14 appeared to be better than the right side of the face treated with the negative control in some of the measurements. The left side of the face treated with Peptide 14 had higher level of skin hydration by Corneometer measurement, higher level of collagen level by SIAScope measurements at week 6, and better TEWL (transepithelial water loss) improvement by VapoMeter measurement at week 6 than the right side of the face treated with the negative control. No significant differences were seen between the left side of the face treated with Peptide 14 and the right side of the face treated with the negative control formulation for Dermascan assessment for dermal thickness (density) and echogenicity and Visia assessment for overall skin appearance. The left side of the face treated with Peptide 14 has better Antera measurement of texture (roughness) at week 12 than the right side of the face treated with the negative control formulation The results of 22 patients after 12 weeks using a topical cream with 0.01% Peptide 14 were analyzed. FIG. 16 shows an example of left side of the face treated with Peptide 14 at baseline (left, Baseline) and after 12 weeks of treatment (right, 12 weeks). The 12 weeks of treatment with 0.01% Peptide 14 appears to have decreased the appearance of lines and wrinkles and improved smoothness, skin tone (evenness), texture/smoothness, and overall appearance as compared to the baseline time point.

An analysis of blind expert opinion was performed to determine the percentage of patients showing improvement and mean percentage improvement (MPI) of all subjects, where MPI represents the mean percent improvement compared to baseline (before treatment). The analysis found 87% of patients assessed as having a reduction in appearance of skin wrinkles (MPI: 3.3%), 90% assessed as having improved skin elasticity (MPI: 4.75%), and 95.5% assessed as having an improvement in skin evenness (MPI: 4.4%), radiance (MPI: 5.06%), appearance of pores (MPI: 4.58%), and firmness (MPI: 5.43%). All subjects were assessed as presenting better skin texture/smoothness (MPI: 7.46%) and overall appearance (MPI: 6.17%).

The faces of the subjects were evaluated by various instruments to determine the percentages of patients showing improvement and mean percentage improvement (MPI) of all subjects, where MPI represents the mean percent improvement compared to baseline (before treatment). The instrumental evaluation found that 81% of the subjects had better skin barrier according to Vapometer evaluation (MPI: 14.19%). 73% of the subjects presented better skin roughness according to Antera evaluation (MPI: 5.05%). 73% of the subjects presented better skin radiance according to VISIA evaluation (MPI: 16.63%).

The perceptions of the subjects were also assessed. In the analysis of subjects' perception, greater than 80% of the subjects considered that the formulation comprising Peptide 14 promoted better skin appearance, better skin texture, better skin firmness, and better hydration. 78% of the subjects noticed an improvement in skin radiance.

Example 21

The topical formulation comprising at least one of the polypeptides disclosed herein is used on human skin. The formulation is directed to be applied as a smooth layer onto clean, dry skin on face and/or neck in the morning and the evening. The formulation is a daily essential topical supplement scientifically formulated to improve skin resilience and strengthen epidermal barrier for long-lasting health of the skin.

Example 22

A user applies the topical formulation described herein comprising at least one of the polypeptides to the face and/or neck. The user also applies another topical formulation comprising a UV blocker after applying the topical formulation.

Example 23

A user applies the topical formulation described herein comprising at least one of the polypeptides and a UV blocker to the face or the neck. The topical formulation may be applied to the skin on the body of the user.

Example 24

3D skin equivalent sections of samples built with cells from elder donors (71, 84 or 90 years old) were treated with 1 μM Peptide 14 or Peptide 13, or 20 μM Retinoic Acid (RA) and assessed for the effect of the various treatments of various markers of senescence, aging, and health.

Figure 17:
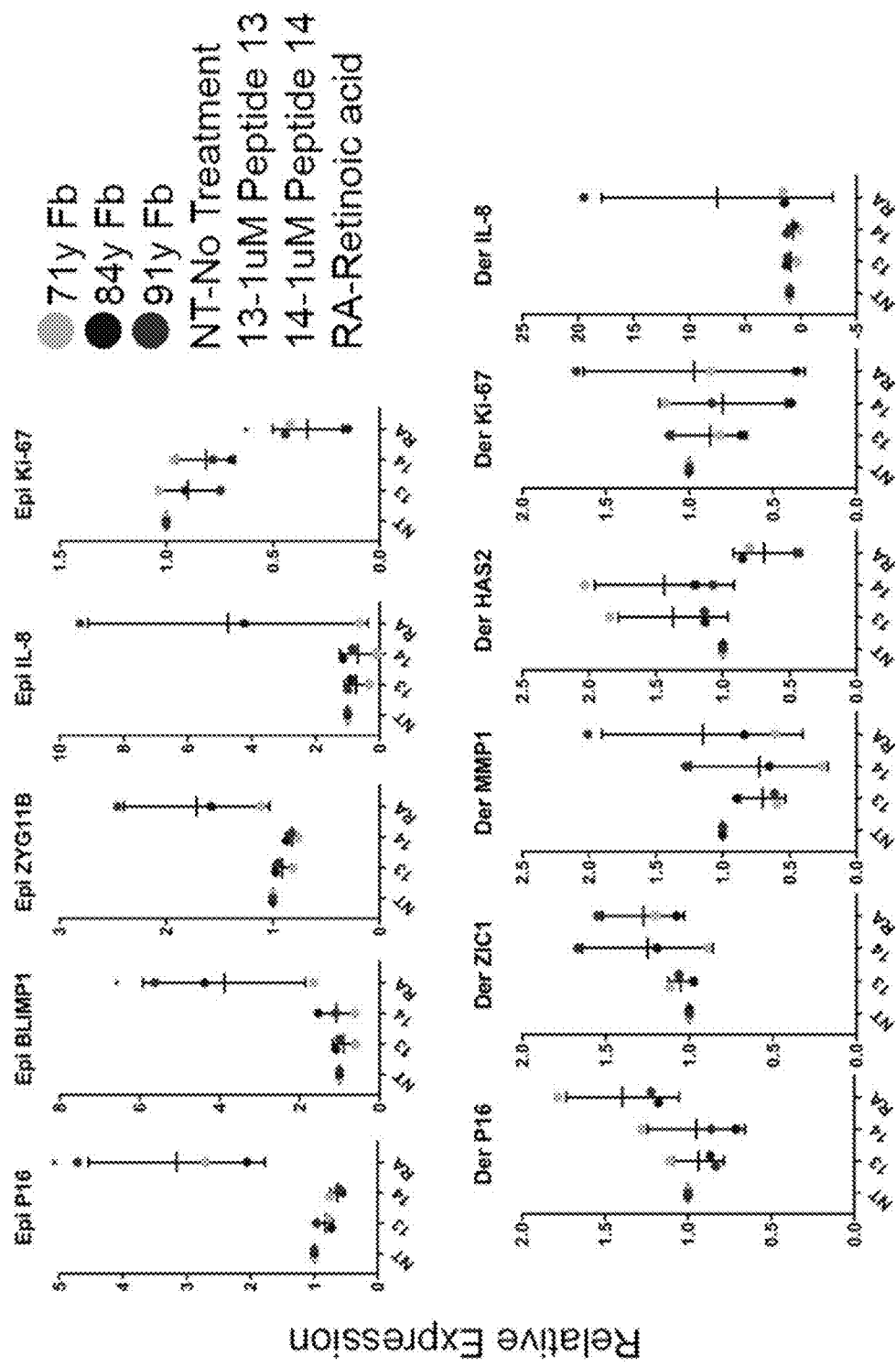
FIG. 17 illustrates relative mRNA expression levels of p16, BLIMP1, ZYG11B, IL-8, Ki-67, ZIC1, MMP1, HAS2 of the epidermal and dermal layers of 3D skin equivalents treated with a control, Peptide 14, Peptide 13, or Retinoic Acid. Data are presented as 2-ddCt normalized to GAPDH and untreated control. *p<0.05.

FIG. 17 shows the relative mRNA expression levels of p16, BLIMP1, ZYG11B, IL-8, Ki-67, ZIC1, MMP1, HAS2 of the epidermal (Epi) and dermal (Der) layers of 3D skin equivalents treated with a control, Peptide 14, Peptide 13, or Retinoic Acid. Data are presented as 2-ddCt normalized to GAPDH and untreated control. *p<0.05. Peptide 13 and Peptide 14-treated samples generally had similar relative mRNA expression levels for p16, BLIMP1, ZYG11B, IL-8, and Ki-67 in the epidermal layer, and for p16, MMP1, HAS2, IL-8, and Ki-67 in the dermal layer. Peptide 13 and Peptide 14-treated samples generally had lower relative mRNA expression levels than RA-treated samples for p16, BLIMP1, ZYG11B, IL-8, in the epidermal layer and for p16, MMP1, IL-8, and Ki-67 in the dermal layer. Peptide 13 and Peptide 14-treated samples generally had higher relative mRNA expression levels than RA-treated samples for Ki-67 in the epidermal layer and for HAS2 for the dermal layer. Peptide 13 and Peptide 14-treated samples had similar relative mRNA expression levels as RA-treated samples for ZIC1 and Ki-67 for dermal layer.

Example 25

Senotherapeutic strategies can be linked to healthspan and lifespan extension in vivo. In order to assess whether Peptide 14 promotes extended healthspan and lifespan, *Caenorhabditis elegans* worms were used. Peptide 14 was added in the worm media (M9 buffer media) at different concentrations of 1 µM or 2 µM. Negative control worms received vehicle only. Two healthspan parameters were assessed i) pharyngeal pumping and ii) worm movement. Lifespan was also determined. For pharyngeal pumping analysis, 15 worms had their pharynx movement (pumping) observed daily and counted for 20 seconds. This experiment was repeated 3 times, by 2 different blind observers, employing different populations of animals at different days. Statistical difference was detected by analyzing each individual time point by One-Way ANOVA and Dunnet's post hoc test. All groups were compared with the H2O group. For worm movement analysis, the basic movement of *C. elegans*, also called thrashing, was measured daily for 15 worms. Observation duration was 30 seconds. The experiment was repeated 3 times, by 2 different blind observers, employing different populations of worms at different days. Statistical difference was detected by analyzing each individual time point by One-Way ANOVA and Dunnet's post hoc, and all groups were compared with the H2O group. For lifespan analysis, 15 worms had their lifespan observed daily until the last worm died. This experiment was repeated 3 times, by 2 different blind observers, employing different populations of worms at different days. The average lifespan was measured. Statistical difference was detected by analyzing each individual time point by One-Way ANOVA and Dunnet's post hoc, and all groups were compared with the H2O group (FIG. 18).

Figure 18:
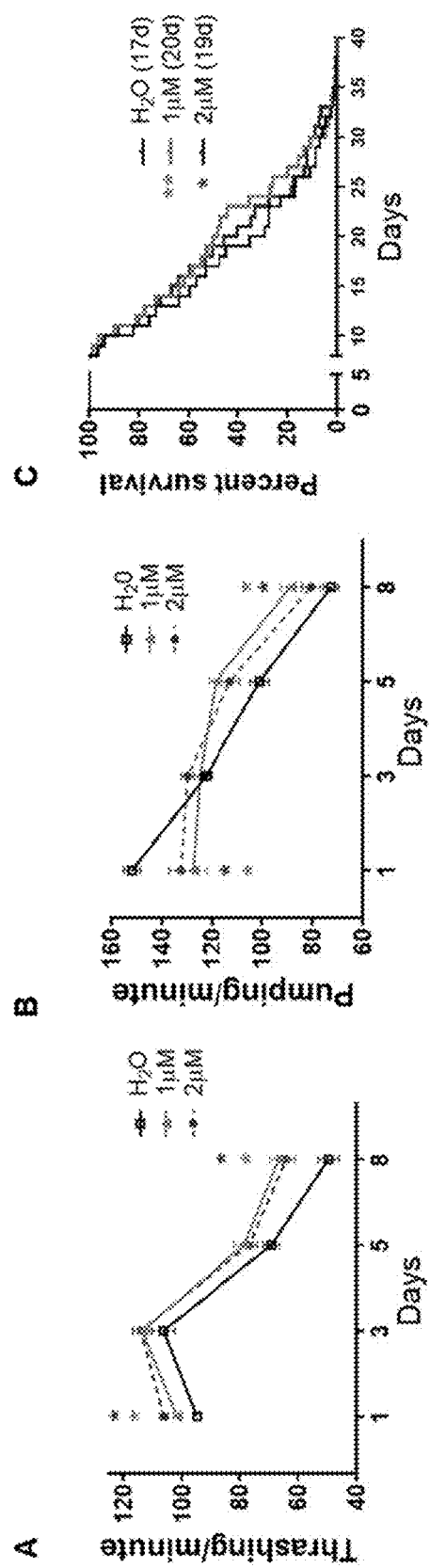
FIG. 18 illustrates prolonged life and healthspan of *Caenorhabditis elegans* (*C. elegans*) as acquired data indicating that treatment with either 1 µM or 2 µM polypeptide improved worm thrashing (panel A), pumping (panel B), and median lifespan (panel C). *p<0.05; **p<0.01.

Treatment with either 1 µM or 2 µM of Peptide 14 improved worm thrashing (FIG. 18, panel A), pumping (FIG. 18, panel B), and lifespan (FIG. 18, panel C). While thrashing was significantly improved in day 1 (*p<0.05), pumping was significantly decreased at this day (*p<0.5). Taken together, the data suggest safety and efficacy of the tested peptides with regards to promoting healthspan and lifespan. For instance, on day 8, both thrashing (*p<0.05) and pumping (*p<0.05) were increased in the groups treated with Peptide 14 compared to control. Pumping decreases with aging in *C. elegans*, mainly as a result of muscular integrity loss. Even though not directly measured, defects in the macroscopic anatomy of *C. elegans*' pharynx (bent or swollen pharynx, both common features of this nematode aging) were also reduced in the 1 µM Peptide 14 group when compared to the H2O control group. No decrease in worm movement was detected in either time point or sample, suggesting that the peptide was not toxic to *C. elegans* at the concentrations tested. When used at 1 µM and 2 µM, Peptide 14 promoted a statistically significant increase in worm average lifespan (1 µM Peptide 14 **p<0.01; 2 µM peptide14 *p<0.05).

Example 26

Skin cells from Progeria patients were used as a model of aging because of the high levels of cellular senescence. Primary fibroblasts from Progeria patients were cultured in DMEM (Dulbecco's Modified Eagle's Medium) supplemented with 10% v.v. fetal bovine serum (FBS), and 1% v.v. of penicillin/streptomycin solution (1,000 U·mL−1). Cells cultured at 5% $CO_2$, 37° C. and 95% humidity atmosphere. After expansion, the cells were seeded in 96-well plates (4,000 cells per well) and, 6 hours after plating, were incubated with 500 nM, 5 µM or 50 µM of polypeptide sequence LKGIL (SEQ ID NO: 6) or WLKGI (SEQ ID NO: 7). Negative control comprised untreated cells, which received vehicle only. After incubation, relative cellular senescence, which was assessed by the activity of senescence associated β-galactosidase staining relative to untreated control and by the quantification of ATRX foci/nuclei, was analyzed. Three independent experiments (biological replicates) including three technical replicates were performed. Data was analyzed using ANOVA and a Bonferroni post-hoc test. Statistical significance was determined as p values equal or lower than 0.05, where *p<0.05 and ** p<0.01.

Figure 19:
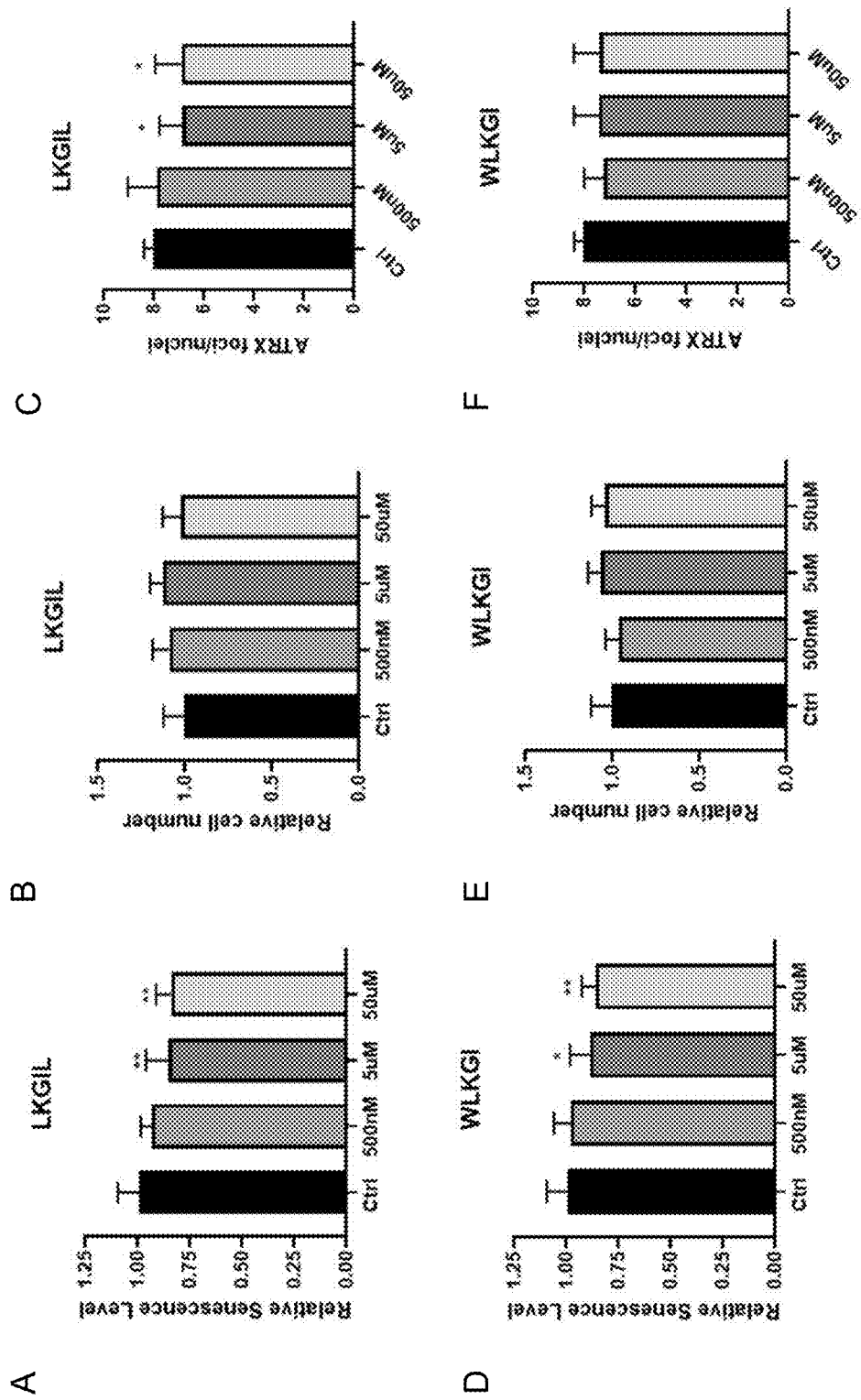
FIG. 19 illustrates the effect of polypeptide sequence LKGIL (SEQ ID NO:6) (A, B, C), and polypeptide sequence WLKGI (SEQ ID NO:7) (D, E, F) to decrease cellular senescence without promoting cell death. In panels A and D, the y-axis indicates the relative senescence level normalized to untreated control. In panels B and D, y-axis indicates the relative cell number normalized to untreated control. In panels C and F, y-axis indicates the average ATRX foci accumulation per cell. *p<0.05; **p<0.01.

FIG. 19 shows the effect of polypeptide sequences LKGIL (SEQ ID NO: 6) (A, B, C), and WLKGI (SEQ ID NO: 7) (D, E, F) to decrease cellular senescence without promoting cell death. In panels A and D, the y-axis indicates the relative senescence level normalized to untreated control. In panels B and D, y-axis indicates the relative cell number normalized to untreated control. In panels C and F, y-axis indicates the average ATRX foci accumulation per cell. Treatment of cells with LKGIL (SEQ ID NO: 6) significantly decreased senescence associated β-galactosidase staining and the average number of ATRX foci/nuclei, when used at 5 µM and 50 µM, compared to untreated cells (p<0.01 for β-galactosidase staining and p<0.05 for ATRX foci/nuclei). Treatment of cells with WLKGI (SEQ ID NO: 7) decreased senescence associated β-galactosidase staining levels when used at 5 µM and 50 µM as compared to untreated cells (p<0.05 for 5 µM and p<0.01 for 50 µM). No cellular toxicity was observed in the tested concentrations.

Example 27

Additional polypeptides were tested for suitability as an anti-senescent agent. Cells were incubated with one of the polypeptides. Negative control comprised untreated cells, which received vehicle only. After incubation, relative cellular senescence (assessed by the activity of senescence associated β-galactosidase staining relative to negative control) and relative cell proliferation relative to negative control were analyzed. A number of polypeptides showed relative cellular senescence lower than 1, having decreased cellular senescence than the untreated negative control, and maintained cell proliferation at or above that of the untreated negative control. Examples of such polypeptides shown in Table 6.

Further, a dose-dependent effects of polypeptides of Table 6 on cell senescence were studied. The cells were incubated various doses of the polypeptides ranging from 1.26 µM to 50 µM (1.26 µM, 3.12 µM, 6.25 µM, 12.5 µM, 25 µM, 50 µM). There was noticeable decrease in cell senescence even at lower doses for the polypeptides.

TABLE 6

Polypeptides

| SEQ ID NO. | Polypeptide sequence |
|---|---|
| 9 | STAKAWLKGI |
| 10 | ETAKAWEKGI |
| 11 | ETAKAWHKGI |
| 12 | ETAKAWLKSI |
| 13 | ETAKAWLKGE |
| 14 | ETAKAWLKGI |
| 15 | WLKGILRGAA |
| 16 | KTAKAWLKGI |
| 17 | NTAKAWLKGI |
| 18 | PTAKAWLKGI |
| 19 | QTAKAWLKGI |
| 20 | EQAKAWLKGI |
| 21 | WLKGICRGAA |
| 22 | WLKGILPGAA |
| 23 | WLKGILQGAA |
| 24 | WLKGILSGAA |
| 25 | WLKGILVGAA |
| 26 | WLKGILRAAA |
| 27 | WLKGILRGHA |
| 28 | WLKGILRGIA |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXEMPLARY EMBODIMENTS

Among the exemplary embodiments are:

Embodiment 1 comprises compositions for treatment of skin comprising an isolated, synthetic, or recombinant polypeptide comprising an amino acid sequence of LKGI (SEQ ID NO:5) or an analog thereof, wherein in the polypeptide comprises no more than 100 amino acids.

Embodiment 2. The compositions of embodiment 1, wherein the isolated, synthetic, or recombinant polypeptide comprises an amino acid sequence of WLKGI (SEQ ID NO:7) or an analog thereof. Embodiment 3. The compositions of embodiment 1 or embodiment 2, wherein the isolated, synthetic, or recombinant polypeptide comprises an amino acid sequence of LKGIL (SEQ ID NO:6) or an analog thereof. Embodiment 4. The compositions of any one of embodiments 1-3, wherein the isolated, synthetic, or recombinant polypeptide comprises at least 4 amino acids, 10 amino acids, 15 amino acids, or 20 amino acids. Embodiment 5. The compositions of any one of embodiments 1-4, further comprising a therapeutic, nutraceutical, or cosmetic excipient. Embodiment 6. The compositions of embodiment 5, wherein the excipient is configured for topical application. Embodiment 7. The compositions of any one of embodiments 1-6, wherein the compositions are configured for application to human skin. Embodiment 8. The compositions of any one of embodiments 1-7, wherein the compositions is a cream, a transdermal patch, a topical patch, an ointment, an oil, a gel, a liquid, a powder, a lotion, a serum, an emulsion, a moisturizer, a foam, a face mask, a mousse, an aerosol, a spray, a cleanser, a toner, or a shampoo. Embodiment 9. The compositions of any one of embodiments 1-5, wherein the compositions are configured as an edible supplement. Embodiment 10. The compositions of embodiment 9, wherein the compositions is configured as a beverage. Embodiment 11. The compositions of any one of embodiments 1-9, wherein the compositions comprise at least one skin hydrating agent selected from a group consisting of glycerin, squalene, sorbitol, hyaluronic acid, hyaluronic acid derivatives, sodium hyaluronate, sodium hyaluronate crosspolymer, niacinamide, glycoproteins, pyrrolidone carboxylic acid (PCA), lysine HCl, allantoin and algae extract. Embodiment 12. The compositions of any one of embodiments 1-9, wherein the compositions comprise at least one emollient selected from a group consisting of plant oils, mineral oil, shea butter, cocoa butter, petrolatum, fatty acids, triglycerides, benzoates, myristates, palmitates, stearates, glycolipids, phospholipids, squalene, glycerin, ceramide, and algae extract. Embodiment 13. The compositions of embodiment 12, wherein the plant oil is selected from a group consisting of rose hip oil, andiroba oil, grape seed oil, avocado oil, plum seed oil, pracaxi oil, *Calycophyllum spruceanum* oil, almond oil, and argan oil. Embodiment 14. The compositions of any one of embodiments 1-13, wherein the compositions comprises at least one vitamin selected from a group consisting of vitamin A, vitamin D, vitamin E, vitamin F, vitamin K, vitamin B1 (thiamine), vitamin B2 (riboflavin), vitamin B3 (niacin), vitamin B5 (pantothenic acid), vitamin B7 (biotin), vitamin B6, vitamin B12 (cyanocobalamin), vitamin B9, folic acid, niacinamide, or derivatives thereof. Embodiment 15. The compositions of any one of embodiments 1-14, wherein the compositions comprise an effective amount of the isolated, synthetic, or recombinant polypeptide of about 500 nM to about 500 µM. Embodiment 16. The compositions of any one of embodiments 1-14, wherein the compositions comprise an effective amount of the isolated, synthetic, or recombinant polypeptide of about 0.001% to about 5% (w/w). Embodiment 17. The compositions of any one of embodiments 1-16, wherein the compositions are formulated to achieve low dermal penetration of no more than 10% of the isolated, synthetic, or recombinant polypeptide into the dermis. Embodiment 18. The compositions of any one of embodiments 1-17, wherein the compositions improve at least one of skin moisture content, trans-epidermal water loss (TEWL), dermal thickness and echogenicity, intracutaneous analysis, skin viscoelastic properties, or skin surface profile of skin of a user after using compositions on the skin as compared to before using the compositions. Embodiment 19. The compositions of any one of embodiments 1-17, wherein the compositions reduces appearance of lines/wrinkles, appearance of skin tone (evenness), appearance of pores, appearance of texture/smoothness, firmness (visual), elasticity (tactile), epidermal barrier, skin roughness, skin hyperpigmentation, or overall appearance of skin of a user after using compositions on the skin as compared to before using the compositions. Embodiment 20. The compositions of any one of embodiments 1-19, wherein the treatment of skin with the composition reduces or treats an effect of aging on the skin. Embodiment 21. The compositions of any one of embodiments 1-20, wherein treatment of skin with the composition reduces an effect of cellular senescence on the skin. Embodiment 22. The compositions of any one of embodiments 20-21, wherein the effect of aging is assessed by at least one of senescence associated β-galactosidase activity level, a ratio of ATRX foci/cell, p16 expression, IL-8 expression, Ki-67 expression, hyaluronic synthase 2 expression, matrix metalloprotease 1 (MMP1) expression, sirtuin 6 (SIRT6) expression, BLM expression, or exonuclease 1 (EXO1) expression.

Embodiment 23 comprises an isolated, synthetic, or recombinant polypeptide comprising an amino acid sequence of $X_1X_2X_3X_4X_5X_6X_7X_8X_9X_{10}$ or an analog thereof, wherein: (a) the amino acid sequence has at least 70%, 80%, 85%, 90%, or 95% identity to a first sequence SEQ ID NO: 1 wherein $X_1$ is E, $X_2$ is T, $X_4$ is K, $X_6$ is W, $X_7$ is L, $X_9$ is G, and $X_{10}$ is I; and (i) $X_3$ is not S (SEQ ID NO: 8); or (ii) if $X_5$ is any amino acid then $X_8$ is not G (SEQ ID NO: 29); or (iii) if $X_8$ is any amino acid then $X_5$ is not N (SEQ ID NO: 30); or (iv) any one of (i), (ii), or (iii) optionally with 1, 2, 3, or 4 conservative amino acid substitutions; or (b) the amino acid sequence has at least 70%, 80%, 85%, 90%, or 95% identity to a second sequence SEQ ID NO:2 wherein $X_1$ is A, $X_2$ is T, $X_3$ is A, $X_4$ is K, $X_5$ is A, $X_6$ is W, $X_7$ is L, $X_8$ is K, $X_9$ is G, and $X_{10}$ is I, optionally with 1, 2, 3, or 4 conservative amino acid substitutions; or (c) the amino acid sequence has at least 70%, 80%, 85%, 90%, or 95% identity to a third sequence SEQ ID NO:3 wherein $X_1$ is K, $X_2$ is L, $X_5$ is I, $X_6$ is L, $X_8$ is G, and $X_{10}$ is A; and (i) if $X_9$ is any amino acid then $X_3$ is not N (SEQ ID NO: 31); or (ii) if $X_3$ is any amino acid then $X_9$ is not S (SEQ ID NO: 32); or (iii) if $X_4$ is any amino acid then $X_7$ is not L (SEQ ID NO: 33); or (iv) if $X_7$ is any amino acid then $X_4$ is not S (SEQ ID NO: 34), and; or (v) any one of (i), (ii), (iii), or (iv) optionally with 1, 2, 3, or 4 conservative amino acid substitutions; or (d) the amino acid sequence has at least 70%, 80%, 85%, 90%, or 95% identity to a fourth sequence SEQ ID NO:4 wherein $X_1$ is W, $X_2$ is L, $X_3$ is K, $X_4$ is G, $X_5$ is I, $X_6$ is L, $X_7$ is R, $X_8$ is E, $X_9$ is A, and $X_{10}$ is A, optionally with 1, 2, 3, or 4 conservative amino acid substitutions. Embodiment 24. The polypeptide of embodiment 23, wherein the amino acid sequence comprises LKGI (SEQ ID NO:5). Embodiment 25. The polypeptide of embodiment 23 or embodiment 24, wherein the amino acid sequence comprises WLKGI (SEQ ID NO:7). Embodiment 26. The polypeptide of any one of embodiments 23-25, wherein the amino acid sequence comprises LKGIL (SEQ ID NO:6). Embodiment 27. The polypeptide of embodiment 23, wherein the amino acid sequence has at least 70%, 80%, 85%, 90%, or 95% identity to a sequence of SEQ ID NO:1. Embodiment 28. The polypeptide of embodiment 23, wherein the amino acid sequence is SEQ ID NO:1. Embodiment 29. The polypeptide of embodiment 23, wherein the amino acid sequence is SEQ ID NO:2. Embodiment 30. The polypeptide of embodiment 23, wherein the amino acid sequence has at least 70%, 80%, 85%, 90%, or 95% identity to a sequence of SEQ ID NO:3. Embodiment 31. The polypeptide of embodiment 23, wherein the amino acid sequence has at least 80%, 85%, 90%, or 95% identity to a sequence of SEQ ID NO:3. Embodiment 32. The polypeptide of embodiment 23, wherein the amino acid sequence is SEQ ID NO:3. Embodiment 33. The polypeptide of embodiment 23, wherein the amino acid sequence is SEQ ID NO:4. Embodiment 34. The polypeptide of any one of embodiments 23-33, wherein the recombinant polypeptide comprises at least 10 amino acids, 15 amino acids, or 20 amino acids and no more than 100 amino acids. Embodiment 35 comprises compositions for treatment of skin comprising at least one isolated, synthetic, or recombinant polypeptide of any one of embodiments 23-34 and a therapeutic, nutraceutical, or cosmetic excipient. Embodiment 36. The compositions of embodiment 35, wherein the excipient is configured for topical application. Embodiment 37. The compositions of embodiment 35 or embodiment 36, wherein the compositions is formulated for application to human skin. Embodiment 38. The compositions of any one of embodiments 35-37, wherein the compositions is a cream, an ointment, a gel, a liquid, an oil, a powder, a lotion, a serum, an emulsion, a moisturizer, a foam, a face mask, a mousse, an aerosol, a spray, a cleanser, a toner, a topical patch, or a shampoo. Embodiment 39. The compositions of embodiment 35, wherein the compositions is configured as an edible supplement. Embodiment 40. The compositions of embodiment 39, wherein the compositions is configured as a beverage.

Embodiment 41. The compositions of any one of embodiments 35-40, wherein the compositions comprise at least one skin hydrating agent selected from a group consisting of glycerin, squalene, sorbitol, hyaluronic acid, hyaluronic acid derivatives, sodium hyaluronate, sodium hyaluronate crosspolymer, niacinamide, glycoproteins, pyrrolidone carboxylic acid (PCA), lysine HCl, allantoin and algae extract. Embodiment 42. The compositions of any one of embodiments 35-40, wherein the compositions comprise at least one emollient selected from a group consisting of plant oils, mineral oil, shea butter, cocoa butter, petrolatum, fatty acids, triglycerides, benzoates, myristates, palmitates, stearates, glycolipids, phospholipids, squalene, glycerin, ceramide, and algae extract. Embodiment 43. The compositions of embodiment 42, wherein the plant oil is selected from a group consisting of rose hip oil, andiroba oil, grape seed oil, avocado oil, plum seed oil, pracaxi oil, *Calycophyllum spruceanum* oil, almond oil, and argan oil. Embodiment 44. The compositions of any one of embodiments 35-43, wherein the compositions comprises at least one vitamin selected from a group consisting of vitamin A, vitamin D, vitamin E, vitamin F, vitamin K, vitamin B1 (thiamine), vitamin B2 (riboflavin), vitamin B3 (niacin), vitamin B5 (pantothenic acid), vitamin B7 (biotin), vitamin B6, vitamin B12 (cyanocobalamin), vitamin B9, folic acid, niacinamide, or derivatives thereof. Embodiment 45. The compositions of any one of embodiments 35-44, wherein the compositions comprise an effective amount of the isolated, synthetic, or recombinant polypeptide of about 500 nM to about 500 μM. Embodiment 46. The compositions of any one of embodiments 35-44, wherein the compositions comprise an effective amount of the isolated, synthetic, or recombinant polypeptide of about 0.001% to about 5% (w/w). Embodiment 47. The compositions of any one of embodiments 35-44, wherein the compositions comprises an effective amount of the isolated, synthetic or recombinant polypeptide of about 0.001% to about 1%. Embodiment 48. The compositions of any one of embodiments 35-47, wherein the compositions improve at least one of skin moisture content, trans-epidermal water loss (TEWL), dermal thickness and echogenicity, intracutaneous analysis, skin viscoelastic properties, or skin surface profile of skin of a user after using compositions on the skin as compared to before using the compositions. Embodiment 49. The compositions of any one of embodiments 35-47, wherein the compositions reduces appearance of lines/wrinkles, appearance of skin tone (evenness), appearance of pores, appearance of texture/smoothness, firmness (visual), elasticity (tactile), epidermal barrier, skin roughness, skin hyperpigmentation, or overall appearance of skin of a user after using compositions on the skin as compared to before using the compositions. Embodiment 50. The compositions of any one of embodiments 35-49, wherein the treatment of skin with the composition reduces or treats an effect of aging on the skin. Embodiment 51. The compositions of any one of embodiments 35-50, wherein the treatment of skin with the composition reduces an effect of cellular senescence on the skin. Embodiment 52. The compositions of any one of embodiments 50-51, wherein the effect of aging is assessed by at least one of senescence associated B-galactosidase activity level, a ratio of ATRX foci/cell, p16 expression, IL-8 expression, Ki-67 expression, hyaluronic synthase 2 expression, matrix metalloprotease 1 (MMP1) expression, sirtuin 6 (SIRT6) expression, BLM expression, or exonuclease 1 (EXO1) expression.

Embodiment 53 comprises methods of treating a condition in a subject in need thereof, the method comprising administering to the subject a composition comprising an amino acid sequence of SEQ ID NO:5. Embodiment 54. The method of embodiment 53, wherein the formulation comprises an amino acid sequence of SEQ ID NO:6. Embodiment 55. The method of embodiment 53 or embodiment 54, wherein the composition comprises an amino acid sequence of SEQ ID NO:7. Embodiment 56. The method of any one of embodiments 53-55, wherein the administering comprises topically applying the compositions to the subject. Embodiment 57. The method of any one of embodiments 53-56, wherein the subject is a human or other animal. Embodiment 58. The method of any one of embodiments 53-57, wherein the method comprises administering an effective amount of the compositions to the subject. Embodiment 59. The method of any one of embodiments 53-58, wherein the condition is a disorder associated with accumulation of senescent cells in the subject. Embodiment 60. The method of embodiment 53, wherein the disorder associated with accumulation of senescent cells comprises aging skin. Embodiment 61. The method of any one of embodiments 53-60, wherein the compositions comprises at least one skin hydrating agent selected from a group consisting of glycerin, squalene, sorbitol, hyaluronic acid, hyaluronic acid derivatives, sodium hyaluronate, sodium hyaluronate crosspolymer, niacinamide, glycoproteins, pyrrolidone carboxylic acid (PCA), lysine HCl, allantoin and algae extract. Embodiment 62. The method of any one of embodiments 53-61, wherein the compositions comprises at least one emollient selected from a group consisting of plant oils, mineral oil, shea butter, cocoa butter, petrolatum, fatty acids, triglycerides, benzoates, myristates, palmitates, stearates, glycolipids, phospholipids, squalene, glycerin, ceramide, and algae extract. Embodiment 63. The method of embodiment 62, wherein the plant oil is selected from a group consisting of rose hip oil, andiroba oil, grape seed oil, avocado oil, plum seed oil, pracaxi oil, *Calycophyllum spruceanum* oil, almond oil, and argan oil. Embodiment 64. The method of any one of embodiments 53-63, wherein the compositions comprises at least one vitamin selected from a group consisting of vitamin A, vitamin D, vitamin E, vitamin F, vitamin K, vitamin B1 (thiamine), vitamin B2 (riboflavin), vitamin B3 (niacin), vitamin B5 (pantothenic acid), vitamin B7 (biotin), vitamin B6, vitamin B12 (cyanobalamin), vitamin B9, folic acid, niacinamide, or derivatives thereof. Embodiment 65. The method of any one of embodiments 53-64, wherein the compositions comprises an effective amount of the isolated, synthetic, or recombinant polypeptide of about 500 nM to about 500 μM. Embodiment 66. The method of any one of embodiments 53-64, wherein the compositions comprises an effective amount of the isolated, synthetic, or recombinant polypeptide of about 0.001% to about 5% (w/w). Embodiment 67. The method of any one of embodiments 53-66, wherein the compositions is formulated to achieve low dermal penetration of no more than 10% of the isolated, synthetic, or recombinant polypeptide into the dermis. Embodiment 68. The method of any one of embodiments 53-67, wherein the compositions improves at least one of skin moisture content, trans-epidermal water loss (TEWL), dermal thickness and echogenicity, intracutaneous analysis, skin viscoelastic properties, or skin surface profile of skin of a user after using compositions on the skin as compared to before using the compositions. Embodiment 69. The method of any one of embodiments 53-68, wherein the compositions reduces appearance of lines/wrinkles, appearance of skin tone (evenness), appearance of pores, appearance of texture/smoothness, firmness (visual), elasticity (tactile), epidermal barrier, skin roughness, skin hyperpigmentation, or overall appearance of skin of a user after using compositions on the skin as compared to before using the compositions. Embodiment 70. The method of any one of embodiments 53-69, wherein treating a skin with the composition reduces or treats an effect of aging on the skin. Embodiment 71. The method of any one of embodiments 53-70, wherein treating the skin with the composition reduces an effect of cellular senescence on the skin. Embodiment 72. The method of any one of embodiments 70-71, wherein the effect of aging is assessed by at least one of senescence associated B-galactosidase activity level, a ratio of ATRX foci/cell, p16 expression, IL-8 expression, Ki-67 expression, hyaluronic synthase 2 expression, matrix metalloprotease 1 (MMP1) expression, sirtuin 6 (SIRT6) expression, BLM expression, or exonuclease 1 (EXO1) expression.

Embodiment 73. A method of reducing cellular senescence in a subject in need thereof, the method comprising administering to the subject a composition comprising a polypeptide comprising an amino acid sequence of LKGI (SEQ ID NO:5) optionally with 1 conservative amino acid substitution, wherein in the polypeptide comprises no more than 100 amino acids. Embodiment 74. The method of embodiment 73, wherein the polypeptide comprises at least 4 amino acids, 10 amino acids, 15 amino acids, or 20 amino acids. Embodiment 75. The method of embodiment 73, wherein the compositions comprises an amino acid sequence of WLKGI (SEQ ID NO:7) optionally with 1 conservative amino acid substitution. Embodiment 76. The method of embodiment 73, wherein the compositions comprises an amino acid sequence of LKGIL (SEQ ID NO:6) optionally with 1 conservative amino acid substitution. Embodiment 77. The method of embodiment 75 or embodiment 76, wherein the polypeptide comprises at least 5 amino acids, 10 amino acids, 15 amino acids, or 20 amino acids and comprises no more than 100 amino acids. Embodiment 78. The method of any one of embodiments 73-77, wherein the compositions further comprises a therapeutic, nutraceutical, or cosmetic excipient. Embodiment 79. A method of reducing cellular senescence in a subject in need thereof, the method comprising administering to the subject a therapeutic, nutraceutical, or cosmetic compositions comprising at least one polypeptide of any one of embodiments 23-34.

Embodiment 80. The method of embodiment 79, wherein the compositions further comprises a therapeutic, nutraceutical, or cosmetic excipient. Embodiment 81. The method of embodiment 79 or embodiment 80, wherein the administering comprises applying the compositions to a portion of the skin of the subject. Embodiment 82. The method of any one of embodiments 79-81, wherein the compositions extends a lifespan of a plurality of cells of the subject, induces SIRT6 expression in a plurality of cells of the subject, increases cell renewal rates in a plurality of cells of the subject, promotes apoptosis in a plurality of cells of the subject, promotes DNA repair in a plurality of cells of the subject, increases collagen production in a plurality of cells of the subject, increases hyaluronic synthase production in a plurality of cells of the subject, decreases ATRX nuclear foci accumulation in a plurality of cells of the subject, decreases p16 expression in a plurality of cells of the subject, decreases senescence associated beta-galactosidase production in a plurality of cells of the subject, decreases IL8 expression in a plurality of cells of the subject, decreases MMP1 expression in a plurality of cells of the subject, increases BLM expression in a plurality of cells of the subject, and/or prevents UV-induced DNA damage in a plurality of cells of the subject.

Embodiment 83 comprises methods of treating a condition in a subject in need thereof, the method comprising administering to the subject a therapeutic, nutraceutical, or cosmetic compositions comprising an amino acid sequence of SEQ ID NO:5 optionally with 1 conservative amino acid substitution. Embodiment 84. The method of embodiment 83, wherein the therapeutic, nutraceutical, or cosmetic compositions comprises an amino acid sequence of SEQ ID NO:6 optionally with 1 conservative amino acid substitution. Embodiment 85. The method of embodiment 83 or embodiment 84, wherein the therapeutic, nutraceutical, or cosmetic compositions comprises an amino acid sequence of SEQ ID NO:7 optionally with 1 conservative amino acid substitution.

What is claimed is:

1. A composition comprising a polypeptide comprising an amino acid sequence selected from a group consisting of ETAKHWLKGI (SEQ ID NO: 1), ATAKAWLKGI (SEQ ID NO:2), KLKGILRGAA (SEQ ID NO:3), and WLKGIL-REAA (SEQ ID NO: 4).

2. The composition of claim 1, wherein the polypeptide comprises at least 10 amino acids, 15 amino acids, or 20 amino acids.

3. The composition of claim 1, wherein the composition is formulated for application to skin.

4. The composition of claim 3, wherein the composition is a cream, a transdermal patch, a topical patch, an ointment, an oil, a gel, a liquid, a powder, a lotion, a serum, an emulsion, a moisturizer, a foam, a face mask, a mousse, an aerosol, a spray, a cleanser, a toner, or a shampoo.

5. The composition of claim 1, wherein the composition further comprises a UV blocker.

6. The composition of claim 5, wherein the UV blocker comprises at least one of aminobenzoic acid, avobenzone, cinoxate, dioxybenzone, homosalate, meradimate, octocrylene, octinoxate, octisalate, oxybenzone, padimate O, ensulizole, sulisobenzone, titanium dioxide, trolamine salicylate, or zinc oxide.

7. The composition of claim 1, wherein the composition comprises at least one emollient selected from a group consisting of plant oil, mineral oil, shea butter, cocoa butter, petrolatum, fatty acid, triglyceride, benzoate, myristate, palmitates, stearates, glycolipids, phospholipids, squalene, glycerin, ceramide, and algae extract.

8. The composition of claim 7, wherein the plant oil comprises at least one of jojoba oil, rose hip oil, andiroba oil, grape seed oil, avocado oil, plum seed oil, pracaxi oil, *Calycophyllum spruceanum* oil, almond oil, or argan oil.

9. The composition of claim 1, wherein the composition comprises at least one skin hydrating agent selected from a group consisting of glycerin, squalene, sorbitol, hyaluronic acid, hyaluronic acid derivative, sodium hyaluronate, sodium hyaluronate crosspolymer, niacinamide, glycoprotein, pyrrolidone carboxylic acid (PCA), lysine HCl, allantoin, and algae extract.

10. The composition of claim 1, wherein the composition comprises at least one vitamin selected from a group consisting of vitamin A, vitamin C, vitamin D, vitamin E, vitamin F, vitamin K, vitamin B1 (thiamine), vitamin B2 (riboflavin), vitamin B3 (niacin), vitamin B5 (pantothenic acid), vitamin B7 (biotin), vitamin B6, vitamin B 12 (cyanocobalamin), vitamin B9, folic acid, niacinamide, and derivatives thereof.

11. The composition of claim 1, wherein the composition comprises an amount of the polypeptide of about 500 nM to about 500 μM.

12. The composition of claim 1, wherein the composition comprises an amount of the polypeptide of about 0.001% to about 5% (w/w).

13. The composition of claim 1, wherein the amino acid sequence is ETAKHWLKGI (SEQ ID NO:1).

14. The composition of claim 1, wherein the amino acid sequence is ATAKAWLKGI (SEQ ID NO:2).

* * * * *